US011344606B2

(12) United States Patent
Wilkinson et al.

(10) Patent No.: US 11,344,606 B2
(45) Date of Patent: May 31, 2022

(54) PARATHYROID HORMONE FUSION POLYPEPTIDE

(71) Applicant: University of Sheffield, Sheffield (GB)

(72) Inventors: Ian Wilkinson, Sheffield (GB); Richard Ross, Sheffield (GB)

(73) Assignee: University of Sheffield, Sheffield (GB)

( * ) Notice: Subject to any disclaimer, the term of this patent is extended or adjusted under 35 U.S.C. 154(b) by 162 days.

(21) Appl. No.: 16/608,611

(22) PCT Filed: Apr. 27, 2018

(86) PCT No.: PCT/GB2018/051120
§ 371 (c)(1),
(2) Date: Oct. 25, 2019

(87) PCT Pub. No.: WO2018/197895
PCT Pub. Date: Nov. 1, 2018

(65) Prior Publication Data
US 2020/0164033 A1 May 28, 2020

(30) Foreign Application Priority Data

Apr. 28, 2017 (GB) .................................... 1706781

(51) Int. Cl.
| | | |
|---|---|---|
| *A61K 38/29* | (2006.01) | |
| *C07K 14/635* | (2006.01) | |
| *C12N 15/62* | (2006.01) | |
| *A61K 38/16* | (2006.01) | |
| *C12N 15/63* | (2006.01) | |
| *A61K 38/17* | (2006.01) | |
| *A61K 31/593* | (2006.01) | |
| *A61K 33/10* | (2006.01) | |
| *C07K 14/72* | (2006.01) | |

(52) U.S. Cl.
CPC ........ *A61K 38/1796* (2013.01); *A61K 31/593* (2013.01); *A61K 33/10* (2013.01); *A61K 38/29* (2013.01); *C07K 14/635* (2013.01); *C07K 14/72* (2013.01); *C12N 15/62* (2013.01); *C07K 2319/00* (2013.01)

(58) Field of Classification Search
None
See application file for complete search history.

(56) References Cited

FOREIGN PATENT DOCUMENTS

| EP | 0950710 A2 | 10/1999 |
|---|---|---|
| WO | WO 2001/81408 A2 | 11/2001 |
| WO | WO 2006/010891 A2 | 2/2006 |
| WO | WO 2008/124166 A2 | 10/2008 |
| WO | WO 2010/111617 A2 | 9/2010 |
| WO | WO 2011/101284 A1 | 8/2011 |
| WO | WO 2012/123734 A1 * | 9/2012 |
| WO | WO 2013/090770 A2 | 6/2013 |
| WO | WO 2015/017529 A2 * | 2/2015 |
| WO | WO 2013/120060 A1 | 8/2016 |
| WO | WO 2016/183297 A1 | 11/2016 |

OTHER PUBLICATIONS

Katikaneni, et al. "Therapy for Alopecia Areata in Mice by Stimulating the Hair Cycle with Parathyroid Hormone Agonists Linked to a Collagen-Binding Domain," *J Investig Dermatol Symp Proc. 17*, No. 2:13-15, Nov. 2015.
Kostenuik, et al. "Infrequent Delivery of a Long-Acting PTH-Fc Fusion Protein Has Potent Anabolic Effects on Cortical and Cancellous Bone," *J Bone Miner Res. 22*, No. 70:1534-1547, Nov. 2007.
Lacey, et al. "Biomarker Profiling Differentials Sepsis from Cytokine Release Syndrome in Chimeric Antigen Receptor T-Cell Therapy for Acute Lymphoblastic Leukemia (ALL)," *Blood 128*, No. 22:2812, Dec. 2016.
Shimizu, et al. "Pharmacodynamic Actions of a Long-Acting PTH Analog (LA-PTH) in Thyroparathyroidectomized (TPTX) Rats and Normal Monkeys," *J Bone Miner Res. 31*, No. 7:1405-1412, Jul. 2016.
Suzuki, et al. "High-Level Production of Recombinant Human Parathyroid Hormone 1-34," *Appl Environ Microbiol. 64*, No. 2:526-529, Feb. 1998.
Wilkinson, et al. "A Long-Acting GH Receptor Antagonist through Fusion to GH Binding Protein," *Sci Rep.* 6:1-7, Oct. 2016.
Wilkinson, et al. "MON-537 Fusion of Parathyroid Hormone to Growth Hormone Binding Protein Delays Clearance Whilst Retaining Biological Activity," *J Endocr Soc. 3, Suppl 1*, Apr. 2019.
Wu, et al. "Collagen-Targeting Parathyroid Hormone-Related Peptide Promotes Collagen Binding and In Vitro Chondrogenesis in Bone Marrow-Derived MSCs," *Int J Mol Med. 31*, No. 2:430-436, Feb. 2013.
Great Britain Intellectual Property Office, Combined Search and Examination Report issued in Great Britain Application No. GB1706781.0 dated Feb. 5, 2018 (8 pages).
International Search Report and Written Opinion for PCT/GB2018/051120, dated Dec. 19, 2018 (19 pages).
Kim et al. "Recombinant Human Parathyroid Hormone (1-84): A Review in Hypoparathyroidism," *Drugs*, 75:1293-1303, 2015.
Kostenuik et al. "Infrequent Delivery of a Long-Acting PTH-Fc Fusion Protein Has Potent Anabolic Effects on Cortical and Cancellous Bone," *J Bone Miner Res.*, 22(10):1534-1547, 2007.
Nemeth et al., "Pharmacodynamics of the Type II Calcimimetic Compound Cinacalcet HCl," *J. Pharmacol Exp Ther.*, 308(2):627-635, 2004.
Ghaban et al., Abstract 42, "Development of a long-acting granulocyte colony stimulating factor molecule," *British Journal of Haematology*, vol. 173 (Suppl. 1), pp. 25-26, 2016.

(Continued)

*Primary Examiner* — Elizabeth C. Kemmerer
(74) *Attorney, Agent, or Firm* — Klarquist Sparkman, LLP

(57) ABSTRACT

The disclosure relates to long acting parathyroid or parathyroid hormone like fusion polypeptides comprising a receptor polypeptide and its use in the treatment of hypoparathyroidism and osteoporosis.

18 Claims, 15 Drawing Sheets
Specification includes a Sequence Listing.

(56) References Cited

OTHER PUBLICATIONS

Otsuru and Yamashita, "1. Recent Development of Calcium Metabolic Regulator; 2) Parathyroid hormone-related protein and the effect thereof," *Journal of the Japanese Society of Internal Medicine*, 88(7): 1271-1276, 1999 (with English translation of the abstract).

* cited by examiner

Purified 14A1

SDS-PAGE Analysis: Coomassie stained gel
1. Standards
2. 1 µg protein
3. 2 µg protein
4. 4 µg protein
5. 8 µg protein Purified 14A2b SDS-PAGE Analysis: Coomassie stained gel
1. 10 µg protein
2. Standards

Figure 3

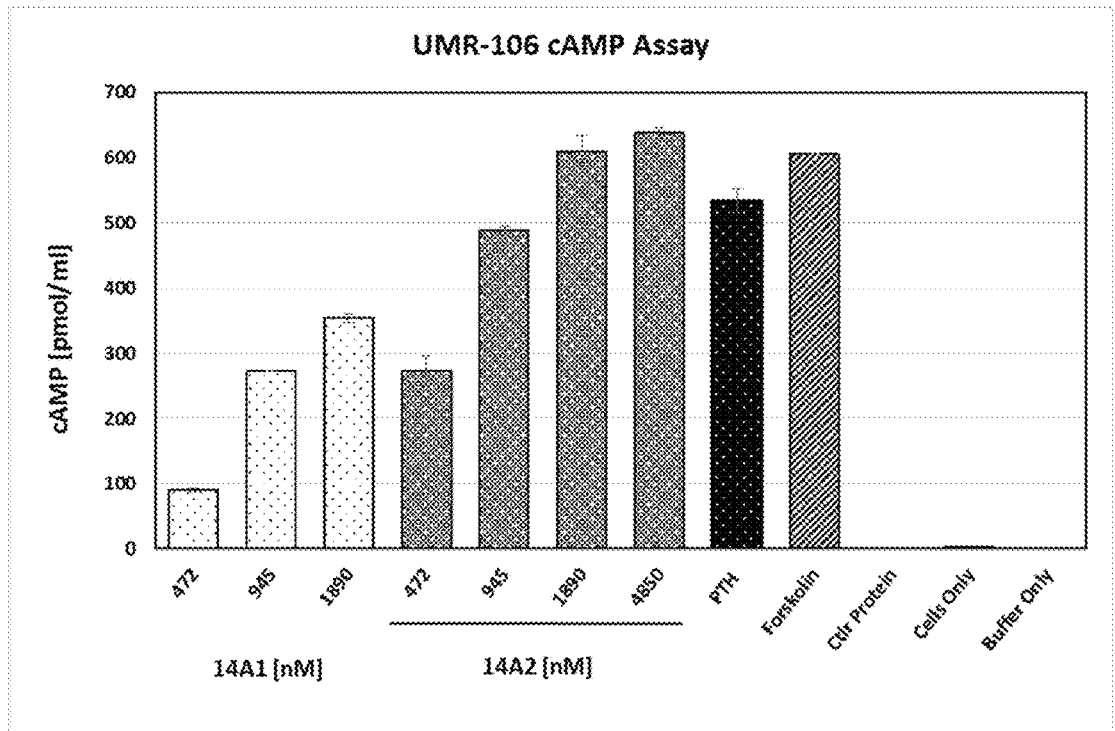

Figure 4A

SEQ ID NO 1, 11 and 9) SEQ ID NO 57
MIPAKDMAKVMIVMLAICFLTKSDG*ksvkkr*SVSEIQLMHNLGKHLNSMERVEWLRKKLQDVHNFVALGAPLAPR
DAGSQRPRKKEDNVLVESHEKSLGEADKADVNVLTKAKSQ

Figure 4B

SEQ ID NO 58
```
  1 AAAAGTCACC ATTTAAGGGG TCTGCAGTCC AATTCATCAG TTGTCTTTAG TTTACTCAGC
 61 ATCAGCTACT AACATACCTG AACGAAGATC TTGTTCTAAG ACATTGTATG TGAAGATGAT
121 ACCTGCAAAA GACATGGCTA AAGTTATGAT TGTCATGTTG CAATTTGTT  TTCTTACAAA
181 ATCGGATGGG aaatctgtta agaagagaTC TGTGAGTGAA ATACAGCTTA TGCATAACCT
241 GGGAAAACAT CTGAACTCGA TGGAGAGAGT AGAATGGCTG CGTAAGAAGC TGCAGGATGT
301 GCACAATTTT GTTGCCCTTG GAGCTCCTCT AGCTCCCAGA GATGCTGGTT CCCAGAGGCC
361 CCGAAAAAAG GAAGACAATG TCTTGGTTGA GAGCCATGAA AAAAGTCTTG GAGAGGCAGA
421 CAAAGCTGAT GTGAATGTAT TAACTAAAGC TAAATCCCAG TGAAAATGAA AACAGATATT
481 GTCAGAGTTC TGCTCTAGAC AGTGTAGGGC AACAATACAT GCTGCTAATT CAAAGCTCTA
541 TTAAGATTTC CAAGTGCCAA TATTTCTGAT ATAACAAACT ACATGTAATC CATCACTAGC
601 CATGATAACT GCAATTTTAA TTGATTATTC TGATTCCACT TTTATTCATT TGAGTTATTT
661 TAATTATCTT TTCTATTGTT TATTCTTTTT AAAGTATGTT ATTGCATAAT TTATAAAAGA
721 ATAAAATTGC ACTTTTAAAC CTCTCTTCTA CCTTAAAATG TAAAACAAAA ATGTAATGAT
781 CATAAGTCTA AATAAATGAA GTATTTCTCA CTCATTGCAA GTAAAAAAAA AAAA
```

Figure 5A

SEQ ID No 54   SVSEIQLMHNLGKHLNSMERVEWLRKKLQDVHNF

Figure 5B

SEQ ID NO 59
TCTGTGAGTGAAATACAGCTTATGCATAACCTGGGAAAACATCTGAACTCGATGGAGAGAGTAGAATGGCTGCGT
AAGAAGCTGCAGGATGTGCACAATTTT

Figure 5C
SEQ ID NO 1 and SEQ ID NO 11) SEQ ID NO 60  MIPAKDMAKVMIVMLAICFLTKSDG*ksvkkr*

Figure 5D
SEQ ID NO 61
ATGATACCTGCAAAAGACATGGCTAAAGTTATGATTGTCATGTTGGCAATTTGTTTTCTTACAAAATCGGATGGG
*aaatctgttaagaagagatc*

Figure 6A
SEQ ID NO 56
MGTARIAPGLALLLCCPVLSSAYALVDA**DDVMTKEEQIFLLHRAQAQCEKRLKEVLQRPASIMESDKGWTSASTS
GKPRKDKASGKLYPESEEDKEAPTGSRYRGRPCLPEWDHILCWPLGAPGEVVAVPCPDYIYDFNHKGHAYRRCDR
NGSWELVPGHNRTWANYSECVKFLTNETREREVFDRL**GMIYTVGYSVSLASLTVAVLILAYFRRLHCTRNYIHMH
LFLSFMLRAVSIFVKDAVLYSGATLDEAERLTEEELRAIAQAPPPPATAAAGYAGCRVAVTFFLYFLATNYYWIL
VEGLYLRSLIFMAFFSEKKYLWGFTVFGWGLPAVFVAVWVSVRATLANTGCWDLSSGNKKWIIQVPILASIVLNF
ILFINIVRVLATKLRETNAGRCDTRQQYRKLLKSTLVLMPLFGVHYIVFMATPYTEVSGTLWQVQMHYEMLFNSF
QGFFVAIIYCFCNGEVQAEIKKSWSRWTLALDFKRKARSGSSSYSYGPMVSHTSVTNVGPRVGLGLPLSPRLLPT
ATTNGHPQLPGHAKPGTPALETLETTPPAMAAPKDDGFLNGSCSGLDEEASGPERPPALLQEEWETVM

Figure 6B
SEQ ID NO 62
```
   1 GGAGCGGCAG ACGCCGAGGG CCGGCGGCGG CGGCTGCCCC GAGGGACGCG GCCCTAGGCG
  61 GTGGCGATGG GGACCGCCCG GATCGCACCC GGCCTGGCGC TCCTGCTCTG CTGCCCCGTG
 121 CTCAGCTCCG CGTACGCGCT GGTGGATGCA GATGACGTCA TGACTAAAGA GGAACAGATC
 181 TTCCTGCTGC ACCGTGCTCA GGCCCAGTGC GAAAAACGGC TCAAGGAGGT CCTGCAGAGG
 241 CCAGCCAGCA TAATGGAATC AGACAAGGGA TGGACATCTG CGTCCACATC AGGGAAGCCC
 301 AGGAAAGATA AGGCATCTGG GAAGCTCTAC CCTGAGTCTG AGGAGGACAA GGAGGCACCC
 361 ACTGGCAGCA GGTACCGAGG CGCCCCTGT CTGCCGGAAT GGACCACAT CCTGTGCTGG
 421 CCGCTGGGGG CACCAGGTGA GGTGGTGGCT GTGCCCTGTC CGGACTACAT TTATGACTTC
 481 AATCACAAAG GCCATGCCTA CCGACGCTGT GACCGCAATG GCAGCTGGGA GCTGGTGCCT
 541 GGGCACAACA GGACGTGGGC CAACTACAGC GAGTGTGTCA AATTTCTCAC CAATGAGACT
 601 CGTGAACGGG AGGTGTTTGA CCGCCTGGGC ATGATTTACA CCGTGGGCTA CTCCGTGTCC
 661 CTGGCGTCCC TCACCGTAGC TGTGCTCATC CTGGCCTACT TTAGGCGGCT GCACTGCACG
 721 CGCAACTACA TCCACATGCA CCTGTTCCTG TCCTTCATGC TGCGCGCCGT GAGCATCTTC
 781 GTCAAGGACG CTGTGCTCTA CTCTGGCGCC ACGCTTGATG AGGCTGAGCG CCTCACCGAG
 841 GAGGAGCTGC GCGCCATCGC CCAGGCGCCC CGCCGCCTG CCACCGCCGC TGCCGGCTAC
 901 GCGGGCTGCA GGGTGGCTGT GACCTTCTTC CTTTACTTCC TGGCCACCAA CTACTACTGG
 961 ATTCTGGTGG AGGGGCTGTA CCTGCACAGC CTCATCTTCA TGGCCTTCTT CTCAGAGAAG
1021 AAGTACCTGT GGGGCTTCAC AGTCTTCGGC TGGGGTCTGC CCGCTGTCTT CGTGGCTGTG
1081 TGGGTCAGTG TCAGAGCTAC CCTGGCCAAC ACCGGGTGCT GGGACTTGAG CTCCGGGAAC
1141 AAAAAGTGGA TCATCCAGGT GCCCATCCTG GCCTCCATTG TGCTCAACTT CATCCTCTTC
1201 ATCAATATCG TCCGGGTGCT CGCCACCAAG CTGCGGGAGA CCAACGCCGG CCGGTGTGAC
1261 ACACGGCAGC AGTACCGGAA GCTGCTCAAA TCCACGCTGG TGCTCATGCC CCTCTTTGGC
1321 GTCCACTACA TTGTCTTCAT GGCCACACCA TACACCGAGG TCTCAGGGAC GCTCTGGCAA
1381 GTCCAGATGC ACTATGAGAT GCTCTTCAAC TCCTTCCAGG GATTTTTTGT CGCAATCATA
1441 TACTGTTTCT GCAATGGCGA GGTACAAGCT GAGATCAAGA AATCTTGGAG CCGCTGGACA
1501 CTGGCACTGG ACTTCAAGCG AAAGGCACGC AGCGGGAGCA GCAGCTATAG CTACGGCCCC
1561 ATGGTGTCCC ACACAAGTGT GACCAATGTC GGCCCCGTG TGGGACTCGG CCTGCCCCTC
1621 AGCCCCGCC TACTGCCCAC TGCCACCACC AACGCCACC CTCAGCTGCC TGGCCATGCC
1681 AAGCCAGGGA CCCCAGCCCT GGAGACCCTC GAGACCACAC CACCTGCCAT GGCTGCTCCC
1741 AAGGACGATG GGTTCCTCAA CGGCTCCTGC TCAGGCCTGG ACGAGGAGGC CTCTGGGCCT
1801 GAGCGGCCAC CTGCCCTGCT ACAGGAAGAG TGGGAGACAG TCATGTGACC AGGCGCTGGG
1861 GGCTGGACCT GCTGACATAG TGGATGGACA GATGGACCAA AAGATGGGTG TTGAATGAT
1921 TTCCCACTCA GGGCTGGGGC CAAGAGGAAA AACAGGGAAA AAAGAAAAA AAAAAGAAAA
1981 AGGAAAAGGA AAAAAAAAAA AAAAAAA
```

Figure 7A (SEQ ID NO 3)
DDVMTKEEQIFLLHRAQAQCEKRLKEVLQRPASIMESDKGWTSASTSGKPRKDKASGKLYPESEEDKEAPTGSRY
R
GRPCLPEWDHILCWPLGAPGEVVAVPCPDYIYDFNHKGHAYRRCDRNGSWELVPGHNRTWANYSECVKFLTNETR
E
REVFDRL

Figure 7B
SEQ ID NO 63
```
GATGACGTCA TGACTAAAGA GGAACAGATC TTCCTGCTGC ACCGTGCTCA GGCCCAGTGC GAAAACGGC
TCAAGGAGGT CCTGCAGAGG CCAGCCAGCA TAATGGAATC AGACAAGGGA TGGACATCTG CGTCCACATC
AGGGAAGCCC AGGAAAGATA AGGCATCTGG GAAGCTCTAC CCTGAGTCTG AGGAGGACAA GGAGGCACCC
ACTGGCAGCA GGTACCGAGG GCGCCCTGT CTGCCGGAAT GGGACCACAT CCTGTGCTGG CCGCTGGGGG
CACCAGGTGA GGTGGTGGCT GTGCCCTGTC CGGACTACAT TTATGACTTC AATCACAAAG GCCATGCCTA
CCGACGCTGT GACCGCAATG GCAGCTGGGA GCTGGTGCCT GGGCACAACA GGACGTGGGC CAACTACAGC
GAGTGTGTCA AATTTCTCAC CAATGAGACT CGTGAACGGG AGGTGTTTGA CCGCCTG
```

Figure 8A
SEQ ID NO 64
```
TTTTCTGGAAGTGAGGCCACAGCAGCTATCCTTAGCAGAGCACCCTGGAGTCTGCAAAGTGTTAATCCAGGCCTA
AAGACAAATTCTTCTAAGGAGCCTAAATTCACCAAGTGCCGTTCACCTGAGCGAGAGACTTTTTCATGCCACTGG
ACAGATGAGGTTCATCATGGTACAAAGAACCTAGGACCCATACAGCTGTTCTATACCAGAAGGAACACTCAAGAA
TGGACTCAAGAATGGAAAGAATGCCCTGATTATGTTTCTGCTGGGGAAAACAGCTGTTACTTTAATTCATCGTTT
ACCTCCATCGCAATACCTTATTGTATCAAGCTAACTAGCAATGGTGGTACAGTGGATGAAAAGTGTTTCTCTGTT
GATGAAATAGTGCAACCAGATCCACCCATTGCCCTCAACTGGACTTTACTGAACGTCAGTTTAACTGGGATTCAT
GCAGATATCCAAGTGAGATGGGAAGCACCACGCAATGCAGATATTCAGAAAGGATGGATGGTTCTGGAGTATGAA
CTTCAATACAAAGAAGTAAATGAAACTAAATGGAAAATGATGGACCCTATATTGACAACATCAGTTCCAGTGTAC
TCATTGAAAGTGGATAAGGAATATGAAGTGCGTGTGAGATCCAAACAACGAAACTCTGGAAATTATGGCGAGTTC
AGTGAGGTGCTCTATGTAACACTTCCTCAGATGAGCCAA
```

Figure 8B
SEQ ID NO 7)
```
FSGSEATAAILSRAPWSLQSVNPGLKTNSSKEPKFTKCRSPERETFSCHWTDEVHHGTKNLGPIQLFYTRRNTQE
WTQEWKECPDYVSAGENSCYFNSSFTSIAIPYCIKLTSNGGTVDEKCFSVDEIVQPDPPIALNWTLLNVSLTGIH
ADIQVRWEAPRNADIQKGWMVLEYELQYKEVNETKWKMMDPILTTSVPVYSLKVDKEYEVRVRSKQRNSGNYGEF
SEVLYVTLPQMSQ
```

Figure 9A
SEQ ID NO 2)
MATGSRTSLLLAFGLLCLPWLQEGSA

Figure 9B
SEQ ID NO 65
```
ATGGCTACAGGCTCCCGGACGTCCCTGCTCCTGGCTTTTGGCCTGCTCTGCCTGCCCTGGCTTCAAGAGGGCAGT
GCC
```

Figure 10A
SEQ ID NO 66
```
atgatacctgcaaaagacatggctaaagttatgattgtcatgttggcaatttgttttcttacaaaatcggatggg
TCTGTGAGTGAAATACAGCTTATGCATAACCTGGGAAAACATCTGAACTCGATGGAGAGAGTAGAATGGCTGCGT
AAGAAGCTGCAGGATGTGCACAATTTTGGTGGCGGAGGTAGTGGTGGCGGAGGTAGCGGTGGCGGAGGTTCTGGT
GGCGGAGGTTCCgatgacgtcatgactaaagaggaacagatcttcctgctgcaccgtgctcaggcccagtgcgaa
aaacggctcaaggaggtcctgcagaggccagccagcataatggaatcagacaagggatggacatctgcgtccaca
tcagggaagcccaggaaagataaggcatctgggaagctctaccctgagtctgaggaggacaaggaggcaccact
ggcagcaggtaccgagggcgcccctgtctgccggaatgggaccacatcctgtgctggccgctgggggcaccaggt
gaggtggtggctgtgccctgtccggactacatttatgacttcaatcacaaaggccatgcctaccgacgctgtgac
cgcaatggcagctgggagctggtgcctgggcacaacaggacgtgggccaactacagcgagtgtgtcaaatttctc
accaatgagactcgtgaacgggaggtgtttgaccgcctgGGTGGCGGAGGTAGTGGTGGCGGAGGTAGCGGTGGC
GGAGGTTCTGGTGGCGGAGGTTCCTTTTCTGGAAGTGAGGCCACAGCAGCTATCCTTAGCAGAGCACCCTGGAGT
CTGCAAAGTGTTAATCCAGGCCTAAAGACAAATTCTTCTAAGGAGCCTAAATTCACCAAGTGCCGTTCACCTGAG
CGAGAGACTTTTTCATGCCACTGGACAGATGAGGTTCATCATGGTACAAAGAACCTAGGACCCATACAGCTGTTC
TATACCAGAAGGAACACTCAAGAATGGACTCAAGAATGGAAAGAATGCCCTGATTATGTTTCTGCTGGGGAAAAC
AGCTGTTACTTTAATTCATCGTTTACCTCCATCGCAATACCTTATTGTATCAAGCTAACTAGCAATGGTGGTACA
GTGGATGAAAAGTGTTTCTCTGTTGATGAAATAGTGCAACCAGATCCACCCATTGCCCTCAACTGGACTTTACTG
AACGTCAGTTTAACTGGGATTCATGCAGATATCCAAGTGAGATGGGAAGCACCACGCAATGCAGATATTCAGAAA
GGATGGATGGTTCTGGAGTATGAACTTCAATACAAAGAAGTAAATGAAACTAAATGGAAAATGATGGACCCTATA
TTGACAACATCAGTTCCAGTGTACTCATTGAAAGTGGATAAGGAATATGAAGTGCGTGTGAGATCCAAACAACGA
AACTCTGGAAATTATGGCGAGTTCAGTGAGGTGCTCTATGTAACACTTCCTCAGATGAGCCAA*
```

Figure 10B

SEQ ID NO 12 mipakdmakvmivmlaicfltksdg<u>SVSEIQLMHNLGKHLNSMERVEWLRKKLQDVHNF</u>**GGGGSGGGGSGGGGSG
GGGS**ddvmtkeeqifllhraqaqcekrlkevlqrpasimesdkgwtsastsgkprkdkasgklypeseedkeapt
gsryrgrpclpewdhilcwplgapgevvavpcpdyiydfnhkghayrrcdrngswelvpghnrtwanysecvkfl
tnetrerevfdrlGGGGSGGGGSGGGGSGGGGSFSGSEATAAILSRAPWSLQSVNPGLKTNSSKEPKFTKCRSPE
RETFSCHWTDEVHHGTKNLGPIQLFYTRRNTQEWTQEWKECPDYVSAGENSCYFNSSFTSIAIPYCIKLTSNGGT
VDEKCFSVDEIVQPDPPIALNWTLLNVSLTGIHADIQVRWEAPRNADIQKGWMVLEYELQYKEVNETKWKMMDPI
LTTSVPVYSLKVDKEYEVRVRSKQRNSGNYGEFSEVLYVTLPQMSQ*

Figure 11A

SEQ ID NO 67 atgatacctgcaaaagacatggctaaagttatgattgtcatgttggcaatttgttttcttacaaaatcggatggg
aaatctgttaagaagaga<u>TCTGTGAGTGAAATACAGCTTATGCATAACCTGGGAAAACATCTGAACTCGATGGAG
AGAGTAGAATGGCTGCGTAAGAAGCTGCAGGATGTGCACAATTTT</u>**GGTGGCGGAGGTAGTGGTGGCGGAGGTAGC
GGTGGCGGAGGTTCTGGTGGCGGAGGTTCC**gatgacgtcatgactaaagaggaacagatcttcctgctgcaccgt
gctcaggcccagtgcgaaaaacggctcaaggaggtcctgcagaggccagccagcataatggaatcagacaaggga
tggacatctgcgtccacatcagggaagcccaggaaagataaggcatctgggaagctctaccctgagtctgaggag
gacaaggaggcacccactggcagcaggtaccgagggcgcccctgtctgccggaatgggaccacatcctgtgctgg
ccgctggggcaccaggtgaggtggtggctgtgccctgtccggactacatttatgacttcaatcacaaaggccat
gcctaccgacgctgtgaccgcaatggcagctgggagctggtgcctgggcacaacaggacgtgggccaactacagc
gagtgtgtcaaatttctcaccaatgagactcgtgaacgggaggtgtttgaccgcctg**GGTGGCGGAGGTAGTGGT
GGCGGAGGTAGCGGTGGCGGAGGTTCTGGTGGCGGAGGTTCC**TTTTCTGGAAGTGAGGCCACAGCAGCTATCCTT
AGCAGAGCACCCTGGAGTCTGCAAAGTGTTAATCCAGGCCTAAAGACAAATTCTTCTAAGGAGCCTAAATTCACC
AAGTGCCGTTCACCTGAGCGAGAGACTTTTTCATGCCACTGGACAGATGAGGTTCATCATGGTACAAAGAACCTA
GGACCCATACAGCTGTTCTATACCAGAAGGAACACTCAAGAATGGACTCAAGAATGGAAAGAATGCCCTGATTAT
GTTTCTGCTGGGGAAAACAGCTGTTACTTTAATTCATCGTTTACCTCCATCGCAATACCTTATTGTATCAAGCTA
ACTAGCAATGGTGGTACAGTGGATGAAAGTGTTTCTCTGTTGATGAAATAGTGCAACCAGATCCACCCATTGCC
CTCAACTGGACTTTACTGAACGTCAGTTTAACTGGGATTCATGCAGATATCCAAGTGAGATGGGAAGCACCACGC
AATGCAGATATTCAGAAAGGATGGATGGTTCTGGAGTATGAACTTCAATACAAAGAAGTAAATGAAACTAAATGG
AAAATGATGGACCCTATATTGACAACATCAGTTCCAGTGTACTCATTGAAAGTGGATAAGGAATATGAAGTGCGT
GTGAGATCCAAACAACGAAACTCTGGAAATTATGGCGAGTTCAGTGAGGTGCTCTATGTAACACTTCCTCAGATG
AGCCAA*

Figure 11B

SEQ ID NO 13 mipakdmakvmivmlaicfltksdgksvkkr<u>SVSEIQLMHNLGKHLNSMERVEWLRKKLQDVHNF</u>**GGGGSGGGGS
GGGGSGGGGS**ddvmtkeeqifllhraqaqcekrlkevlqrpasimesdkgwtsastsgkprkdkasgklypesee
dkeaptgsryrgrpclpewdhilcwplgapgevvavpcpdyiydfnhkghayrrcdrngswelvpghnrtwanys
ecvkfltnetrerevfdrlGGGGSGGGGSGGGGSGGGGSFSGSEATAAILSRAPWSLQSVNPGLKTNSSKEPKFT
KCRSPERETFSCHWTDEVHHGTKNLGPIQLFYTRRNTQEWTQEWKECPDYVSAGENSCYFNSSFTSIAIPYCIKL
TSNGGTVDEKCFSVDEIVQPDPPIALNWTLLNVSLTGIHADIQVRWEAPRNADIQKGWMVLEYELQYKEVNETKW
KMMDPILTTSVPVYSLKVDKEYEVRVRSKQRNSGNYGEFSEVLYVTLPQMSQ*

Figure 12A

SEQ ID NO 68 atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTT**GGTGGCGGAGGTAGTGGTGGCGGAGGTAGCGGTGGCGGAGGTTCT
GGTGGCGGAGGTTCC**gatgacgtcatgactaaagaggaacagatcttcctgctgcaccgtgctcaggcccagtgc
gaaaaacggctcaaggaggtcctgcagaggccagccagcataatggaatcagacaagggatggacatctgcgtcc
acatcagggaagcccaggaaagataaggcatctgggaagctctaccctgagtctgaggaggacaaggaggcaccc
actggcagcaggtaccgagggcgccctgtctgccggaatgggaccacatcctgtgctggccgctgggggcacca
ggtgaggtggtggctgtgccctgtccggactacatttatgacttcaatcacaaaggccatgcctaccgacgctgt
gaccgcaatggcagctgggagctggtgcctgggcacaacaggacgtgggccaactacagcgagtgtgtcaaattt
ctcaccaatgagactcgtgaacgggaggtgtttgaccgcctg**GGTGGCGGAGGTAGTGGTGGCGGAGGTAGCGGT
GGCGGAGGTTCTGGTGGCGGAGGTTCC**TTTTCTGGAAGTGAGGCCACAGCAGCTATCCTTAGCAGAGCACCCTGG
AGTCTGCAAAGTGTTAATCCAGGCCTAAAGACAAATTCTTCTAAGGAGCCTAAATTCACCAAGTGCCGTTCACCT
GAGCGAGAGACTTTTTCATGCCACTGGACAGATGAGGTTCATCATGGTACAAAGAACCTAGGACCCATACAGCTG
TTCTATACCAGAAGGAACACTCAAGAATGGACTCAAGAATGGAAAGAATGCCCTGATTATGTTTCTGCTGGGGAA
AACAGCTGTTACTTTAATTCATCGTTTACCTCCATCGCAATACCTTATTGTATCAAGCTAACTAGCAATGGTGGT
ACAGTGGATGAAAAGTGTTTCTCTGTTGATGAAATAGTGCAACCAGATCCACCCATTGCCCTCAACTGGACTTTA
CTGAACGTCAGTTTAACTGGGATTCATGCAGATATCCAAGTGAGATGGGAAGCACCACGCAATGCAGATATTCAG
AAAGGATGGATGGTTCTGGAGTATGAACTTCAATACAAAGAAGTAAATGAAACTAAATGGAAAATGATGGACCCT
ATATTGACAACATCAGTTCCAGTGTACTCATTGAAAGTGGATAAGGAATATGAAGTGCGTGTGAGATCCAAACAA
CGAAACTCTGGAAATTATGGCGAGTTCAGTGAGGTGCTCTATGTAACACTTCCTCAGATGAGCCAA*

Figure 12B

SEQ ID NO 14 matgsrtslllafgllclpwlqegsa<u>SVSEIQLMHNLGKHLNSMERVEWLRKKLQDVHNF</u>**GGGGSGGGGSGGGGS
GGGGS**ddvmtkeeqifllhraqaqcekrlkevlqrpasimesdkgwtsastsgkprkdkasgklypeseedkeap
tgsryrgrpclpewdhilcwplgapgevvavpcpdyiydfnhkghayrrcdrngswelvpghnrtwanysecvkf
ltnetrerevfdrlGGGGSGGGGSGGGGSGGGGSFSGSEATAAILSRAPWSLQSVNPGLKTNSSKEPKFTKCRSP
ERETFSCHWTDEVHHGTKNLGPIQLFYTRRNTQEWTQEWKECPDYVSAGENSCYFNSSFTSIAIPYCIKLTSNGG
TVDEKCFSVDEIVQPDPPIALNWTLLNVSLTGIHADIQVRWEAPRNADIQKGWMVLEYELQYKEVNETKWKMMDP
ILTTSVPVYSLKVDKEYEVRVRSKQRNSGNYGEFSEVLYVTLPQMSQ*

Figure 13A

SEQ ID NO 69 atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTT**GGTGGCGGAGGTAGTGGTGGCGGAGGTAGCGGTGGCGGAGGTTCT
GGTGGCGGAGGTTCC**TTTTCTGGAAGTGAGGCCACAGCAGCTATCCTTAGCAGAGCACCCTGGAGTCTGCAAAGT
GTTAATCCAGGCCTAAAGACAAATTCTTCTAAGGAGCCTAAATTCACCAAGTGCCGTTCACCTGAGCGAGAGACT
TTTTCATGCCACTGGACAGATGAGGTTCATCATGGTACAAAGAACCTAGGACCCATACAGCTGTTCTATACCAGA
AGGAACACTCAAGAATGGACTCAAGAATGGAAAGAATGCCCTGATTATGTTTCTGCTGGGGAAAACAGCTGTTAC
TTTAATTCATCGTTTACCTCCATCGCAATACCTTATTGTATCAAGCTAACTAGCAATGGTGGTACAGTGGATGAA
AAGTGTTTCTCTGTTGATGAAATAGTGCAACCAGATCCACCCATTGCCCTCAACTGGACTTTACTGAACGTCAGT
TTAACTGGGATTCATGCAGATATCCAAGTGAGATGGGAAGCACCACGCAATGCAGATATTCAGAAAGGATGGATG
GTTCTGGAGTATGAACTTCAATACAAAGAAGTAAATGAAACTAAATGGAAAATGATGGACCCTATATTGACAACA
TCAGTTCCAGTGTACTCATTGAAAGTGGATAAGGAATATGAAGTGCGTGTGAGATCCAAACAACGAAACTCTGGA
AATTATGGCGAGTTCAGTGAGGTGCTCTATGTAACACTTCCTCAGATGAGCCAAtaaaagctt*

Figure 13B

SEQ ID NO 15 matgsrtslllafgllclpwlqegsa<u>SVSEIQLMHNLGKHLNSMERVEWLRKKLQDVHNF</u>**GGGGSGGGGSGGGGS
GGGGS**FSGSEATAAILSRAPWSLQSVNPGLKTNSSKEPKFTKCRSPERETFSCHWTDEVHHGTKNLGPIQLFYTR
RNTQEWTQEWKECPDYVSAGENSCYFNSSFTSIAIPYCIKLTSNGGTVDEKCFSVDEIVQPDPPIALNWTLLNVS
LTGIHADIQVRWEAPRNADIQKGWMVLEYELQYKEVNETKWKMMDPILTTSVPVYSLKVDKEYEVRVRSKQRNSG
NYGEFSEVLYVTLPQMSQ*

Figure 14A

SEQ ID NO 70 atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTTGGTGGCGGAGGTAGTGGTGGCGGAGGTAGCGGTGGCGGAGGTTCT
GGTGGCGGAGGTTCCgatgacgtcatgactaaagaggaacagatcttcctgctgcaccgtgctcaggcccagtgc
gaaaaacggctcaaggaggtcctgcagaggccagccagcataatggaatcagacaagggatggacatctgcgtcc
acatcagggaagcccaggaaagataaggcatctgggaagctctaccctgagtctgaggaggacaaggaggcaccc
actggcagcaggtaccgagggcgccctgtctgccggaatgggaccacatcctgtgctggccgctgggggcacca
ggtgaggtggtggctgtgccctgtccggactacatttatgacttcaatcacaaaggccatgcctaccgacgctgt
gaccgcaatggcagctgggagctggtgcctgggcacaacaggacgtgggccaactacagcgagtgtgtcaaattt
ctcaccaatgagactcgtgaacgggaggtgtttgaccgcctg
accggtCATCATCACCATCACCAT*

Figure 14B

SEQ ID NO 17 matgsrtslllafgllclpwlqegsaSVSEIQLMHNLGKHLNSMERVEWLRKKLQDVHNFGGGGSGGGGSGGGGS
GGGGSddvmtkeeqifllhraqaqcekrlkevlqrpasimesdkgwtsastsgkprkdkasgklypeseedkeap
tgsryrgrpclpewdhilcwplgapgevvavpcpdyiydfnhkghayrrcdrngswelvpghnrtwanysecvkf
ltnetrerevfdrlTGHHHHHH*

Figure 15A

SEQ ID NO 71 atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTTGGTGGCGGAGGTAGTGGTGGCGGAGGTAGCGGTGGCGGAGGTTCT
GGTGGCGGAGGTTCCgatgacgtcatgactaaagaggaacagatcttcctgctgcaccgtgctcaggcccagtgc
gaaaaacggctcaaggaggtcctgcagaggccagccagcataatggaatcagacaagggatggacatctgcgtcc
acatcagggaagcccaggaaagataaggcatctgggaagctctaccctgagtctgaggaggacaaggaggcaccc
actggcagcaggtaccgagggcgccctgtctgccggaatgggaccacatcctgtgctggccgctgggggcacca
ggtgaggtggtggctgtgccctgtccggactacatttatgacttcaatcacaaaggccatgcctaccgacgctgt
gaccgcaatggcagctgggagctggtgcctgggcacaacaggacgtgggccaactacagcgagtgtgtcaaattt
ctcaccaatgagactcgtgaacgggaggtgtttgaccgcctg*

Figure 15B

(SEQ ID NO 16)

matgsrtslllafgllclpwlqegsaSVSEIQLMHNLGKHLNSMERVEWLRKKLQDVHNFGGGGSGGGGSGGGGS
GGGGSddvmtkeeqifllhraqaqcekrlkevlqrpasimesdkgwtsastsgkprkdkasgklypeseedkeap
tgsryrgrpclpewdhilcwplgapgevvavpcpdyiydfnhkghayrrcdrngswelvpghnrtwanysecvkf
ltnetrerevfdrl*

Figure 16A

SEQ ID NO 72 atgatacctgcaaaagacatggctaaagttatgattgtcatgttggcaatttgttttcttacaaaatcggatggg
aaatctgttaagaagagaTCTGTGAGTGAAATACAGCTTATGCATAACCTGGGAAAACATCTGAACTCGATGGAG
AGAGTAGAATGGCTGCGTAAGAAGCTGCAGGATGTGCACAATTTTGGTGGCGGAGGTAGTGGTGGCGGAGGTAGC
GGTGGCGGAGGTTCTGGTGGCGGAGGTTCCgatgacgtcatgactaaagaggaacagatcttcctgctgcaccgt
gctcaggcccagtgcgaaaaacggctcaaggaggtcctgcagaggccagccagcataatggaatcagacaaggga
tggacatctgcgtccacatcagggaagcccaggaaagataaggcatctgggaagctctaccctgagtctgaggag
gacaaggaggcacccactggcagcaggtaccgagggcgccctgtctgccggaatgggaccacatcctgtgctgg
ccgctgggggcaccaggtgaggtggtggctgtgccctgtccggactacatttatgacttcaatcacaaaggccat
gcctaccgacgctgtgaccgcaatggcagctgggagctggtgcctgggcacaacaggacgtgggccaactacagc
gagtgtgtcaaatttctcaccaatgagactcgtgaacgggaggtgtttgaccgcctgaccggtCATCATCACCAT
CACCAT*

Figure 16B
SEQ ID NO 18
mipakdmakvmivmlaicfltksdgksvkkrSVSEIQLMHNLGKHLNSMERVEWLRKKLQDVHNFGGGGSGGGGS
GGGGSGGGGSddvmtkeeqifllhraqaqcekrlkevlqrpasimesdkgwtsastsgkprkdkasgklypesee
dkeaptgsryrgrpclpewdhilcwplgapgevvavpcpdyiydfnhkghayrrcdrngswelvpghnrtwanys
ecvkfltnetrerevfdrlTGHHHHHH*

Figure 17A
SEQ ID NO 73
atgatacctgcaaaagacatggctaaagttatgattgtcatgttggcaatttgttttcttacaaaatcggatggg
aaatctgttaagaagagaTCTGTGAGTGAAATACAGCTTATGCATAACCTGGGAAAACATCTGAACTCGATGGAG
AGAGTAGAATGGCTGCGTAAGAAGCTGCAGGATGTGCACAATTTTGGTGGCGGAGGTAGTGGTGGCGGAGGTAGC
GGTGGCGGAGGTTCTGGTGGCGGAGGTTCCgatgacgtcatgactaaagaggaacagatcttcctgctgcaccgt
gctcaggcccagtgcgaaaaacggctcaaggaggtcctgcagaggccagccagcataatggaatcagacaaggga
tggacatctgcgtccacatcagggaagcccaggaagataaggcatctgggaagctctaccctgagtctgaggag
gacaaggaggcacccactggcagcaggtaccgagggcgccctgtctgccggaatgggaccacatcctgtgctgg
ccgctgggggcaccaggtgaggtggtggctgtgccctgtccggactacatttatgacttcatcacaaaggccat
gcctaccgacgctgtgaccgcaatggcagctgggagctggtgcctgggcacaacaggacgtgggccaactacagc
gagtgtgtcaaatttctcaccaatgagactcgtgaacgggaggtgtttgaccgcctg*

Figure 17B
SEQ ID NO 19
mipakdmakvmivmlaicfltksdgksvkkrSVSEIQLMHNLGKHLNSMERVEWLRKKLQDVHNFGGGGSGGGGS
GGGGSGGGGSddvmtkeeqifllhraqaqcekrlkevlqrpasimesdkgwtsastsgkprkdkasgklypesee
dkeaptgsryrgrpclpewdhilcwplgapgevvavpcpdyiydfnhkghayrrcdrngswelvpghnrtwanys
ecvkfltnetrerevfdrl*

Figure 18A
SEQ ID NO 74
atgatacctgcaaaagacatggctaaagttatgattgtcatgttggcaatttgttttcttacaaaatcggatggg
aaatctgttaagaagagaTCTGTGAGTGAAATACAGCTTATGCATAACCTGGGAAAACATCTGAACTCGATGGAG
AGAGTAGAATGGCTGCGTAAGAAGCTGCAGGATGTGCACAATTTTGGTGGCGGAGGTAGTGGTGGCGGAGGTAGC
GGTGGCGGAGGTTCTGGTGGCGGAGGTTCCTTTTCTGGAAGTGAGGCCACAGCAGCTATCCTTAGCAGAGCACCC
TGGAGTCTGCAAAGTGTTAATCCAGGCCTAAAGACAAATTCTTCTAAGGAGCCTAAATTCACCAAGTGCCGTTCA
CCTGAGCGAGAGACTTTTTCATGCCACTGGACAGATGAGGTTCATCATGGTACAAAGAACCTAGGACCCATACAG
CTGTTCTATACCAGAAGGAACACTCAAGAATGGACTCAAGAATGGAAAGAATGCCCTGATTATGTTTCTGCTGGG
GAAAACAGCTGTTACTTTAATTCATCGTTTACCTCCATCGCAATACCTTATTGTATCAAGCTAACTAGCAATGGT
GGTACAGTGGATGAAAAGTGTTTCTCTGTTGATGAAATAGTGCAACCAGATCCACCCATTGCCCTCAACTGGACT
TTACTGAACGTCAGTTTAACTGGGATTCATGCAGATATCCAAGTGAGATGGGAAGCACCACGCAATGCAGATATT
CAGAAGGATGGATGGTTCTGGAGTATGAACTTCAATACAAAGAAGTAAATGAAACTAAATGGAAAATGATGGAC
CCTATATTGACAACATCAGTTCCAGTGTACTCATTGAAAGTGGATAAGGAATATGAAGTGCGTGTGAGATCCAAA
CAACGAAACTCTGGAAATTATGGCGAGTTCAGTGAGGTGCTCTATGTAACACTTCCTCAGATGAGCCAA*

Figure 18B
SEQ ID NO 20
mipakdmakvmivmlaicfltksdgksvkkrSVSEIQLMHNLGKHLNSMERVEWLRKKLQDVHNFGGGGSGGGGS
GGGGSGGGGSFSGSEATAAILSRAPWSLQSVNPGLKTNSSKEPKFTKCRSPERETFSCHWTDEVHHGTKNLGPIQ
LFYTRRNTQEWTQEWKECPDYVSAGENSCYFNSSFTSIAIPYCIKLTSNGGTVDEKCFSVDEIVQPDPPIALNWT
LLNVSLTGIHADIQVRWEAPRNADIQKGWMVLEYELQYKEVNETKWKMMDPILTTSVPVYSLKVDKEYEVRVRSK
QRNSGNYGEFSEVLYVTLPQMSQ*

Figure 19A

SEQ ID NO 75 atgatacctgcaaaagacatggctaaagttatgattgtcatgttggcaatttgttttcttacaaaatcggatggg
aaatctgttaagaagagaTCTGTGAGTGAAATACAGCTTATGCATAACCTGGGAAAACATCTGAACTCGATGGAG
AGAGTAGAATGGCTGCGTAAGAAGCTGCAGGATGTGCACAATTTT**GGTGGCGGAGGTAGTGGTGGCGGAGGTAGC
GGTGGCGGAGGTTCTGGTGGCGGAGGTTCC**gatgacgtcatgactaaagaggaacagatcttcctgctgcaccgt
gctcaggcccagtgcgaaaaacggctcaaggaggtcctgcagaggccagccagcataatggaatcagacaaggga
tggacatctgcgtccacatcagggaagcccaggaaagataaggcatctgggaagctctaccctgagtctgaggag
gacaaggaggcacccactggcagcaggtaccgagggcgccctgtctgccggaatgggaccacatcctgtgctgg
ccgctgggggcaccaggtgaggtggtggctgtgccctgtccggactacaagtatgacttcaatcacaaaggccat
gcctaccgacgctgtgaccgcaatggcagctgggagctggtgcctgggcacaacaggacgtgggccaactacagc
gagtgtgtcaaatttctcaccaatgagactcgtgaacgggaggtgtttgaccgcctg**GGTGGCGGAGGTAGTGGT
GGCGGAGGTAGCGGTGGCGGAGGTTCTGGTGGCGGAGGTTCC**TTTTCTGGAAGTGAGGCCACAGCAGCTATCCTT
AGCAGAGCACCCTGGAGTCTGCAAAGTGTTAATCCAGGCCTAAAGACAAATTCTTCTAAGGAGCCTAAATTCACC
AAGTGCCGTTCACCTGAGCGAGAGACTTTTTCATGCCACTGGACAGATGAGGTTCATCATGGTACAAAGAACCTA
GGACCCATACAGCTGTTCTATACCAGAAGGAACACTCAAGAATGGACTCAAGAATGGAAAGAATGCCCTGATTAT
GTTTCTGCTGGGGAAAACAGCTGTTACTTTAATTCATCGTTTACCTCCATCGCAATACCTTATTGTATCAAGCTA
ACTAGCAATGGTGGTACAGTGGATGAAAAGTGTTTCTCTGTTGATGAAATAGTGCAACCAGATCCACCCATTGCC
CTCAACTGGACTTTACTGAACGTCAGTTTAACTGGGATTCATGCAGATATCCAAGTGAGATGGGAAGCACCACGC
AATGCAGATATTCAGAAAGGATGGATGGTTCTGGAGTATGAACTTCAATACAAAGAAGTAAATGAAACTAAATGG
AAAATGATGGACCCTATATTGACAACATCAGTTCCAGTGTACTCATTGAAAGTGGATAAGGAATATGAAGTGCGT
GTGAGATCCAAACAACGAAACTCTGGAAATTATGGCGAGTTCAGTGAGGTGCTCTATGTAACACTTCCTCAGATG
AGCCAA*

Figure 19B

SEQ ID NO 21 mipakdmakvmivmlaicfltksdgksvkkrSVSEIQLMHNLGKHLNSMERVEWLRKKLQDVHNF**GGGGSGGGGS
GGGGSGGGGS**ddvmtkeeqifllhraqaqcekrlkevlqrpasimesdkgwtsastsgkprkdkasgklypesee
dkeaptgsryrgrpclpewdhilcwplgapgevvavpcpdykydfnhkghayrrcdrngswelvpghnrtwanys
ecvkfltnetrerevfdrlGGGGSGGGGSGGGGSGGGGSFSGSEATAAILSRAPWSLQSVNPGLKTNSSKEPKFT
KCRSPERETFSCHWTDEVHHGTKNLGPIQLFYTRRNTQEWTQEWKECPDYVSAGENSCYFNSSFTSIAIPYCIKL
TSNGGTVDEKCFSVDEIVQPDPPIALNWTLLNVSLTGIHADIQVRWEAPRNADIQKGWMVLEYELQYKEVNETKW
KMMDPILTTSVPVYSLKVDKEYEVRVRSKQRNSGNYGEFSEVLYVTLPQMSQ*

Figure 20A

SEQ ID NO 39 atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTT**GGTGGCGGAGGTAGTGGTGGCGGAGGTAGCGGTGGCGGAGGTTCT
GGTGGCGGAGGTTCC**gatgacgtcatgactaaagaggaacagatcttcctgctgcaccgtgctcaggcccagtgc
gaaaaacggctcaaggaggtcctgcagaggccagccagcataatggaatcagacaagggatggacatctgcgtcc
acatcagggaagcccaggaaagataaggcatctgggaagctctaccctgagtctgaggaggacaaggaggcaccc
actggcagcaggtaccgagggcgccctgtctgccggaatgggaccacatcctgtgctggccgctgggggcacca
ggtgaggtggtggctgtgccctgtccggactacaagtatgacttcaatcacaaaggccatgcctaccgacgctgt
gaccgcaatggcagctgggagctggtgcctgggcacaacaggacgtgggccaactacagcgagtgtgtcaaattt
ctcaccaatgagactcgtgaacgggaggtgtttgaccgcctg**GGTGGCGGAGGTAGTGGTGGCGGAGGTAGCGGT
GGCGGAGGTTCTGGTGGCGGAGGTTCC**TTTTCTGGAAGTGAGGCCACAGCAGCTATCCTTAGCAGAGCACCCTGG
AGTCTGCAAAGTGTTAATCCAGGCCTAAAGACAAATTCTTCTAAGGAGCCTAAATTCACCAAGTGCCGTTCACCT
GAGCGAGAGACTTTTTCATGCCACTGGACAGATGAGGTTCATCATGGTACAAAGAACCTAGGACCCATACAGCTG
TTCTATACCAGAAGGAACACTCAAGAATGGACTCAAGAATGGAAAGAATGCCCTGATTATGTTTCTGCTGGGGAA
AACAGCTGTTACTTTAATTCATCGTTTACCTCCATCGCAATACCTTATTGTATCAAGCTAACTAGCAATGGTGGT
ACAGTGGATGAAAAGTGTTTCTCTGTTGATGAAATAGTGCAACCAGATCCACCCATTGCCCTCAACTGGACTTTA
CTGAACGTCAGTTTAACTGGGATTCATGCAGATATCCAAGTGAGATGGGAAGCACCACGCAATGCAGATATTCAG
AAAGGATGGATGGTTCTGGAGTATGAACTTCAATACAAAGAAGTAAATGAAACTAAATGGAAAATGATGGACCCT
ATATTGACAACATCAGTTCCAGTGTACTCATTGAAAGTGGATAAGGAATATGAAGTGCGTGTGAGATCCAAACAA
CGAAACTCTGGAAATTATGGCGAGTTCAGTGAGGTGCTCTATGTAACACTTCCTCAGATGAGCCAA*

Figure 20B
SEQ ID NO 22
matgsrtslllafgllclpwlqegsaSVSEIQLMHNLGKHLNSMERVEWLRKKLQDVHNFGGGGSGGGGSGGGGS
GGGGSddvmtkeeqifllhraqaqcekrlkevlqrpasimesdkgwtsastsgkprkdkasgklypeseedkeap
tgsryrgrpclpewdhilcwplgapgevvavpcpdykydfnhkghayrrcdrngswelvpghnrtwanysecvkf
ltnetrerevfdrlGGGGSGGGGSGGGGSGGGGSFSGSEATAAILSRAPWSLQSVNPGLKTNSSKEPKFTKCRSP
ERETFSCHWTDEVHHGTKNLGPIQLFYTRRNTQEWTQEWKECPDYVSAGENSCYFNSSFTSIAIPYCIKLTSNGG
TVDEKCFSVDEIVQPDPPIALNWTLLNVSLTGIHADIQVRWEAPRNADIQKGWMVLEYELQYKEVNETKWKMMDP
ILTTSVPVYSLKVDKEYEVRVRSKQRNSGNYGEFSEVLYVTLPQMSQ*

Figure 21A
SEQ ID NO 38
atgatacctgcaaaagacatggctaaagttatgattgtcatgttggcaatttgttttcttacaaaatcggatggg
aaatctgttaagaagagaTCTGTGAGTGAAATACAGCTTATGCATAACCTGGGAAAACATCTGAACTCGATGGAG
AGAGTAGAATGGCTGCGTAAGAAGCTGCAGGATGTGCACAATTTTGGTGGCGGAGGTAGTGGTGGCGGAGGTAGC
GGTGGCGGAGGTTCTGGTGGCGGAGGTTCCgatgacgtcatgactaaagaggaacagatcttcctgctgcaccgt
gctcaggcccagtgcgaaaaacggctcaaggaggtcctgcagaggccagccagcataatggaatcagacaaggga
tggacatctgcgtccacatcaggaagcccaggaaagataaggcatctgggaagctctaccctgagtctgaggag
gacaaggaggcacccactggcagcaggtaccgagggcgcccctgtctgccggaatgggaccacatcctgtgctgg
ccgctgggggcaccaggtgaggtggtggctgtgccctgtccggactacaagtatgacttcaatcacaaaggccat
gcctaccgacgctgtgaccgcaatggcagctgggagctggtgcctgggcacaacaggacgtgggccaactacagc
gagtgtgtcaaatttctcaccaatgagactcgtgaacgggaggtgtttgaccgcctgaccggtCATCATCACCAT
CACCAT*

Figure 21B
SEQ ID NO 23
mipakdmakvmivmlaicfltksdgksvkkrSVSEIQLMHNLGKHLNSMERVEWLRKKLQDVHNFGGGGSGGGGS
GGGGSGGGGSddvmtkeeqifllhraqaqcekrlkevlqrpasimesdkgwtsastsgkprkdkasgklypesee
dkeaptgsryrgrpclpewdhilcwplgapgevvavpcpdykydfnhkghayrrcdrngswelvpghnrtwanys
ecvkfltnetrerevfdrlTGHHHHHH

Figure 22A
SEQ ID NO 6
atggctacaggctcccggacgtccctgctcctggcttttggcctgctctgcctgccctggcttcaagagggcagt
gccTCTGTGAGTGAAATACAGCTTATGCATAACCTGGGAAAACATCTGAACTCGATGGAGAGAGTAGAATGGCTG
CGTAAGAAGCTGCAGGATGTGCACAATTTTGGTGGCGGAGGTAGTGGTGGCGGAGGTAGCGGTGGCGGAGGTTCT
GGTGGCGGAGGTTCCgatgacgtcatgactaaagaggaacagatcttcctgctgcaccgtgctcaggcccagtgc
gaaaaacggctcaaggaggtcctgcagaggccagccagcataatggaatcagacaagggatggacatctgcgtcc
acatcaggaagcccaggaaagataaggcatctgggaagctctaccctgagtctgaggaggacaaggaggcaccc
actggcagcaggtaccgagggcgcccctgtctgccggaatgggaccacatcctgtgctggccgctgggggcacca
ggtgaggtggtggctgtgccctgtccggactacaagtatgacttcaatcacaaaggccatgcctaccgacgctgt
gaccgcaatggcagctgggagctggtgcctgggcacaacaggacgtgggccaactacagcgagtgtgtcaaattt
ctcaccaatgagactcgtgaacgggaggtgtttgaccgcctgaccggtCATCATCACCATCACCAT*

Figure 22B
SEQ ID NO 24
matgsrtslllafgllclpwlqegsaSVSEIQLMHNLGKHLNSMERVEWLRKKLQDVHNFGGGGSGGGGSGGGGS
GGGGSddvmtkeeqifllhraqaqcekrlkevlqrpasimesdkgwtsastsgkprkdkasgklypeseedkeap
tgsryrgrpclpewdhilcwplgapgevvavpcpdykydfnhkghayrrcdrngswelvpghnrtwanysecvkf
ltnetrerevfdrlTGHHHHHH*

Figure 23
SEQ ID NO 9
SVSEIQLMHNLGKHLNSMERVEWLRKKLQDVHNFVALGAPLAPRDAGSQRPRKKEDNVLVESHEKSLGE
ADKADVNVLTKAKSQ

Figure 24
SEQ ID NO 40: PTHrP (1-36)
AVSEHQLLHDKGKSIQDLRRRFFLHHLIAEIHTAEI

Figure 25
SEQ ID NO 41: PTHrP signal sequence
MQRRLVQQWSVAVFLLSYAVPSCG

Figure 26
SEQ ID NO 4: PTHrP propeptide
rsveglsrrl

PARATHYROID HORMONE FUSION POLYPEPTIDE

CROSS REFERENCE TO RELATED APPLICATIONS

This is the U.S. National Stage of International Application No. PCT/GB2018/051120, filed Apr. 27, 2018, which was published in English under PCT Article 21(2), which in turn claims the benefit of Great Britain Application No. 1706781.0, filed Apr. 28, 2017.

FIELD OF THE INVENTION

The disclosure relates to long acting parathyroid hormone fusion polypeptides comprising a receptor polypeptide wherein the receptor polypeptide is a parathyroid hormone receptor and/or growth hormone receptor; nucleic acid molecules encoding said fusion polypeptides; vectors adapted to express said fusion polypeptides; cells transformed or transfected with said nucleic acids or vectors; and use of said polypeptides in the treatment of hypoparathyroidism.

BACKGROUND OF THE INVENTION

Hypoparathyroidism, characterised by low parathyroid hormone (PTH) levels, is a rare condition and is either congenital or more often acquired following surgery to the neck. PTH is secreted by the four parathyroid glands which are located next to the thyroid gland in the neck and controls calcium homeostasis, vitamin D-dependent calcium absorption, renal calcium reabsorption and renal phosphate clearance. PTH stimulates the release of calcium from the bone and enhances absorption of calcium in the intestine. Reduced PTH levels lead to hypocalcaemia and include symptoms such as neuromuscular irritability, including paraesthesia, muscle twitching, laryngeal spasms, tetany and seizures and can lead, if untreated to death.

Current standard therapy is high dose calcium and active vitamin D; however, many patients show despite treatment fluctuating calcium levels, an increased incidence of depression as well as an increased risk of infections and renal complications such as calcifications and renal insufficiency. PTH is an 84-amino acid long polypeptide comprising a 34 long amino acid N-terminal biologically active domain which was found to be an effective PTH receptor agonist.

Currently recombinant PTH is administered as a daily subcutaneous injection. PTH is known to be unstable in vitro and has a short half-life in vivo resulting in fluctuating PTH levels which are associated with nausea and vomiting. Compositions stabilising PTH in vitro are disclosed in U.S. Pat. Nos. 7,550,434, 7,144,861, 6,770,623, WO2006/129995 or WO2013/108235, and recombinant PTH analogues with enhanced pharmacokinetics and pharmacodynamics comprising a modified PTH fragment of up to 36 amino acids are disclosed in WO2011143406.

However, longer acting PTH biologics with an increased control over serum calcium levels and reduced side effects are urgently needed to minimise the need for daily subcutaneous injection.

Recombinant proteins and peptides used in pharmaceuticals often suffer from increased serum clearance. Factors that result in the removal of administered proteins from the circulation have two components; renal filtration and proteolysis. Typically, proteins with a molecular weight above 70 kDa are not cleared by glomerular filtration because they are simply too large to be filtered, however, proteins of small molecular weight are filtered by the glomerulus and are found in the urine. A method to increase the effective molecular weight of proteins and to produce a product which has reduced immunogenicity is to coat the protein in polyethylene glycol (PEG). PEG is believed to slow renal clearance by providing increased hydrodynamic volume in pegylated proteins (Maxfield et al., Polymer, 16:505-509 (1975)). However, pegylation of proteins can result in decreased affinity for its receptor reducing the biological activity. An alternative means to improved PK and PD of protein biologics is disclosed in WO2009/013461. Human growth hormone fused to an extracellular domain of human growth hormone receptor (GHR) have enhanced PK and PD improving PK by approximately 200-fold when compared to growth hormone. In PCT/GB2016/053218, currently unpublished, the effect of GHR on non-growth hormone polypeptides is disclosed wherein leptin and granulocyte colony stimulating factor (GSCF) when fused to GHR have improved PK and PD.

This disclosure relates to PTH fusion polypeptides wherein PTH fused to a receptor, for example, its cognate receptor and/or GHR have improved PK and PD. The PTH fusion polypeptides have utility in the treatment of conditions that result from abnormal PTH activity including hypoparathyroidism and treatment of conditions that benefit from PTH therapy including osteoporosis.

STATEMENTS OF THE INVENTION

According to an aspect of the invention there is provided a fusion polypeptide comprising
 a polypeptide comprising an amino acid sequence of a parathyroid hormone or biologically active fragment or analogue thereof,
 a polypeptide comprising an amino acid sequence of a receptor polypeptide or fragment or analogue thereof wherein said parathyroid hormone or biologically active fragment or analogue thereof is linked either directly or indirectly as a translational fusion to said receptor polypeptide.

"Analogue" refers to a parathyroid hormone that binds parathyroid hormone receptor or a receptor polypeptide amino acid sequence variant. The parathyroid hormone analogue includes but is not limited to amino acid sequences encoding the parathyroid hormone related protein and variants thereof.

In a preferred embodiment of the invention said fusion polypeptide comprises a parathyroid hormone comprising or consisting of the amino acid sequence set forth in SEQ ID NO: 10.

In a referred embodiment of the invention said fusion polypeptide comprises a fragment of SEQ ID NO: 10 including amino acids 1-28, 1-29, 1-30, 1-31, 1-32, 1-33, 1-34, or 1-35.

In a preferred embodiment of the invention said fusion polypeptide comprises a parathyroid hormone comprising the sequence set forth in SEQ ID NO: 9.

In a referred embodiment of the invention said fusion polypeptide comprises a fragment of SEQ ID NO: 9 including amino acids 1-28, 1-29, 1-30, 1-31, 1-32, 1-33, 1-34, or 1-35.

In a preferred embodiment of the invention said fusion polypeptide comprises a parathyroid hormone comprising or consisting of the amino acid sequence set forth in SEQ ID NO: 54.

In a preferred embodiment of the invention said fusion polypeptide comprises a parathyroid hormone analogue comprising or consisting of the amino acid sequence of formula (I):

(SEQ ID NO: 8)
Xaa01-Val-Xaa03-Glu-Ile-Gln-Leu-Xaa08-His-Xaa10-

Xaa11-Xaa12-Xaa13-Xaa14-Leu-Xaa16-Xaa17-Xaa18-

Arg-Arg-Arg-Xaa22-Phe-Leu-Xaa25-Xaa26-Leu-Ile-

Ala-Glu-Ile-His-Thr-Ala-Glu-Ile (I) where Xaa01 is Ser or Ala; Xaa03 is Ser or Ala; Xaa08 is Met or Leu; Xaa10 is Asn, Ala, Val, Asp, Glu, or Gln; Xaa11 is Leu, Ala, Val, Met, Lys, Arg, or Trp; Xaa12 is Gly, Ala, His, or Arg; Xaa13 is Lys, Ala, Leu, Gln, Arg, His, or Trp; Xaa14 is His, Leu, Arg, Phe, Trp, or Ser; Xaa16 is Gln or Asn; Xaa17 is Asp or Ser; Xaa18 is Ala, Leu, Met, Glu, Ser, or Phe; Xaa22 is Ala, Phe, Glu, Ser, Leu, Asn, Trp, or Lys; Xaa25 is His, Arg, Leu, Trp, or Lys; and Xaa26 is Lys, His, Ala, Ser, Asn, or Arg or a fragment thereof including amino acids 1-28, 1-29, 1-30, 1-31, 1-32, 1-33, 1-34, or 1-35 of formula (I), with the proviso that at least one of Xaa18 is not Leu or Met, Xaa22 is not Phe, and Xaa26 is not His.

In a preferred embodiment of the invention said fusion polypeptide comprises a parathyroid hormone and parathyroid hormone analogue amino acid sequence comprising or consisting of the amino acid sequence set forth in SEQ ID NO: 37.

In an alternative embodiment of the invention said fusion polypeptide comprises a parathyroid hormone related protein or biologically active fragment or analogue thereof, comprising the amino acid sequence set forth in SEQ ID NO: 40.

In a referred embodiment of the invention said fusion polypeptide comprises a fragment of SEQ ID NO: 40 including amino acids 1-28, 1-29, 1-30, 1-31, 1-32, 1-33, 1-34, or 1-35.

In a preferred embodiment of the invention said fusion polypeptide comprises a receptor polypeptide comprising a parathyroid hormone receptor extracellular domain.

In a preferred embodiment of the invention said fusion polypeptide comprises a parathyroid hormone receptor extracellular domain comprising or consisting of the amino acid sequence set forth in SEQ ID NO: 3.

In a further preferred embodiment of the invention said fusion polypeptide comprises a parathyroid hormone receptor extracellular domain, or fragment thereof, comprising an amino acid sequence, between 10-99% identical to the full length amino acid sequence set forth in SEQ ID NO: 3 and wherein said domain or fragment binds a parathyroid hormone, fragment or analogue thereof.

In a further preferred embodiment of the invention said fusion polypeptide comprises a parathyroid hormone receptor extracellular domain or fragment thereof comprising an amino acid sequence that is 10, 15, 20, 30, 40, 50, 60, 70, 80, 85, 90, 91, 92, 93, 94, 95, 96, 97, 98 or 99% identical to the amino acid sequence set forth in SEQ ID NO: 3 and wherein said domain binds a parathyroid hormone, fragment or analogue thereof.

In a preferred embodiment of the invention said fusion polypeptide comprises a modified amino acid sequence encoding the parathyroid hormone receptor extracellular domain wherein said modification is one or more amino acid substitutions selected from the group consisting of: 1107 K, D109A, P104L or L159A as set forth in SEQ ID NO: 3.

In a further preferred embodiment of the invention said fusion polypeptide comprises a parathyroid hormone receptor extracellular domain comprising an 107K substitution as set forth in SEQ ID NO: 3.

In a preferred embodiment of the invention said fusion polypeptide comprises a parathyroid hormone comprising or consisting of the amino acid residues 1-14 of the sequence set forth in SEQ ID NO: 10.

In an alternative embodiment of the invention said fusion polypeptide comprises a modified parathyroid hormone receptor extracellular domain wherein said modification is by addition, deletion or substitution of at least one amino acid residue wherein said modified polypeptide substantially lacks parathyroid hormone binding activity or has reduced parathyroid hormone binding activity.

In an embodiment of the invention said fusion polypeptide comprising a receptor polypeptide and alternatively or additionally comprises a growth hormone binding domain polypeptide of growth hormone receptor.

In a preferred embodiment of the invention said fusion polypeptide comprises the extracellular growth hormone binding domain polypeptide of human growth hormone receptor.

In a further embodiment of the invention said fusion polypeptide comprises an extracellular growth hormone binding domain polypeptide comprising of the amino acid sequence set forth in SEQ ID NO: 5.

In an alternative embodiment of the invention said fusion polypeptide comprises a modified extracellular growth hormone binding domain polypeptide wherein said modification is by addition, deletion or substitution of at least one amino acid residue wherein said modified polypeptide substantially lacks growth hormone binding activity or has reduced growth hormone binding activity.

In a preferred embodiment of the invention said fusion polypeptide comprises a modification of one or more of the amino acid residues selected from the group consisting of: W169, R43, E44, I103, W104, I105, P106, I164 and D165 as set forth in SEQ ID NO: 5.

In a further preferred embodiment of the invention said fusion polypeptide comprises a deletion of amino acid residue tryptophan 104 of the amino acid sequence set forth in SEQ ID NO: 5.

In an alternative embodiment of the invention said fusion polypeptide comprises a substitution of tryptophan 104 of the amino acid sequence as set forth in SEQ ID NO: 5.

In a preferred embodiment of the invention said fusion polypeptide comprises the substitution of tryptophan 104 for alanine as set forth in SEQ ID NO: 7.

In a further preferred embodiment of the invention said fusion polypeptide comprises or consists of a parathyroid hormone fragment comprising or consisting of the amino acid residues 1-28, 1-29, 1-30, 1-31, 1-32, 1-33, 1-34, or 1-35 of SEQ ID NO: 8.

In a further preferred embodiment said fusion polypeptide comprises a parathyroid hormone or analogue thereof comprising or consisting of the amino acid sequence set forth in SEQ ID Nos: 8, 9 or 10 wherein said parathyroid hormone amino acid sequence is modified by addition, deletion or substitution of at least one amino acid residue and wherein said modified fusion polypeptide retains parathyroid hormone activity.

In a further preferred embodiment said fusion polypeptide comprises a parathyroid hormone or analogue thereof comprising or consisting of the amino acid sequence set forth in SEQ ID NO: 54 wherein said parathyroid hormone amino acid sequence is modified by addition, deletion or substitution of at least one amino acid residue and wherein said modified fusion polypeptide retains parathyroid hormone activity.

In a further preferred embodiment said fusion polypeptide comprises a parathyroid hormone analogue comprising or consisting of the amino acid sequence set forth in SEQ ID NO: 37 or 40 wherein said parathyroid hormone amino acid sequence is modified by addition, deletion or substitution of at least one amino acid residue and wherein said modified fusion polypeptide retains parathyroid hormone activity.

In a further preferred embodiment said fusion polypeptide comprises a modified amino acid sequence that is 40, 45, 50, 55, 60, 65, 70, 75, 80, 85, 90, 91, 92, 93, 94, 95, 96, 97, 98, 99% identical over the full length of the amino acid sequence set forth in SEQ ID NOs:-8, 9 or 10.

In a further preferred embodiment said fusion polypeptide comprises a modified amino acid sequence that is 40, 45, 50, 55, 60, 65, 70, 75, 80, 85, 90, 91, 92, 93, 94, 95, 96, 97, 98, 99% identical over the full length of the amino acid sequence set forth in SEQ ID: NO: 40 or 37.

In a further preferred embodiment said fusion polypeptide comprises a modified amino acid sequence that is 40, 45, 50, 55, 60, 65, 70, 75, 80, 85, 90, 91, 92, 93, 94, 95, 96, 97, 98, 99% identical over the full length of the amino acid sequence set forth in SEQ ID: NO: 54.

In a preferred embodiment of the invention said fusion polypeptide comprises a parathyroid receptor domain polypeptide wherein said parathyroid receptor domain polypeptide is located at the carboxyl-terminal end of said fusion polypeptide.

In an alternative embodiment of the invention said fusion polypeptide comprises a parathyroid receptor domain polypeptide wherein said parathyroid receptor domain polypeptide is located at the amino-terminal end of said fusion polypeptide.

In an alternative embodiment of the invention said fusion polypeptide comprises a growth hormone binding domain polypeptide wherein said growth hormone binding domain polypeptide is located at the carboxyl terminal end of said fusion polypeptide.

In an embodiment of the invention said fusion polypeptide comprises a growth hormone binding domain polypeptide wherein said growth hormone binding domain polypeptide is located at the amino terminal end of said fusion polypeptide.

In a preferred embodiment of the invention said fusion polypeptide comprises or consists of an amino acid sequence set forth in SEQ ID NO: 12, 13, 14, 15, 16, 17, 18, 19, 20, 21, 22, 23, 24, 25, 26, 27, 28, 29, 30, 31, 32, 33, 34, 35 or 36.

In a preferred embodiment of the invention said fusion polypeptide comprises or consists of an amino acid sequence set forth in SEQ ID NO: 15 or 20.

In a preferred embodiment of the invention said fusion polypeptide comprises or consists of an amino acid sequence set forth in SEQ ID NO: 42, 43, 44, 45, 46, 47, 48, 49, 50, 51, 52 or 53.

In a preferred embodiment of the invention said fusion polypeptide comprises a pro-peptide.

In a further preferred embodiment of the invention said pro-peptide comprises or consists of SEQ ID NO: 11.

In an alternative preferred embodiment of the invention said pro-peptide comprises or consists of SEQ ID NO: 4.

In a preferred embodiment of the invention said fusion polypeptide further comprises a peptide secretion signal.

In a preferred embodiment of the invention said fusion polypeptide comprises a parathyroid hormone peptide secretion signal.

In a preferred embodiment of the invention said parathyroid hormone peptide secretion signal comprises the amino acid sequence set forth in SEQ ID NO: 1.

In a preferred embodiment of the invention said fusion polypeptide comprises a parathyroid hormone related protein peptide secretion signal.

In a preferred embodiment of the invention said parathyroid hormone related protein peptide secretion signal comprises the amino acid sequence set forth in SEQ ID NO: 41.

In an alternative preferred embodiment of the invention said fusion polypeptide comprises a growth hormone peptide secretion signal.

In a preferred embodiment of the invention said fusion polypeptide comprises a growth hormone secretion signal comprising the amino acid sequence set forth in SEQ ID NO: 2.

In a preferred embodiment of the invention said fusion polypeptide comprises a parathyroid hormone, fragment or analogue thereof and is linked directly or indirectly to said receptor polypeptide by a peptide linker.

In an alternative embodiment of the invention said parathyroid hormone, fragment or analogue is directly linked to said receptor polypeptide as an in-frame translational fusion.

Preferably said peptide linker comprises the amino acid sequence Gly Gly Gly Gly Ser (residues 60-64 of SEQ ID NO: 12).

In a further preferred embodiment said peptide linker comprises 1, 2, 3, 4, 5, 6, 7, 8, 9 or 10 repeat units of a peptide comprising the amino acid sequence Gly Gly Gly Gly Ser (residues 60-64 of SEQ ID NO: 12).

In a further preferred embodiment said peptide linker comprises 4 repeat units of the amino acid sequence Gly Gly Gly Gly Ser (residues 60-64 of SEQ ID NO: 12).

According to a further aspect of the invention there is provided a nucleic acid molecule that encodes a fusion polypeptide according to the invention.

According to a further aspect of the invention there is provided a vector comprising a nucleic acid molecule according to the invention.

In a preferred embodiment of the invention said vector is an expression vector adapted to express the nucleic acid molecule according to the invention.

A vector including nucleic acid (s) according to the invention need not include a promoter or other regulatory sequence, particularly if the vector is to be used to introduce the nucleic acid into cells for recombination into the genome for stable transfection. Preferably the nucleic acid in the vector is operably linked to an appropriate promoter or other regulatory elements for transcription in a host cell. The vector may be a bi-functional expression vector which functions in multiple hosts. By "promoter" is meant a nucleotide sequence upstream from the transcriptional initiation site and which contains all the regulatory regions required for transcription. Suitable promoters include constitutive, tissue-specific, inducible, developmental or other promoters for expression in eukaryotic or prokaryotic cells. "Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is a constitutive, an inducible or regulatable promoter.

According to a further aspect of the invention there is provided a cell transfected or transformed with a nucleic acid molecule or vector according to the invention.

Preferably said cell is a eukaryotic cell.

In a preferred embodiment of the invention said cell is selected from the group consisting of; a fungal cell (e.g. *Pichia* spp, *Saccharomyces* spp, *Neurospora* spp); insect cell (e.g. *Spodoptera* spp); a mammalian cell (e.g. COS cell, CHO cell); a plant cell.

In an alternative embodiment of the invention said cell is a prokaryotic cell.

According to an aspect of the invention there is provided a method for the production of the fusion polypeptide according to the invention comprising the steps consisting of:
  i) providing a cell according to the invention and cell culture medium;
  ii) culturing said cell; and
  iii) isolating from said cell or medium a fusion polypeptide according to the invention.

According to a further aspect of the invention there is provided a pharmaceutical composition comprising a fusion polypeptide according to the invention including an excipient or carrier.

In a preferred embodiment of the invention said pharmaceutical composition is combined with a further therapeutic agent.

When administered the pharmaceutical composition of the present invention is administered in pharmaceutically acceptable preparations. Such preparations may routinely contain pharmaceutically acceptable concentrations of salt, buffering agents, preservatives, compatible carriers, and optionally other therapeutic agents for example chemotherapeutic agents.

The pharmaceutical compositions of the invention can be administered by any conventional route, including injection. The administration and application may, for example, be subcutaneous.

Pharmaceutical compositions of the invention are administered in effective amounts. An "effective amount" is that amount of pharmaceuticals/compositions that alone, or together with further doses or synergistic drugs, produces the desired response. This may involve only slowing the progression of the disease temporarily, although more preferably, it involves halting the progression of the disease permanently. This can be monitored by routine methods or can be monitored according to diagnostic methods.

The doses of the pharmaceuticals compositions administered to a subject can be chosen in accordance with different parameters, in particular in accordance with the mode of administration used and the state of the subject (i.e. age, sex). When administered, the pharmaceutical compositions of the invention are applied in pharmaceutically-acceptable amounts and in pharmaceutically-acceptable compositions. When used in medicine salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions may be combined, if desired, with a pharmaceutically-acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction that would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for subcutaneous administration conveniently comprise a sterile aqueous or non-aqueous preparation that is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1, 3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for subcutaneous administrations can be found in Remington's Pharmaceutical Sciences, Mack Publishing Co., Easton, Pa.

According to an aspect of the invention there is provided a fusion polypeptide according to the invention for use in the treatment of hypoparathyroidism in a subject.

According to a further aspect of the invention there is provided a method to treat a human subject suffering from hypoparathyroidism comprising administering an effective amount of a fusion polypeptide according to the invention thereby treating hypoparathyroidism.

According to an aspect of the invention there is provided a fusion polypeptide according to the invention for use in the treatment of osteoporosis in a human subject.

According to a further aspect of the invention there is provided a method to treat a human subject suffering from osteoporosis comprising administering an effective amount of a fusion polypeptide according to the invention thereby treating osteoporosis.

In a preferred embodiment or method of the invention said fusion polypeptide comprises the amino acid sequence set forth in SEQ ID NO: 40.

In a preferred embodiment or method of the invention said fusion polypeptide is administered in combination with calcium carbonate and/or vitamin D supplements such as calcitrol or alfacalcitrol.

In a preferred embodiment or method of the invention said hypoparathyroidism is caused by thyroid or neck surgery, autoimmune disease, radiotherapy, cancer, Addison's disease or Di-George syndrome.

In a preferred embodiment or method of the invention said fusion polypeptide is administered at least once a day.

In an embodiment or method of the invention said fusion polypeptide is administered at least once or twice weekly.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

BRIEF SUMMARY OF THE DRAWINGS

FIG. 2A) Purified 14A1, FIG. 2B) Purified 14A2b. Proteins were expressed in a CHO cell line and purified as a secreted product from Hyclone SFM4CHO Utility media using a combination of Q-Sepharose and anti-growth hormone receptor affinity chromatography. Protein separates at ~75-100 kDa and is intact with no sign of degradation;

FIG. 3: In Vitro Bioactivity of 14A1 and 14A2 proteins. Purified proteins were tested for their ability to stimulate cAMP production from the PTH responsive cell line, UMR-106 (rat osteoblastic like cell line). Cells were stimulated for 15 minutes in the presence of test molecules and cAMP levels measured from cell lysates using a cAMP specific Elisa. Both positive controls, PTH 1-34 (100 nM), Forskolin (100 µM) and negative controls (Cells only, Buffer only and Control protein, Erythropoetin) were included in the analysis. Data is presented as pmol cAMP/ml+/−Standard deviation;

FIGS. 4A and 4B: Parathyroid Hormone, LOCUS NM_000315 834 bp mRNA linear PRI 13 Jun. 2016, DEFINITION *Homo sapiens* parathyroid hormone (PTH), transcript variant 1, mRNA, ACCESSION NM_000315, VERSION NM_000315.3, KEYWORDS RefSeq., SOURCE *Homo sapiens* (human). FIG. 4A) Signal peptide underlined, propeptide italics/lowercase, mature protein (1-34) shown in uppercase/bold, FIG. 4B) origin, Signal peptide is underlined (116-190 bp), Propeptide in lowercase/italics, Mature protein in uppercase/bold (209-460 bp);

FIGS. 5A-5D: PTH 1-34 used in fusion proteins; FIG. 5A) Amino acid sequence of PTH 1-34, FIG. 5B) nucleotide sequence (102 bp), FIG. 5C) Amino acid sequence of PTH signal peptide and propeptide sequence used in fusion proteins (propeptide in lowercase/italics), FIG. 5D) Nucleotide sequence of PTH signal peptide and propeptide sequence used in fusion proteins (propeptide in lowercase/italics);

FIGS. 6A and 6B: Human parathyroid hormone receptor 1, FIG. 6A) LOCUS NM_001184744 2007 bp mRNA linear PRI 6 Oct. 2016, DEFINITION *Homo sapiens* parathyroid hormone 1 receptor (PTH1R), transcript variant 2, mRNA. ACCESSION NM_001184744 VERSION NM_001184744.1, KEYWORDS RefSeq., SOURCE *Homo sapiens* (human), Signal peptide underlined, Mature extracellular domain in bold (D29-1187); FIG. 6B) Signal peptide underlined, Mature extracellular domain in bold;

FIGS. 7A and 7B: PTH receptor extracellular domain used in fusion proteins. FIG. 7A) Amino acid sequence (aa D29-L187), FIG. 7B) Nucleotide sequence (477 bp);

FIGS. 8A and 8B: Human growth hormone binding protein (GHBP), FIG. 8A) GHBP portion of the fusion is composed of amino acid residues 1-238 (extracellular domain) and includes a W104A mutation, Nucleotide sequence of GHBP (714 bp); FIG. 8B) Amino acid sequence (aa 1-238);

FIGS. 9A and 9B: GH Secretion signal, FIG. 9A) amino acid sequence, FIG. 9B) nucleotide sequence;

FIGS. 10A and 10B: PTH-(g4s)4-PTHrEx-(g4s)4-GHBP (Code #14A1); PTH Signal peptide: Lowercase, PTH (aa 1-34): Uppercase/Underlined, PTHrExt (aa 1-159): bold/Lowercase, GHBP (aa 1-238): Uppercase; Linker regions (g4s)4: Uppercase/Bold; FIG. 10A) nucleotide sequence, FIG. 10B) protein sequence;

FIGS. 11A and 11B: PTH-(g4s)4-PTHrExt-(g4s)4-GHBP (Code #14A2), PTH Signal peptide and propeptide: Lowercase, PTH (aa 1-34): Uppercase/Underlined, PTHrExt (aa 1-159): Lowercase/Bold, GHBP (aa 1-238): Uppercase, Linker regions (g4s)4: Uppercase/Bold;

FIG. 11A) nucleotide sequence, FIG. 11B) protein sequence;

FIGS. 12A and 12B: PTH-(g4s)4-PTHrExt-(g4s)4-GHBP (Code #14A3), GH Signal peptide: Lowercase, PTH (aa 1-34): Uppercase/Underlined, PTHrExt (aa 1-159): Lowercase/Bold, GHBP (aa 1-238): Uppercase, Linker regions (g4s)4: Uppercase/Bold; FIG. 12A) nucleotide sequence, FIG. 12B) protein sequence;

FIGS. 13A and 13B: PTH-(g4s)4-GHBP (Code #14A4), GH Signal peptide: Lower case, PTH (aa 1-34): Uppercase/Underlined, GHBP (aa 1-238): Uppercase, Linker region (g4s)4: Uppercase/Bold; FIG. 13A) nucleotide sequence, FIG. 13B) protein sequence;

FIGS. 14A and 14B: PTH-(g45)4-PTHrExt_Hist (Code #14A5_Hist), GH Signal peptide: Lower case, PTH (aa 1-34): Uppercase/Underlined, PTHrExt (aa 1-159): Lowercase/Bold, Linker region (g4s)4: Uppercase/Bold, C-terminal 6× Hist tag: Uppercase/Underlined, FIG. 14A) nucleotide sequence, FIG. 14B) protein sequence;

FIGS. 15A and 15B: PTH-(g4s)4-PTHrExt (Code #14A5), GH Signal peptide: Lowercase, PTH (aa 1-34):

Uppercase/Underlined, PTHrExt (aa 1-159): Lowercase/ Bold, Linker region (g4s)4: Uppercase/Bold; FIG. 15A) nucleotide sequence, FIG. 15B) protein sequence;

FIGS. 16A and 16B: PTH-(g45)4-PTHrExt_Hist (Code #14A6_Hist), PTH Signal peptide & propeptide: Lowercase), PTH (aa 1-34): Uppercase/Underlined, PTHrExt (aa 1-159): Lowercase/Bold, Linker regions (g4s)4: Uppercase/Bold, C-terminal 6× Hist tag: Uppercase/Underlined; FIG. 16A) nucleotide sequence, FIG. 16B) protein sequence;

FIGS. 17A and 17B: PTH-(g45)4-PTHrExt_Hist (Code #14A6), PTH Signal peptide & propeptide: Lower case, PTH (aa 1-34): Uppercase/Underlined, PTHrExt (aa 1-159): Lowercase/Bold, Linker regions (g4s)4: Uppercase/Bold; FIG. 17A) nucleotide sequence, FIG. 17B) protein sequence;

FIGS. 18A and 18B: PTH-(g4s)4-GHBP (Code #14A7), PTH Signal peptide & propeptide: Lowercase, PTH (aa 1-34): Uppercase/Underlined, GHBP (aa 1-238): Uppercase, Linker region (g4s)4: Uppercase/Bold; FIG. 18A) nucleotide sequence, FIG. 18B) protein sequence;

FIGS. 19A and 19B: PTH-(g4s)4-PTHrExt (1135K)-(g4s)4-GHBP (Code #14A8), PTH Signal peptide & propeptide: Lowercase, PTH (aa 1-34): Uppercase/Underlined, PTHrExt (1135K) (aa 1-159): Lowercase/Bold (1135K change underlined). GHBP (aa 1-238): Uppercase, Linker regions (g4s)4: Uppercase/Bold; FIG. 19A) nucleotide sequence, FIG. 19B) protein sequence;

FIGS. 20A and 20B: PTH-(g4s)4-GHBP (Code #14A9), GH Signal peptide: Lower case, PTH (aa 1-34): Uppercase/Underlined, PTHrExt (1135K) (aa 1-159): Lowercase/Bold (1135K change underlined), GHBP (aa 1-238): Uppercase, Linker regions (g4s)4: Uppercase/Bold;

FIG. 20A) nucleotide sequence, FIG. 20B) protein sequence;

FIGS. 21A and 21B: PTH-(g45)4-PTHrExt (1135K)-Hist (Code #14A10), PTH Signal peptide: Lowercase, PTH (aa 1-34): Uppercase/Underlined, PTHrExt (1135K) (aa 1-159): Lowercase/Bold (1135K change underlined), Linker region (g4s)4: Uppercase/Bold, C-terminal 6× Hist tag: Uppercase/Underlined; FIG. 21A) nucleotide sequence, FIG. 21B) protein sequence;

FIGS. 22A and 22B: PTH-(g4s)4-PTHrExt (1135K)-Hist (Code #14A11-Hist), GH Signal peptide: Lowercase, PTH (aa 1-34): Uppercase/Underlined, PTHrExt (1135K) (aa 1-159): Lowercase/Bold (1135K change underlined), Linker region (g4s)4: Uppercase/Bold, C-terminal 6× Hist tag: Uppercase/Underlined; FIG. 22A) nucleotide sequence, FIG. 22B) protein sequence;

FIG. 23 PTH Sequence (AA 1-84);

FIG. 24 (SEQ ID NO: 40): PTHrP (1-36);

FIG. 25 (SEQ ID NO: 41): PTHrP signal sequence;

FIG. 26 (SEQ ID NO: 4): PTHrP propeptide;

FIG. 27A: PTH (Purple) linked to PTHrExt (Green) which in turn is linked to GHBP (Orange). Linkers shown as grey lines. W104A change shown in blue on GHBP. It is hypothesised that a state of equilibrium exists between PTH bound to PTHrExt (Inactive State: A) and PTH being released and able to bind PTHR1 (Active State, B). FIG. 27B: PTH (Purple) linked to GHBP (Orange). Linker shown as grey line. W104A change shown in blue on GHBP;

FIG. 28A: Lane 1: 5 µg 14A2c Lane 2: 5 µg 14A3b. 14A2c (contains PTH prepropeptide) separates as two diffuse bands from 60-100 kDa. 14A3b (GHss) resolves as a single diffuse band ~75-100 kDa. FIG. 28B: Lane 3: 6 µg 14A7 Lane 4: 3 µg 14A4. Proteins judged to be >90% pure. Obtained ~10 mg 14A2c, ~4 mg 14A3b, 1.42 mg 14A7 and 0.29 mg 14A4 purified protein from a 1 litre roller bottle culture.

FIG. 29C: Dual Luciferase Reporter Assay for cAMP Activity Comparison of all 4 PTH fusion molecules. UMR-106 cells were transfected with the reporter plasmid pGL4.29/CRE/Luc2/Hygro and transfection control plasmid phRL (*Renilla*) and challenged with either PTH fusion or human PTH 1-34 for 5 hours at 37° C./5% $CO_2$. Cells were lysed and Luciferase activity measured using the Promega Dual Luciferase Assay kit. Data are presented as fold induction of control±SD. Pattern of activity is similar to previous assays for 14A2c & 14A3b vs PTH. Both PTH-GHBP fusion molecules (14A4, 49±4.17 & 14A7, 44±0.42) are more active than the PTH-PTHrExt-GHBP fusion molecules (14A2c, 15±0.09 & 14A3b, 7.7±3.13) at 100 nM. At 100 nM both 14A4 and 14A7 have comparable activity to PTH (54±2.7).

SEQUENCE LISTING

Figure 1:
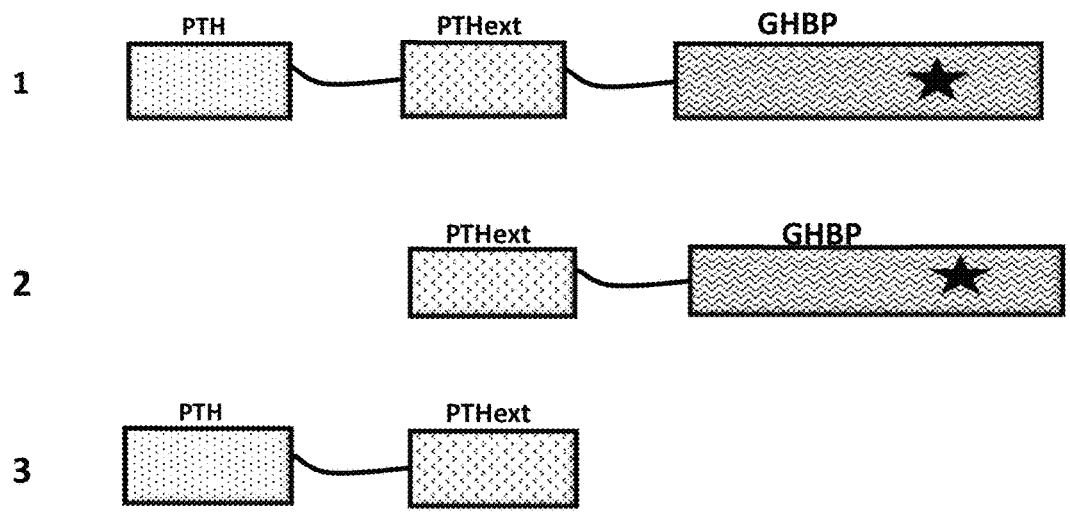
FIG. 1: We have linked PTH (residues 1-34) to the N-terminal PTH receptor domain (PTHrExt) and the growth hormone binding protein (GHBP). GHBP is an inert moiety designed to increase molecular weight and delay clearance. The binding of PTH to PTHrExt protects PTH from degradation and produces a pool of "inactive" PTH that is in equilibrium with active PTH generating a more physiological PTH exposure. Molecules will be expressed under the control of either the PTH secretion signal (with or without the inclusion of the propeptide) or the growth hormone secretion signal to allow for efficient processing in a CHO cell line.
Figure 2A:
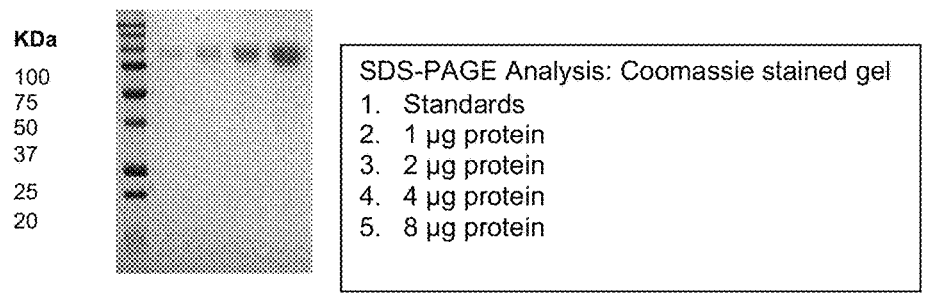
FIGS. 2A and 2B: SDS-PAGE Analysis of Purified Protein.
Figure 2B:
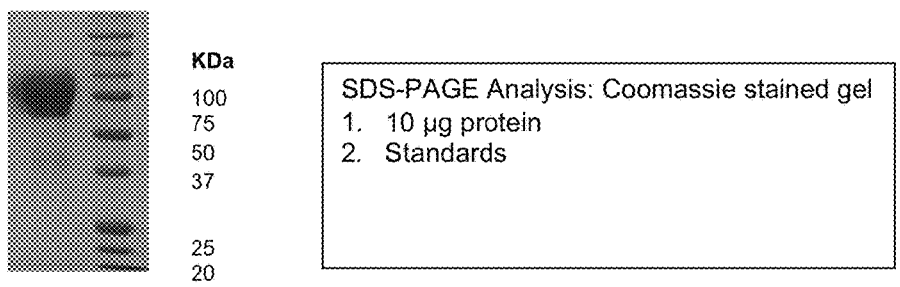
Figure 27A:
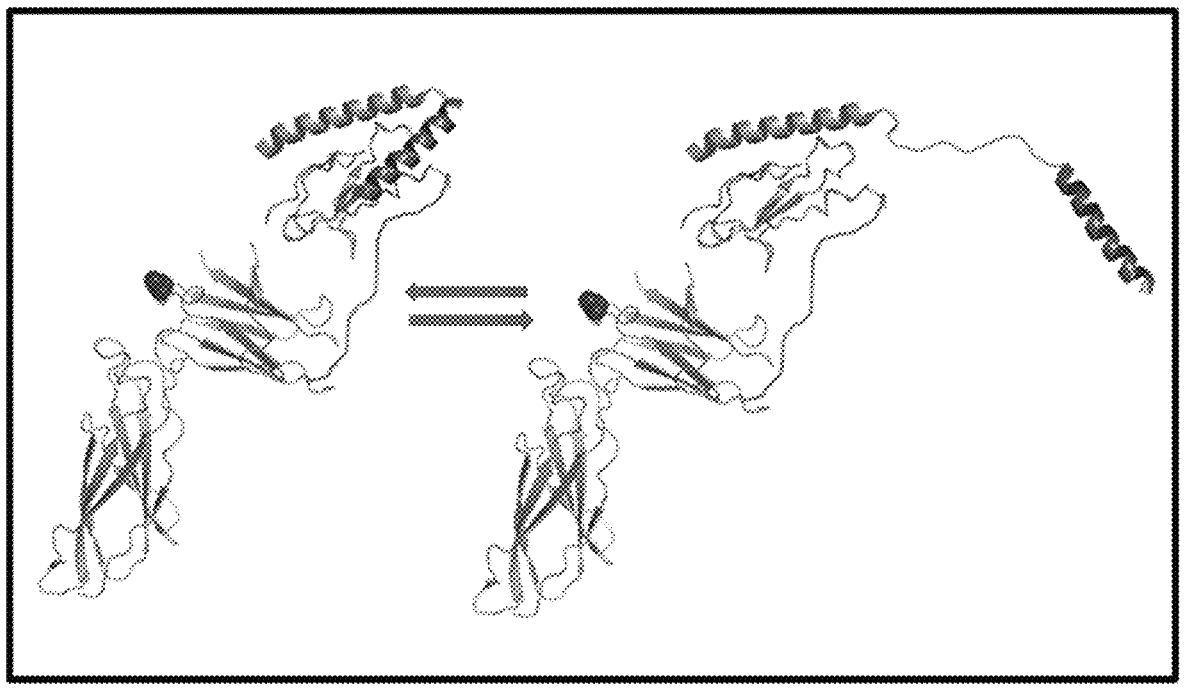
FIGS. 27A and 27B: Schematic models showing the structure of the PTH fusion molecules.
Figure 27B:
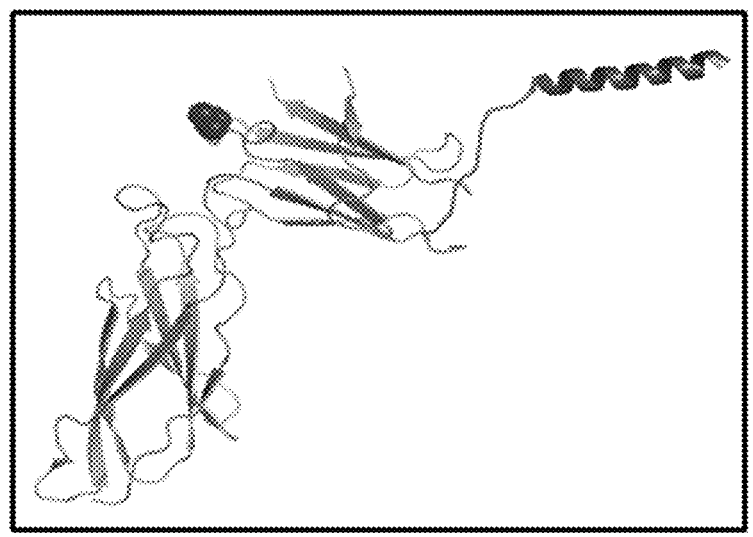

The Sequence Listing is submitted as an ASCII text file in the form of the file name "Sequence.txt" (~160 kb), which was created on Oct. 9, 2019, and which is incorporated by reference herein.

TABLE 1

| Code (SEQ ID) | Molecule Description |
|---|---|
| 14A1 (12) | PTHss-PTH-(g4s)4-PTHrExt-(g4s)4-GHBP |
| 14A2 (13) | PTHss-pp-PTH-(g4s)4-PTHrExt-(g4s)4-GHBP |
| 14A3 (14) | GHss-PTH-(g4s)4-PTHrExt-(g4s)4-GHBP |
| 14A4 (15) | GHss-PTH-(g4s)4-GHBP |
| 14A5 (16) | GHss-PTH-(g4s)4-PTHrExt |
| 14A5_Hist (17) | GHss-PTH-(g4s)4-PTHrExt-Hist |
| 14A6_Hist (18) | PTHss-pp-PTH-(g4s)4-PTHrExt-Hist |
| 14A6 (19) | PTHss-pp-PTH-(g4s)4-PTHrExt |
| 14A7 (20) | PTHss-pp-PTH-(g4s)4-GHBP |
| 14A8 (21) | PTHss-pp-PTH-(g4s)4-PTHrExt (I135K)-(g4s)4-GHBP |
| 14A9 (22) | GHss-PTH-(g4s)4-PTHrExt (I135K)-(g4s)4-GHBP |
| 14A10_Hist (23) | PTHss-pp-PTH-(g4s)4-PTHrExt (I135K)-Hist |
| 14A11_Hist (24) | GHss-pp-PTH-(g4s)4-PTHrExt (I135K)-Hist |
| 14A12 (25) | PTHss-pp-LA:PTH-(g4s)4-PTHrExt-(g4s)4-GHBP |
| 14A13 (26) | GHss-LA:PTH-(g4s)4-PTHrExt-(g4s)4-GHBP |
| 14A15 (27) | PTHss-pp-LA:PTH-(g4s)4-GHBP |
| 14A16 (28) | GHss-LA:PTH-(g4s)4-GHBP |
| 14A17 (29) | PTHss-pp-LA:PTH-(g4s)4-PTHrExt-Hist |
| 14A18 (30) | GHss-LA:PTH-(g4s)4-PTHrExt-Hist |
| 14A19 (31) | PTHss-pp-PTH (1-84)-(g4s)4-PTHrExt-(g4s)4-GHBP |
| 14A20 (32) | GHss-PTH (1-84)-(g4s)4-PTHrExt-(g4s)4-GHBP |
| 14A21 (33) | PTHss-pp-PTH (1-84)-(g4s)4-GHBP |
| 14A22 (34) | GHss-PTH (1-84)-(g4s)4-GHBP |
| 14A23 (35) | PTHss-pp-PTH (1-84)-(g4s)4-PTHrExt-Hist |
| 14A24 (36) | GHss-PTH (1-84)-(g4s)4-PTHrExt-Hist |

PTHss = Parathyroid Hormone secretion signal; pp = proppeptide; GHss = Growth hormone secretion signal; PTH = (aa 1-34 or 1-84 as stated or fragments thereof); PTHrExt = PTH receptor extracellular domain; GHBP = Growth hormone binding protein (aa 1-238); (g4s)4 = 4 repeats of amino acids GGGGS (residues 66-85 of SEQ ID NO: 20); Hist tagged = HHHHHH(residues 242-247 of SEQ ID NO: 17); I135K = mutation of Isoleucine-135 to lysine in PTHrExt; LA:PTH = long acting PTH [fusion of PTH 1-14 with PTHrP as described in text].

Linker regions in the above fusions are composed of multiples of GGGGS. In the examples given in Table 1 the linker regions are composed of 4 x GGGGS (residues 66-85 of SEQ ID NO: 20), but variable multiples can be used.

The I135K change present in PTHrExt in selected constructs has been shown to reduce the binding of PTH for the receptor. Other amino acid changes can also be used in combination or as single point mutations such as D137A, P132L & L187A. (SEQ ID NO: 56).

The numbering for the PTHrExt in the sequences below refer to the mature protein processed at Alanine 28 and therefore D29-1187 is thus referred to as amino acids 1-159 (SEQ ID NO: 3) in the following sequences.

All of above PTH sequences can be replaced with PTH 1-84 if desired and variables thereof.

TABLE 2

| List of all Proposed PTHrP Fusion Constructs (SEQ ID 42-53) | |
|---|---|
| | Molecule Description |
| 14A25 (42) | PTHrPss-pp-PTHrP-(g4s)4-PTHrExt-(g4s)4-GHBP |
| 14A26 (43) | GHss-PTHrP-(g4s)4-PTHrExt-(g4s)4-GHBP |
| 14A27 (44) | GHss-PTHrP-(g4s)4-GHBP |
| 14A28 (45) | GHss-PTHrP-(g4s)4-PTHrExt |
| 14A29_Hist (46) | GHss-PTHrP-(g4s)4-PTHrExt-Hist |
| 14A30_Hist (47) | PTHrPss-pp-PTHrP-(g4s)4-PTHrExt-Hist |
| 14A31 (48) | PTHrPss-pp-PTHrP-(g4s)4-PTHrExt |
| 14A32 (49) | PTHrPss-pp-PTHrP-(g4s)4-GHBP |
| 14A33 (50) | PTHrPss-pp-PTHrP-(g4s)4-PTHrExt (I135K)-(g4s)4-GHBP |
| 14A34 (51) | GHss-PTHrP-(g4s)4-PTHrExt (I135K)-(g4s)4-GHBP |
| 14A35_Hist (52) | PTHrPss-pp-PTHrP-(g4s)4-PTHrExt (I135K)-Hist |
| 14A36_Hist (53) | GHss-pp-PTHrP-(g4s)4-PTHrExt (I135K)-Hist |

PTHrPss = Parathyroid Hormone related protein secretion signal; pp = proppeptide; GHss = Growth hormone secretion signal; PTHrP = (aa 1-36 or fragments thereof); PTHrExt = PTH receptor extracellular domain; GHBP = Growth hormone binding protein (aa 1-238); (g4s)4 = 4 repeats of amino acids GGGGS (residues 66-85 of SEQ ID NO: 20); Hist tagged = HHHHHH (residues 242-247 of SEQ ID NO: 17); I135K = mutation of Isoleucine-135 to lysine in PTHrExt Table 3 SEQ ID Number Summary

TABLE 3

| SEQ ID NUMBER SUMMARY | |
|---|---|
| SEQ ID NO | Name |
| 1 | PTH Signal Peptide: MIPAKDMAKVMIVML AICFLTKSDG |
| 2 | GH Secretion signal: MATGSRTSLLLAFG LLCLPWLQEGSA |
| 3 | PTH receptor ECD (1-159): DDVMTKEEQIFLLHRAQAQCEKRLKEVLQRPASIM ESDKGWTSASTSGKPRKDKASGKLYPESEEDKEAP TGSRYRGRPCLPEWDHILCWPLGAPGEVVAVPCPD YIYDFNHKGHAYRRCDRNGSWELVPGHNRTWANYS ECVKFLTNETREREVFDRL |

TABLE 3-continued

SEQ ID NUMBER SUMMARY

| SEQ ID NO | Name |
|---|---|
| 4 | PTHrP propeptide: rsveglsrrl |
| 5 | GH receptor ECD (1-238): FSGSEATAAILSRAPWSLQSVNPGLKTNSSKEPKFTKCRSPERETFSCHWTDEVHHGTKNLGPIQLFYTRRNTQEWTQEWKECPDYVSAGENSCYFNSSFTSIWIPYCIKLTSNGGTVDEKCFSVDEIVQPDPPIALNWTLLNVSLTGIHADIQVRWEAPRNADIQKGWMVLEYELQYKEVNETKWKMMDPILTTSVPVYSLKVDKEYEVRVRSKQRNSGNYGEFSEVLYVTLPQMSQ |
| 7 | GH ECD substitution: w104a substitution FSGSEATAAILSRAPWSLQSVNPGLKTNSSKEPKFTKCRSPERETFSCHWTDEVHHGTKNLGPIQLFYTRRNTQEWTQEWKECPDYVSAGENSCYFNSSFTSIAIPYCIKLTSNGGTVDEKCFSVDEIVQPDPPIALNWTLLNVSLTGIHADIQVRWEAPRNADIQKGWMVLEYELQYKEVNETKWKMMDPILTTSVPVYSLKVDKEYEVRVRSKQRNSGNYGEFSEVLYVTLPQMSQ |
| 8 | PTH formula (I): general AA formula (1-36) |
| 9 | PTH 1-84: SVSEIQLMHNLGKHLNSMERVEWLRKKLQDVHNFVALGAPLAPRDAGSQRPRKKEDNVLVESHEKSLGEADKADVNVLTKAKSQ |
| 10 | PTH defined formula (I): Ala-Val-Ala-Glu-Ile-Gln-Leu-Met-His-Gln-Arg-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile, or a fragment thereof including amino acids 1-28, 1-29, 1-30, 1-31, 1-32, 1-33, 1-34, or 1-35 of said sequence. (1-36) |
| 11 | PTH Propeptide: ksvkkr |
| 12-36 | Constructs of table 1 |
| 37 | PTH short (LA PTH): LA-PTH ([Ala1, 3, 12, Gln10, Arg11, Trp14]PTH(1-14)/[Ala18, 22, Lys26]PTHrP(15-36)COOH) |
| 40 | PTHrP (1-36): AVSEHQLLHDKGKSIQDLRRRFFLHHLIAEIHTAEI |
| 41 | PTHrP signal sequence: MQRRLVQQWSVAVFLLSYAVPSCG |
| 42-52 | Constructs of table 2 |
| 54 | PTH 1-34: SVSEIQLMHNLGKHLNSMERVEWLRKKLQDVHNF |
| 55 | PTH ECD Signal peptide: MGTARIAPGLALLLCCPVLSSAYALVDA |
| 56 | PTH receptor full length: MGTARIAPGLALLLCCPVLSSAYALVDADDVMTKEEQIFLLHRAQAQCEKRLKEVLQRPASIMESDKGWTSASTSGKPRKDKASGKLYPESEEDKEAPTGSRYRGRPCLPEWDHILCWPLGAPGEVVAVPCPDYIYDFNHKGHAYRRCDRNGSWELVPGHNRTWANYSECVKFLTNETREREVFDRLGMIYTVGYSVSLASLTVAVLILAYFRRLHCTRNYIHMHLFLSFMLRAVSIFVKDAVLYSGATLDEAERLTEEELRAIAQAPPPPATAAAGYAGCRVAVTFFLYFLATNYYWILVEGLYSHSLIFMAFFSEKKYLWGFTVFGWGLPAVFVAVWVSVRATLANTGCWDLSSGNKKWIIQVPILASIVLNFILFINIVRVLATKLRETNAGRCDTRQQYRKLLKSTLVLMPLFGVHYIVFMATPYTEVSGTLWQVQMHYEMLFNSFQGFFVAIIYCFCNGEVQAEIKKSWSRWTLALDFKRKARSGSSSYSYGPMVSHTSVTNVGPRVGLGLPLSPRLLPTATTNGHPQLPGHAKPGTPALETLETTPPAMAAPKDDGFLNGSCSGLDEE | ASGPERPPALLQEEWETVM |
| 57 | Fusion of SEQ ID NO: 1, 11 and 9 |
| 58 | DNA sequence encoding SEQ ID NO: 57 |
| 59 | DNA sequence encoding SEQ ID NO: 59 |
| 60 | Fusion of SEQ ID NO: 1 and 11 |
| 61 | DNA sequence encoding SEQ ID NO: 60 |
| 62 | DNA sequence encoding SEQ ID NO: 56 |
| 63 | DNA sequence encoding SEQ ID NO: 3 |
| 64 | DNA sequence encoding SEQ ID NO: 7 |
| 65 | DNA sequence encoding SEQ ID NO: 2 |
| 66 | DNA sequence encoding SEQ ID NO: 12 |
| 67 | DNA sequence encoding SEQ ID NO: 13 |
| 68 | DNA sequence encoding SEQ ID NO: 14 |
| 69 | DNA sequence encoding SEQ ID NO: 15 |
| 70 | DNA sequence encoding SEQ ID NO: 17 |
| 71 | DNA sequence encoding SEQ ID NO: 16 |
| 72 | DNA sequence encoding SEQ ID NO: 18 |
| 73 | DNA sequence encoding SEQ ID NO: 19 |
| 74 | DNA sequence encoding SEQ ID NO: 20 |
| 75 | DNA sequence encoding SEQ ID NO: 21 |
| 39 | DNA sequence encoding SEQ ID NO: 22 |
| 38 | DNA sequence encoding SEQ ID NO: 23 |
| 6 | DNA sequence encoding SEQ ID NO: 24 |

Materials and Methods

Construction of PTH Fusions:

Molecules were constructed by a combination of gene synthesis (Eurofin MWG) and standard DNA manipulation techniques. Recombinant genes encoding full length PTH fusions were cloned into a modified mammalian expression plasmid, pSecTag/FRT/V5/Hist-TOPO (Invitrogen). Stable cell lines were produced in the CHO Flp-In cell line (Invitrogen) according to manufacturer's instructions and adapted to serum free media in Hyclone SFM4CHO Utility (Thermo Scientific). PTH fusions were under the secreted expression of either the PTH or GH signal peptides.

Expression and Purification:

Cells were maintained in roller bottle cultures in Hyclone SFM4CHO Utility medium with passaging every 2-3 days, keeping cell densities between $0.25 \times 10^6$ viable cells/ml (VCPM) and $1.5 \times 10^6$ VCPM. For expression studies, roller bottles were seeded at $0.5 \times 10^6$ VCPM and grown at 37° C., 5% $CO_2$ and allowed to reach $1 \times 10^6$ VPCM. Valproic acid was added to a final concentration of 2 mM and the temperature reduced to 31° C. Cells were grown for up to 8-10 days with viability still at ~70% when harvest was clarified by centrifugation at 22,000×g using a Beckman JLA 16-25 rotor for 20 minutes at 4° C. EDTA and Benzamidine-HCl were added to final concentrations of 5 and 10 mM respectively and the medium concentrated using a Vivaflow 200 tangential flow concentrator and stored frozen at −20° C. Target protein was purified from this concentrate by anion exchange (Q-Sepharose FF, GE Healthcare) and affinity chromatography (anti GHBP antibody column). Protein concentrations were measured by Bradford protein assay and samples analysed by SDS-PAGE under non-reducing conditions and either stained with coomassie blue or western blotted using a commercial anti-PTH 1-34 antibody (Abcam 14493) or an in house developed anti GHBP antibody. Purified samples were aliquoted and stored at −80° C.

In Vitro Bioactivity:

Purified proteins were tested for their ability to stimulate cAMP production from the PTH responsive cell line, UMR-106 (rat osteoblastic like cell line). Cells were stimulated for 15 minutes in the presence of test molecules and cAMP levels measured from cell lysates using a cAMP specific Elisa (R&D systems).

Animal Model for Hypoparathyroidism

Shimizu et al have used an animal model for hypoparathyroidism in their studies on LA-PT. In this model rats were thyroparathyroidectomized (TPTX) prior to treatment. Briefly: Surgical TPTX was performed on 6-week-old rats obtained from Charles River Laboratories Japan, Inc. After surgery, pellet food (CE-2; CLEA Japan, Inc., Tokyo, Japan) containing 1.10% calcium and 1.09% phosphate moisturized with tap water was supplied inside each cage for easy access and digestion in sham-operated and TPTX rats. Postsurgical rats exhibiting sCa levels less than 8.0 mg/dL at 5 days after TPTX surgery were selected for subsequent peptide injection studies from the next day.

Example 1

From the crystal structure analysis of PTH with the N-domain PTH receptor [1], the PTH is shown to sit in a groove formed by the N-terminal receptor portion. It is this mode of interaction that is hypothesised to protect PTH from degradation and to create an "inactive pool" of PTH, thus prolonging its biological activity to create a long acting PTH. It is proposed that the new molecules (See FIG. 1) will be fusions between PTH (residues 1-34), the N-terminal PTH receptor domain (PTHrExt, most commonly residues D29-L187 but not restricted to other combinations) and the growth hormone binding protein (GHBP, residues 1-238). GHBP is an inert moiety designed to increase Mw & therefore delay clearance. It will contain a W104A mutation to prevent interaction with GH in the circulation.

Example 2

Initial expression studies showed that we are able to express and purify a PTH fusion molecule from a CHO cell line at sufficient levels (~10 mg/L) to justify further progress. All molecules appear to be intact and >95% pure as judged by SDS-PAGE.

Both PTH fusion molecules so far tested are biologically activity and produce a dose response in an in vitro cAMP assay.

Example 3

PTH1-34 has been fused to growth hormone binding protein (GHbp) with or without the extracellular domain of the PTH receptor (PTHextR). Molecules have then been expressed with either the GH (GHss) or PTH (PTHss) signal sequence and propeptide (pp). Thus, the following 4 molecules have been generated:

```
                                              (SEQ ID NO: 13)
14A2c = PTHss-pp-PTH (1-34)-(g4s)4-PTHrExt-(g4s)4-
GHbp
                                              (SEQ ID NO: 14)
14A3b = GHss-PTH (1-34)-(g4s)4-PTHrExt-(g4s)4-GHbp
                                              (SEQ ID NO: 15)
14A4  = GHss-PTH (1-34)-(g4s)4-GHbp
                                              (SEQ ID NO: 20)
14A7  = PTHss-pp-PTH(1-34)-(g4s)4-GHbp
```

Figure 28A:
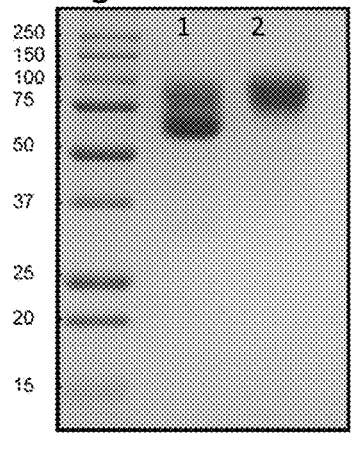
FIGS. 28A, 28B, and 29C: Analysis of purified PTH fusion molecules by 10% SDS-PAGE under non-reducing conditions (Coomassie Stained).
Figure 28B:
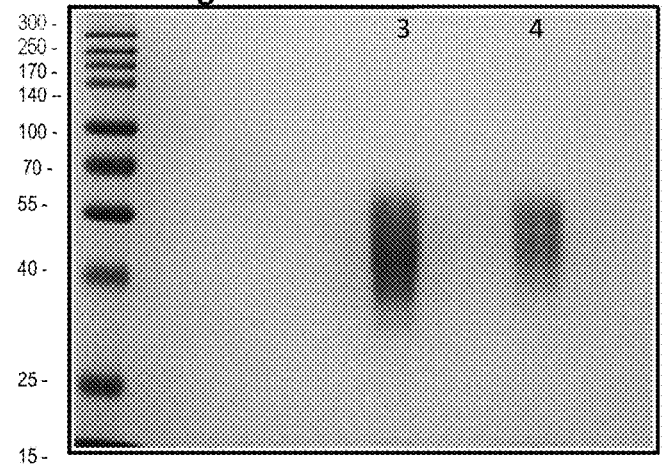
Figure 28C:
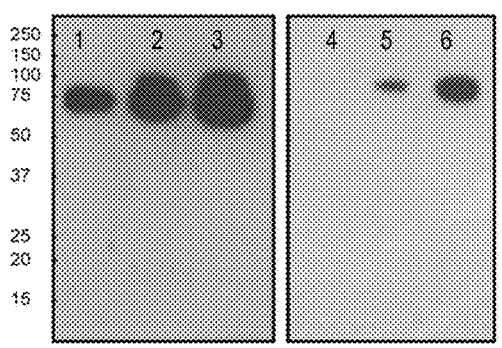
FIG. 28C: Western blot anti PTH 14A2c & 14A3b. Analysis of purified PTH fusion molecules by 10% SDS-PAGE under non-reducing conditions. Samples were transferred to a PVDF membrane and probed with anti-human PTH (1-34) specific antibody. Lanes 1-3: 14A2c at a loading of 125 ng, 250 ng and 500 ng. Lanes 4-6: 14A3b at a loading of 125 ng, 250 ng and 500 ng. 14A2c is more sensitive to detection by anti-PTH antibody. Representative of 3 independent western blot experiments.
Figure 29A:
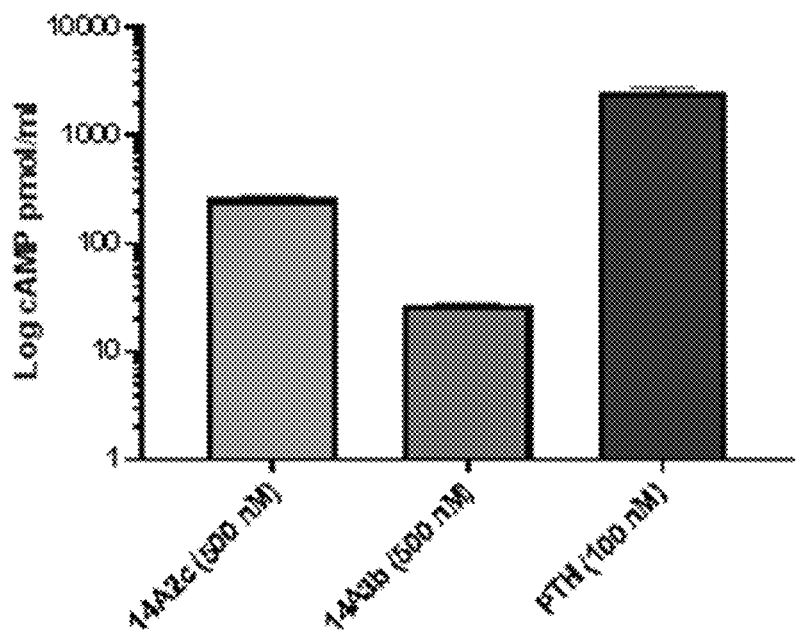
FIG. 29A: In vitro induction of cAMP. UMR-106 cells were challenged with either 500 nM PTH fusion or 100 nM human PTH 1-34 for 15 minutes at 37° C./5% $CO_2$. Cells were lysed and cAMP levels measured using an R & D systems Parameter cAMP Elisa. Data are presented as log pmol cAMP/ml±SD. An 11-fold increase in cAMP levels was found for 14A2c over 14A3b: mean±SD 264±12 vs 25±0.95 pmol cAMP/ml. Both Fusions showed reduced biological activity when compared to PTH 1-34: mean±SD 2551±186 pmol cAMP/ml. Average of n=1 experiment carried out in duplicate.
Figure 29B:
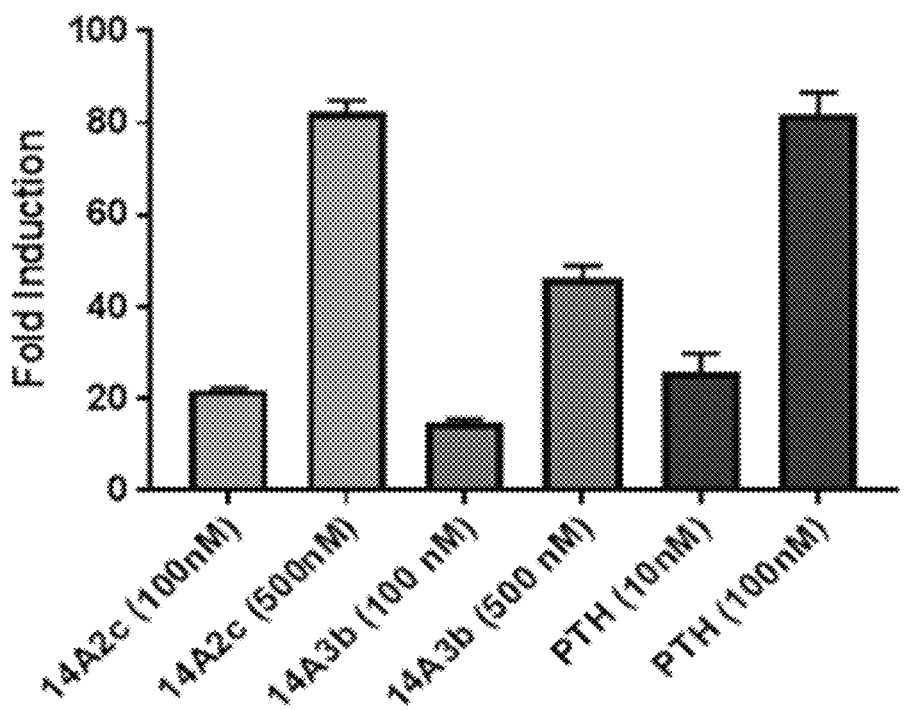
FIG. 29B: Dual Luciferase Reporter Assay for cAMP Activity. UMR-106 cells were transfected with the reporter plasmid pGL4.29/CRE/Luc2/Hygro and transfection control plasmid phRL (*Renilla*) and challenged with either PTH fusion or human PTH 1-34 for 5 hours at 37° C./5% $CO_2$. Cells were lysed and Luciferase activity measured using the Promega Dual Luciferase Assay kit. Data are presented as fold induction of control±SD. 14A2c is more bioactive than 14A3b equating to a ~1.3 to 1.6 fold increase at 100 & 500 nM respectively: mean fold induction±SD, 16.5±1.7, 63±5.9 vs 12.4±1.0, 40.3±3.1. Average of triplicate values. Both Fusions showed reduced biological activity when compared to PTH 1-34 at an equivalent concentration of 100 nM: mean±SD, 67.3±1.6. Representative of 3 separate experiments.
Figure 29C:
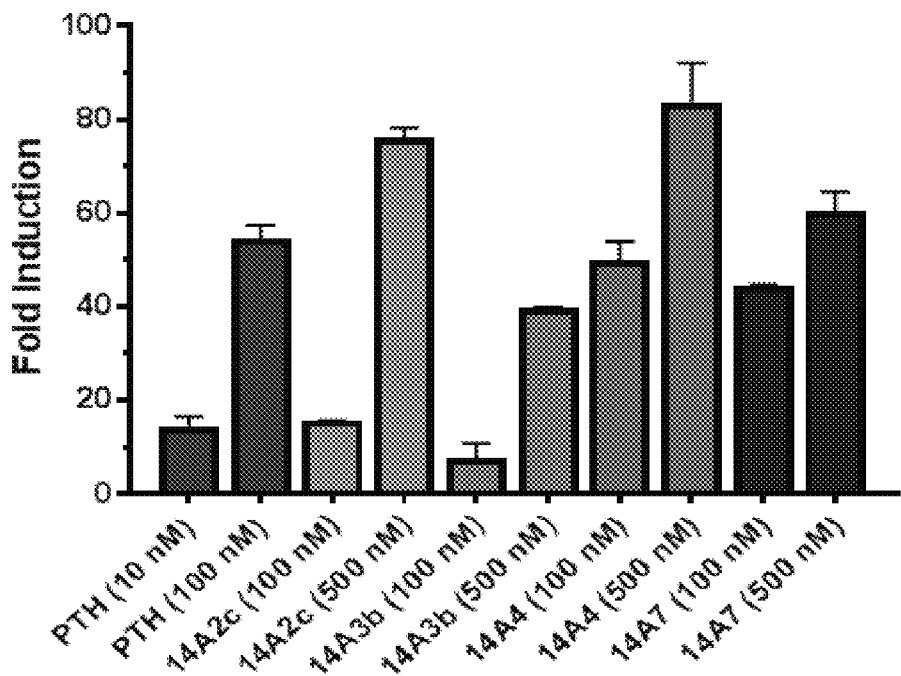
Figure 29D:
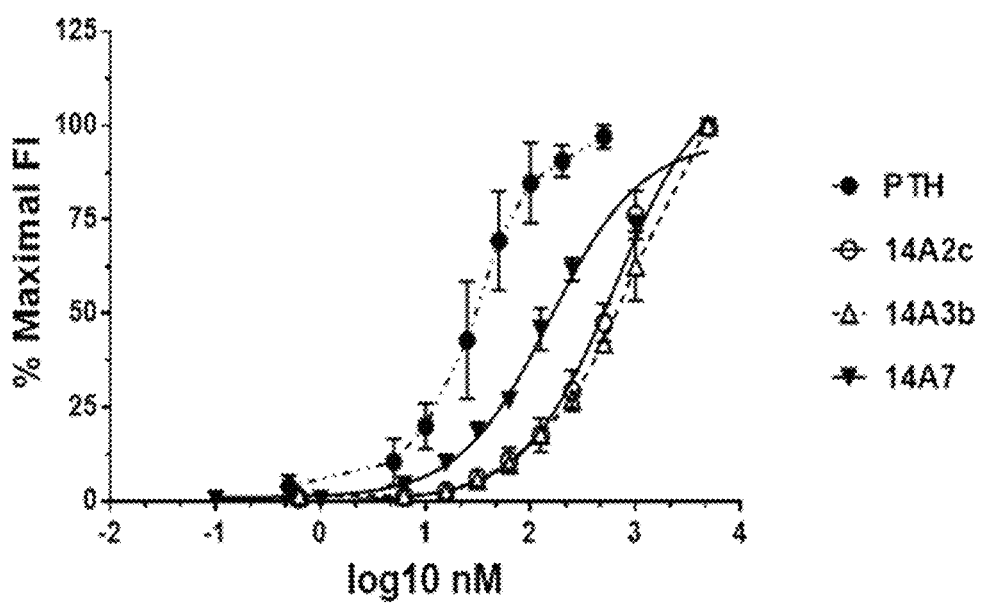
FIG. 29D: Determination of $EC_{50}$ values for PTH & PTH fusions using the Dual Luciferase Reporter Assay. PTH has an $EC_{50}$ of 32±10.67 nM (n=4 experiments) and is ~18-fold more potent than 14A2c ($EC_{50}$=579±138 nM, n=3 experiments), 28-fold more potent than 14A3b ($EO_{50}$=896 nM, n=1), and 4.7-fold more potent than 14A7 ($EO_{50}$=153 nM, n=1 experiment).

Stable clones for all 4 molecules have been generated, all stable clones expressed protein and all 4 proteins have been purified on an affinity column for GHbp. Those using the GHss are expressed at a lower level and SDS-PAGE analysis and bioassays suggest that there may be incomplete processing of the translated product with additional aa at the N-terminus and possibly differential glycosylation of those with the GHss compared to those with the PTHss. (FIG. 28) This would fit with PTH requiring its own signal sequence for complete processing of the preproPTH sequence, which is in the design of the molecules with the PTHss. All molecules show bioactivity in the two bioassays used and evidence suggests that the molecule that includes the PTHextR is less bioactive (FIGS. 29 and 30).

PTH Fusion Molecules: Design & Hypothesis

Parathyroid hormone (PTH) is an 84-aa peptide with biological activity residing in residues 1-34. PTH is produced by the parathyroid glands in response to low serum calcium levels. PTH acts on the parathyroid receptor (PTHR1) on bone and kidney promoting the release of calcium from bone, slowing excretion of calcium from kidneys, increasing absorption from intestines and promoting renal excretion of phosphate. In Hypoparathyroidism (HypoPT) the parathyroid glands are either absent or damaged and therefore cannot produce any or sufficient amounts of parathyroid hormone. Initial treatment is with oral calcium and active VD3 supplements. Recently, replacement of PTH in HypoPT with Natpara (PTH 1-84) has been licensed but requires daily sc injections and is complicated by fluctuating calcium levels. Continuous pump therapy is effective but impractical for most patients. There is therefore an unmet need for a long acting PTH molecule that provides constant physiological levels of PTH activity. Previously we have shown that the fusion of growth hormone to its binding protein (GHBP) can generate a long-acting growth hormone (1). Using this technology we have generated a number of PTH fusion molecules (See FIGS. 1A & B). The PTH fusions are predicted to have a prolonged circulating half-life through increased protein size, whilst retaining biological activity. As a further modification of the PTH fusion shown in FIG. 1A, it is hypothesised that PTH will form intramolecular interactions with PTHrExt, be protected from degradation, and provide an intravascular pool of active PTH. To prevent GH binding, a single amino acid change of tryptophan-104 to alanine in the GHBP moiety (W104A) will be introduced in to all PTH fusion molecules. All PTH fusion will be expressed using either the naturally occurring PTH prepropeptide sequence or the GH secretion signal.

REFERENCES

Shimizu, M., et al., Pharmacodynamic Actions of a Long-Acting PTH Analog (LA-PTH) in Thyroparathyroidectomized (TPTX) Rats and Normal Monkeys. J Bone Miner Res, 2016. 31(7): p. 1405-12

SEQUENCE LISTING

<160> NUMBER OF SEQ ID NOS: 75

<210> SEQ ID NO 1
<211> LENGTH: 25
<212> TYPE: PRT
<213> ORGANISM: artificial sequence
<220> FEATURE:
<223> OTHER INFORMATION: Signal Peptide

<400> SEQUENCE: 1

Met Ile Pro Ala Lys Asp Met Ala Lys Val Met Ile Val Met Leu Ala
1               5                   10                  15

Ile Cys Phe Leu Thr Lys Ser Asp Gly
            20                  25

<210> SEQ ID NO 2
<211> LENGTH: 26
<212> TYPE: PRT
<213> ORGANISM: artificial sequence
<220> FEATURE:
<223> OTHER INFORMATION: Secretion Signal

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 3
<211> LENGTH: 159
<212> TYPE: PRT
<213> ORGANISM: artificial sequence
<220> FEATURE:
<223> OTHER INFORMATION: PTH RECEPTOR ECD 1-159

<400> SEQUENCE: 3

Asp Asp Val Met Thr Lys Glu Glu Gln Ile Phe Leu Leu His Arg Ala
1               5                   10                  15

Gln Ala Gln Cys Glu Lys Arg Leu Lys Glu Val Leu Gln Arg Pro Ala
            20                  25                  30

Ser Ile Met Glu Ser Asp Lys Gly Trp Thr Ser Ala Ser Thr Ser Gly
        35                  40                  45

Lys Pro Arg Lys Asp Lys Ala Ser Gly Lys Leu Tyr Pro Glu Ser Glu
    50                  55                  60

Glu Asp Lys Glu Ala Pro Thr Gly Ser Arg Tyr Arg Gly Arg Pro Cys
65                  70                  75                  80

Leu Pro Glu Trp Asp His Ile Leu Cys Trp Pro Leu Gly Ala Pro Gly
                85                  90                  95

Glu Val Val Ala Val Pro Cys Pro Asp Tyr Ile Tyr Asp Phe Asn His
            100                 105                 110

Lys Gly His Ala Tyr Arg Arg Cys Asp Arg Asn Gly Ser Trp Glu Leu
        115                 120                 125

Val Pro Gly His Asn Arg Thr Trp Ala Asn Tyr Ser Glu Cys Val Lys
    130                 135                 140

Phe Leu Thr Asn Glu Thr Arg Glu Arg Glu Val Phe Asp Arg Leu
145                 150                 155

<210> SEQ ID NO 4
<211> LENGTH: 10
<212> TYPE: PRT
<213> ORGANISM: artificial sequence
<220> FEATURE:
<223> OTHER INFORMATION: PTHrP propetide

<400> SEQUENCE: 4

Arg Ser Val Glu Gly Leu Ser Arg Arg Leu
1               5                   10

<210> SEQ ID NO 5
<211> LENGTH: 238
<212> TYPE: PRT
<213> ORGANISM: artificial sequence
<220> FEATURE:
<223> OTHER INFORMATION: GH receptor ECD 1-238

<400> SEQUENCE: 5

Phe Ser Gly Ser Glu Ala Thr Ala Ala Ile Leu Ser Arg Ala Pro Trp
1               5                   10                  15

Ser Leu Gln Ser Val Asn Pro Gly Leu Lys Thr Asn Ser Ser Lys Glu
                20                  25                  30

Pro Lys Phe Thr Lys Cys Arg Ser Pro Glu Arg Glu Thr Phe Ser Cys
            35                  40                  45

His Trp Thr Asp Glu Val His His Gly Thr Lys Asn Leu Gly Pro Ile
    50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln
225                 230                 235

<210> SEQ ID NO 6
<211> LENGTH: 741
<212> TYPE: DNA
<213> ORGANISM: artificial sequence
<220> FEATURE:
<223> OTHER INFORMATION: Fusion proteins

<400> SEQUENCE: 6
atggctacag gctcccggac gtccctgctc ctggcttttg gcctgctctg cctgccctgg      60
cttcaagagg gcagtgcctc tgtgagtgaa atacagctta tgcataacct gggaaaacat     120
ctgaactcga tggagagagt agaatggctg cgtaagaagc tgcaggatgt gcacaatttt     180

```
ggtggcggag gtagtggtgg cggaggtagc ggtggcggag gttctggtgg cggaggttcc    240
gatgacgtca tgactaaaga ggaacagatc ttcctgctgc accgtgctca ggcccagtgc    300
gaaaaacggc tcaaggaggt cctgcagagg ccagccagca taatggaatc agacaaggga    360
tggacatctg cgtccacatc agggaagccc aggaaagata aggcatctgg gaagctctac    420
cctgagtctg aggaggacaa ggaggcaccc actggcagca ggtaccgagg cgcccctgt     480 ctgccggaat gggaccacat cctgtgctgg ccgctggggg caccaggtga ggtggtggct    540
gtgccctgtc cggactacaa gtatgacttc aatcacaaag gccatgccta ccgacgctgt    600
gaccgcaatg gcagctggga gctggtgcct gggcacaaca ggacgtgggc caactacagc    660
gagtgtgtca aatttctcac caatgagact cgtgaacggg aggtgtttga ccgcctgacc    720
ggtcatcatc accatcacca t                                              741
```

```
<210> SEQ ID NO 7
<211> LENGTH: 238
<212> TYPE: PRT
<213> ORGANISM: artificial sequence
<220> FEATURE:
<223> OTHER INFORMATION: Fusion proteins

<400> SEQUENCE: 7
```

Phe Ser Gly Ser Glu Ala Thr Ala Ala Ile Leu Ser Arg Ala Pro Trp
1               5                   10                  15

Ser Leu Gln Ser Val Asn Pro Gly Leu Lys Thr Asn Ser Ser Lys Glu
            20                  25                  30

Pro Lys Phe Thr Lys Cys Arg Ser Pro Glu Arg Glu Thr Phe Ser Cys
        35                  40                  45

His Trp Thr Asp Glu Val His His Gly Thr Lys Asn Leu Gly Pro Ile
    50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Ala Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln
225                 230                 235

```
<210> SEQ ID NO 8
<211> LENGTH: 36
<212> TYPE: PRT
```

```
<213> ORGANISM: artificial sequence
<220> FEATURE:
<223> OTHER INFORMATION: Fusion proteins
<220> FEATURE:
<221> NAME/KEY: X
<222> LOCATION: (1)..(1)
<223> OTHER INFORMATION: wherein X is Ser or Ala
<220> FEATURE:
<221> NAME/KEY: X
<222> LOCATION: (1)..(35)
<223> OTHER INFORMATION: or a fragment thereof including amino acids
      1-28, 1- 29, 1-30, 1-31 , 1-32, 1-33, 1 -34, or 1-35 of SEQ ID NO
      8, with the proviso that at least one of Xaa18 is not Leu or Met,
      Xaa22 is not Phe, and Xaa26 is not His.
<220> FEATURE:
<221> NAME/KEY: X
<222> LOCATION: (3)..(3)
<223> OTHER INFORMATION: wherein X is Ser or Ala
<220> FEATURE:
<221> NAME/KEY: X
<222> LOCATION: (8)..(8)
<223> OTHER INFORMATION: wherein X is Met or Leu
<220> FEATURE:
<221> NAME/KEY: X
<222> LOCATION: (10)..(10)
<223> OTHER INFORMATION: wherein X is Asn, Ala, Val, Asp, Glu, or Gln
<220> FEATURE:
<221> NAME/KEY: X
<222> LOCATION: (12)..(12)
<223> OTHER INFORMATION: wherein X is Gly, Ala, His, or Arg
<220> FEATURE:
<221> NAME/KEY: X
<222> LOCATION: (13)..(13)
<223> OTHER INFORMATION: wherein X is Lys, Ala, Leu, Gln, Arg, His, or
      Trp
<220> FEATURE:
<221> NAME/KEY: X
<222> LOCATION: (14)..(14)
<223> OTHER INFORMATION: wherein X is His, Leu, Arg, Phe, Trp, or Ser
<220> FEATURE:
<221> NAME/KEY: X
<222> LOCATION: (16)..(16)
<223> OTHER INFORMATION: wherein X is Gln and Asn
<220> FEATURE:
<221> NAME/KEY: X
<222> LOCATION: (17)..(17)
<223> OTHER INFORMATION: wherein X is Asp or Ser
<220> FEATURE:
<221> NAME/KEY: X
<222> LOCATION: (18)..(18)
<223> OTHER INFORMATION: wherein X is Ala, Leu, Met, Glu, Ser, or Phe
<220> FEATURE:
<221> NAME/KEY: X
<222> LOCATION: (22)..(22)
<223> OTHER INFORMATION: wherein X is Ala, Phe, Glu, Ser, Leu, Asn, Trp,
      or Lys
<220> FEATURE:
<221> NAME/KEY: X
<222> LOCATION: (26)..(26)
<223> OTHER INFORMATION: wherein X is Lys, His, Ala, Ser, Asn, or Arg

<400> SEQUENCE: 8

Xaa Val Xaa Glu Ile Gln Leu Xaa His Xaa Xaa Xaa Xaa Xaa Leu Xaa
1               5                   10                  15

Xaa Xaa Arg Arg Arg Xaa Phe Leu Xaa Xaa Leu Ile Ala Glu Ile His
            20                  25                  30

Thr Ala Glu Ile
        35

<210> SEQ ID NO 9
<211> LENGTH: 84
<212> TYPE: PRT
<213> ORGANISM: artificial sequence
<220> FEATURE:
<223> OTHER INFORMATION: Fusion proteins
```

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 10
<211> LENGTH: 36
<212> TYPE: PRT
<213> ORGANISM: artificial sequence
<220> FEATURE:
<223> OTHER INFORMATION: Fusion proteins

<400> SEQUENCE: 10

Ala Val Ala Glu Ile Gln Leu Met His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 11
<211> LENGTH: 6
<212> TYPE: PRT
<213> ORGANISM: artificial sequence
<220> FEATURE:
<223> OTHER INFORMATION: PTH propeptide

<400> SEQUENCE: 11

Lys Ser Val Lys Lys Arg
1               5

<210> SEQ ID NO 12
<211> LENGTH: 496
<212> TYPE: PRT
<213> ORGANISM: artificial sequence
<220> FEATURE:
<223> OTHER INFORMATION: Fusion proteins

<400> SEQUENCE: 12

Met Ile Pro Ala Lys Asp Met Ala Lys Val Met Ile Val Met Leu Ala
1               5                   10                  15

Ile Cys Phe Leu Thr Lys Ser Asp Gly Ser Val Ser Glu Ile Gln Leu
            20                  25                  30

Met His Asn Leu Gly Lys His Leu Asn Ser Met Glu Arg Val Glu Trp
        35                  40                  45

Leu Arg Lys Lys Leu Gln Asp Val His Asn Phe Gly Gly Gly Gly Ser
    50                  55                  60

Gly Gly Gly Gly Ser Gly Gly Gly Ser Gly Gly Gly Gly Ser Asp
65                  70                  75                  80

Asp Val Met Thr Lys Glu Glu Gln Ile Phe Leu Leu His Arg Ala Gln
                85                  90                  95

```
Ala Gln Cys Glu Lys Arg Leu Lys Glu Val Leu Gln Arg Pro Ala Ser
            100                 105                 110

Ile Met Glu Ser Asp Lys Gly Trp Thr Ser Ala Ser Thr Ser Gly Lys
            115                 120                 125

Pro Arg Lys Asp Lys Ala Ser Gly Lys Leu Tyr Pro Glu Ser Glu Glu
        130                 135                 140

Asp Lys Glu Ala Pro Thr Gly Ser Arg Tyr Arg Gly Arg Pro Cys Leu
145                 150                 155                 160

Pro Glu Trp Asp His Ile Leu Cys Trp Pro Leu Gly Ala Pro Gly Glu
                165                 170                 175

Val Val Ala Val Pro Cys Pro Asp Tyr Ile Tyr Asp Phe Asn His Lys
            180                 185                 190

Gly His Ala Tyr Arg Arg Cys Asp Arg Asn Gly Ser Trp Glu Leu Val
        195                 200                 205

Pro Gly His Asn Arg Thr Trp Ala Asn Tyr Ser Glu Cys Val Lys Phe
    210                 215                 220

Leu Thr Asn Glu Thr Arg Glu Arg Glu Val Phe Asp Arg Leu Gly Gly
225                 230                 235                 240

Gly Gly Ser Gly Gly Gly Ser Gly Gly Gly Ser Gly Gly Gly
                245                 250                 255

Gly Ser Phe Ser Gly Ser Glu Ala Thr Ala Ala Ile Leu Ser Arg Ala
                260                 265                 270

Pro Trp Ser Leu Gln Ser Val Asn Pro Gly Leu Lys Thr Asn Ser Ser
            275                 280                 285

Lys Glu Pro Lys Phe Thr Lys Cys Arg Ser Pro Glu Arg Glu Thr Phe
        290                 295                 300

Ser Cys His Trp Thr Asp Glu Val His Gly Thr Lys Asn Leu Gly
305                 310                 315                 320

Pro Ile Gln Leu Phe Tyr Thr Arg Arg Asn Thr Gln Glu Trp Thr Gln
                325                 330                 335

Glu Trp Lys Glu Cys Pro Asp Tyr Val Ser Ala Gly Glu Asn Ser Cys
            340                 345                 350

Tyr Phe Asn Ser Ser Phe Thr Ser Ile Ala Ile Pro Tyr Cys Ile Lys
        355                 360                 365

Leu Thr Ser Asn Gly Gly Thr Val Asp Glu Lys Cys Phe Ser Val Asp
    370                 375                 380

Glu Ile Val Gln Pro Asp Pro Ile Ala Leu Asn Trp Thr Leu Leu
385                 390                 395                 400

Asn Val Ser Leu Thr Gly Ile His Ala Asp Ile Gln Val Arg Trp Glu
                405                 410                 415

Ala Pro Arg Asn Ala Asp Ile Gln Lys Gly Trp Met Val Leu Glu Tyr
            420                 425                 430

Glu Leu Gln Tyr Lys Glu Val Asn Glu Thr Lys Trp Lys Met Met Asp
        435                 440                 445

Pro Ile Leu Thr Thr Ser Val Pro Val Tyr Ser Leu Lys Val Asp Lys
    450                 455                 460

Glu Tyr Glu Val Arg Val Arg Ser Lys Gln Arg Asn Ser Gly Asn Tyr
465                 470                 475                 480

Gly Glu Phe Ser Glu Val Leu Tyr Val Thr Leu Pro Gln Met Ser Gln
                485                 490                 495

<210> SEQ ID NO 13
<211> LENGTH: 502
```

```
<212> TYPE: PRT
<213> ORGANISM: artificial sequence
<220> FEATURE:
<223> OTHER INFORMATION: Fusion proteins

<400> SEQUENCE: 13

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
    50                  55                  60

Phe Gly Gly Gly Gly Ser Gly Gly Gly Ser Gly Gly Gly Gly Ser
65                  70                  75                  80

Gly Gly Gly Gly Ser Asp Asp Val Met Thr Lys Glu Glu Gln Ile Phe
                85                  90                  95

Leu Leu His Arg Ala Gln Ala Gln Cys Glu Lys Arg Leu Lys Glu Val
            100                 105                 110

Leu Gln Arg Pro Ala Ser Ile Met Glu Ser Asp Lys Gly Trp Thr Ser
        115                 120                 125

Ala Ser Thr Ser Gly Lys Pro Arg Lys Asp Lys Ala Ser Gly Lys Leu
    130                 135                 140

Tyr Pro Glu Ser Glu Glu Asp Lys Glu Ala Pro Thr Gly Ser Arg Tyr
145                 150                 155                 160

Arg Gly Arg Pro Cys Leu Pro Glu Trp Asp His Ile Leu Cys Trp Pro
                165                 170                 175

Leu Gly Ala Pro Gly Glu Val Val Ala Val Pro Cys Pro Asp Tyr Ile
            180                 185                 190

Tyr Asp Phe Asn His Lys Gly His Ala Tyr Arg Arg Cys Asp Arg Asn
        195                 200                 205

Gly Ser Trp Glu Leu Val Pro Gly His Asn Arg Thr Trp Ala Asn Tyr
    210                 215                 220

Ser Glu Cys Val Lys Phe Leu Thr Asn Glu Thr Arg Glu Arg Glu Val
225                 230                 235                 240

Phe Asp Arg Leu Gly Gly Gly Ser Gly Gly Gly Gly Ser Gly Gly
                245                 250                 255

Gly Gly Ser Gly Gly Gly Ser Phe Ser Gly Ser Glu Ala Thr Ala
            260                 265                 270

Ala Ile Leu Ser Arg Ala Pro Trp Ser Leu Gln Ser Val Asn Pro Gly
        275                 280                 285

Leu Lys Thr Asn Ser Ser Lys Glu Pro Lys Phe Thr Lys Cys Arg Ser
    290                 295                 300

Pro Glu Arg Glu Thr Phe Ser Cys His Trp Thr Asp Glu Val His His
305                 310                 315                 320

Gly Thr Lys Asn Leu Gly Pro Ile Gln Leu Phe Tyr Thr Arg Arg Asn
                325                 330                 335

Thr Gln Glu Trp Thr Gln Glu Trp Lys Glu Cys Pro Asp Tyr Val Ser
            340                 345                 350

Ala Gly Glu Asn Ser Cys Tyr Phe Asn Ser Ser Phe Thr Ser Ile Ala
        355                 360                 365

Ile Pro Tyr Cys Ile Lys Leu Thr Ser Asn Gly Gly Thr Val Asp Glu
    370                 375                 380
```

```
Lys Cys Phe Ser Val Asp Glu Ile Val Gln Pro Asp Pro Pro Ile Ala
385                 390                 395                 400

Leu Asn Trp Thr Leu Leu Asn Val Ser Leu Thr Gly Ile His Ala Asp
            405                 410                 415

Ile Gln Val Arg Trp Glu Ala Pro Arg Asn Ala Asp Ile Gln Lys Gly
            420                 425                 430

Trp Met Val Leu Glu Tyr Glu Leu Gln Tyr Lys Glu Val Asn Glu Thr
            435                 440                 445

Lys Trp Lys Met Met Asp Pro Ile Leu Thr Thr Ser Val Pro Val Tyr
450                 455                 460

Ser Leu Lys Val Asp Lys Glu Tyr Glu Val Arg Val Arg Ser Lys Gln
465                 470                 475                 480

Arg Asn Ser Gly Asn Tyr Gly Glu Phe Ser Glu Val Leu Tyr Val Thr
            485                 490                 495

Leu Pro Gln Met Ser Gln
            500

<210> SEQ ID NO 14
<211> LENGTH: 497
<212> TYPE: PRT
<213> ORGANISM: artificial sequence
<220> FEATURE:
<223> OTHER INFORMATION: Fusion proteins

<400> SEQUENCE: 14

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
            20                  25                  30

Leu Met His Asn Leu Gly Lys His Leu Asn Ser Met Glu Arg Val Glu
        35                  40                  45

Trp Leu Arg Lys Lys Leu Gln Asp Val His Asn Phe Gly Gly Gly Gly
    50                  55                  60

Ser Gly Gly Gly Gly Ser Gly Gly Gly Gly Ser Gly Gly Gly Gly Ser
65                  70                  75                  80

Asp Asp Val Met Thr Lys Glu Glu Gln Ile Phe Leu Leu His Arg Ala
            85                  90                  95

Gln Ala Gln Cys Glu Lys Arg Leu Lys Glu Val Leu Gln Arg Pro Ala
            100                 105                 110

Ser Ile Met Glu Ser Asp Lys Gly Trp Thr Ser Ala Ser Thr Ser Gly
            115                 120                 125

Lys Pro Arg Lys Asp Lys Ala Ser Gly Lys Leu Tyr Pro Glu Ser Glu
            130                 135                 140

Glu Asp Lys Glu Ala Pro Thr Gly Ser Arg Tyr Arg Gly Arg Pro Cys
145                 150                 155                 160

Leu Pro Glu Trp Asp His Ile Leu Cys Trp Pro Leu Gly Ala Pro Gly
            165                 170                 175

Glu Val Val Ala Val Pro Cys Pro Asp Tyr Ile Tyr Asp Phe Asn His
            180                 185                 190

Lys Gly His Ala Tyr Arg Arg Cys Asp Arg Asn Gly Ser Trp Glu Leu
            195                 200                 205

Val Pro Gly His Asn Arg Thr Trp Ala Asn Tyr Ser Glu Cys Val Lys
            210                 215                 220

Phe Leu Thr Asn Glu Thr Arg Glu Arg Glu Val Phe Asp Arg Leu Gly
225                 230                 235                 240
```

```
Gly Gly Gly Ser Gly Gly Gly Ser Gly Gly Gly Ser Gly Gly
                245                 250                 255

Gly Gly Ser Phe Ser Gly Ser Glu Ala Thr Ala Ala Ile Leu Ser Arg
            260                 265                 270

Ala Pro Trp Ser Leu Gln Ser Val Asn Pro Gly Leu Lys Thr Asn Ser
            275                 280                 285

Ser Lys Glu Pro Lys Phe Thr Lys Cys Arg Ser Pro Glu Arg Glu Thr
290                 295                 300

Phe Ser Cys His Trp Thr Asp Glu Val His His Gly Thr Lys Asn Leu
305                 310                 315                 320

Gly Pro Ile Gln Leu Phe Tyr Thr Arg Arg Asn Thr Gln Glu Trp Thr
                325                 330                 335

Gln Glu Trp Lys Glu Cys Pro Asp Tyr Val Ser Ala Gly Glu Asn Ser
            340                 345                 350

Cys Tyr Phe Asn Ser Ser Phe Thr Ser Ile Ala Ile Pro Tyr Cys Ile
            355                 360                 365

Lys Leu Thr Ser Asn Gly Gly Thr Val Asp Glu Lys Cys Phe Ser Val
            370                 375                 380

Asp Glu Ile Val Gln Pro Asp Pro Pro Ile Ala Leu Asn Trp Thr Leu
385                 390                 395                 400

Leu Asn Val Ser Leu Thr Gly Ile His Ala Asp Ile Gln Val Arg Trp
                405                 410                 415

Glu Ala Pro Arg Asn Ala Asp Ile Gln Lys Gly Trp Met Val Leu Glu
            420                 425                 430

Tyr Glu Leu Gln Tyr Lys Glu Val Asn Glu Thr Lys Trp Lys Met Met
            435                 440                 445

Asp Pro Ile Leu Thr Thr Ser Val Pro Val Tyr Ser Leu Lys Val Asp
450                 455                 460

Lys Glu Tyr Glu Val Arg Val Arg Ser Lys Gln Arg Asn Ser Gly Asn
465                 470                 475                 480

Tyr Gly Glu Phe Ser Glu Val Leu Tyr Val Thr Leu Pro Gln Met Ser
                485                 490                 495

Gln

<210> SEQ ID NO 15
<211> LENGTH: 318
<212> TYPE: PRT
<213> ORGANISM: artificial sequence
<220> FEATURE:
<223> OTHER INFORMATION: Fusion proteins

<400> SEQUENCE: 15

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
            20                  25                  30

Leu Met His Asn Leu Gly Lys His Leu Asn Ser Met Glu Arg Val Glu
        35                  40                  45

Trp Leu Arg Lys Lys Leu Gln Asp Val His Asn Phe Gly Gly Gly Gly
    50                  55                  60

Ser Gly Gly Gly Gly Ser Gly Gly Gly Gly Ser Gly Gly Gly Gly Ser
65                  70                  75                  80

Phe Ser Gly Ser Glu Ala Thr Ala Ala Ile Leu Ser Arg Ala Pro Trp
                85                  90                  95

Ser Leu Gln Ser Val Asn Pro Gly Leu Lys Thr Asn Ser Ser Lys Glu
```

```
                100                 105                 110
Pro Lys Phe Thr Lys Cys Arg Ser Pro Glu Arg Glu Thr Phe Ser Cys
            115                 120                 125

His Trp Thr Asp Glu Val His His Gly Thr Lys Asn Leu Gly Pro Ile
        130                 135                 140

Gln Leu Phe Tyr Thr Arg Arg Asn Thr Gln Glu Trp Thr Gln Glu Trp
145                 150                 155                 160

Lys Glu Cys Pro Asp Tyr Val Ser Ala Gly Glu Asn Ser Cys Tyr Phe
                165                 170                 175

Asn Ser Ser Phe Thr Ser Ile Ala Ile Pro Tyr Cys Ile Lys Leu Thr
            180                 185                 190

Ser Asn Gly Gly Thr Val Asp Glu Lys Cys Phe Ser Val Asp Glu Ile
        195                 200                 205

Val Gln Pro Asp Pro Ile Ala Leu Asn Trp Thr Leu Leu Asn Val
    210                 215                 220

Ser Leu Thr Gly Ile His Ala Asp Ile Gln Val Arg Trp Glu Ala Pro
225                 230                 235                 240

Arg Asn Ala Asp Ile Gln Lys Gly Trp Met Val Leu Glu Tyr Glu Leu
                245                 250                 255

Gln Tyr Lys Glu Val Asn Glu Thr Lys Trp Lys Met Met Asp Pro Ile
            260                 265                 270

Leu Thr Thr Ser Val Pro Val Tyr Ser Leu Lys Val Asp Lys Glu Tyr
        275                 280                 285

Glu Val Arg Val Arg Ser Lys Gln Arg Asn Ser Gly Asn Tyr Gly Glu
    290                 295                 300

Phe Ser Glu Val Leu Tyr Val Thr Leu Pro Gln Met Ser Gln
305                 310                 315

<210> SEQ ID NO 16
<211> LENGTH: 239
<212> TYPE: PRT
<213> ORGANISM: artificial sequence
<220> FEATURE:
<223> OTHER INFORMATION: Fusion proteins

<400> SEQUENCE: 16

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
                20                  25                  30

Leu Met His Asn Leu Gly Lys His Leu Asn Ser Met Glu Arg Val Glu
            35                  40                  45

Trp Leu Arg Lys Lys Leu Gln Asp Val His Asn Phe Gly Gly Gly Gly
        50                  55                  60

Ser Gly Gly Gly Gly Ser Gly Gly Gly Gly Ser Gly Gly Gly Gly Ser
65                  70                  75                  80

Asp Asp Val Met Thr Lys Glu Glu Gln Ile Phe Leu Leu His Arg Ala
                85                  90                  95

Gln Ala Gln Cys Glu Lys Arg Leu Lys Glu Val Leu Gln Arg Pro Ala
            100                 105                 110

Ser Ile Met Glu Ser Asp Lys Gly Trp Thr Ser Ala Ser Thr Ser Gly
        115                 120                 125

Lys Pro Arg Lys Asp Lys Ala Ser Gly Lys Leu Tyr Pro Glu Ser Glu
    130                 135                 140

Glu Asp Lys Glu Ala Pro Thr Gly Ser Arg Tyr Arg Gly Arg Pro Cys
```

```
                145                 150                 155                 160
Leu Pro Glu Trp Asp His Ile Leu Cys Trp Pro Leu Gly Ala Pro Gly
                165                 170                 175

Glu Val Val Ala Val Pro Cys Pro Asp Tyr Ile Tyr Asp Phe Asn His
                180                 185                 190

Lys Gly His Ala Tyr Arg Arg Cys Asp Arg Asn Gly Ser Trp Glu Leu
                195                 200                 205

Val Pro Gly His Asn Arg Thr Trp Ala Asn Tyr Ser Glu Cys Val Lys
                210                 215                 220

Phe Leu Thr Asn Glu Thr Arg Glu Arg Glu Val Phe Asp Arg Leu
225                 230                 235

<210> SEQ ID NO 17
<211> LENGTH: 247
<212> TYPE: PRT
<213> ORGANISM: artificial sequence
<220> FEATURE:
<223> OTHER INFORMATION: Fusion proteins

<400> SEQUENCE: 17

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
                20                  25                  30

Leu Met His Asn Leu Gly Lys His Leu Asn Ser Met Glu Arg Val Glu
                35                  40                  45

Trp Leu Arg Lys Lys Leu Gln Asp Val His Asn Phe Gly Gly Gly Gly
        50                  55                  60

Ser Gly Gly Gly Gly Ser Gly Gly Gly Gly Ser Gly Gly Gly Gly Ser
65                  70                  75                  80

Asp Asp Val Met Thr Lys Glu Glu Gln Ile Phe Leu Leu His Arg Ala
                85                  90                  95

Gln Ala Gln Cys Glu Lys Arg Leu Lys Glu Val Leu Gln Arg Pro Ala
                100                 105                 110

Ser Ile Met Glu Ser Asp Lys Gly Trp Thr Ser Ala Ser Thr Ser Gly
                115                 120                 125

Lys Pro Arg Lys Asp Lys Ala Ser Gly Lys Leu Tyr Pro Glu Ser Glu
                130                 135                 140

Glu Asp Lys Glu Ala Pro Thr Gly Ser Arg Tyr Arg Gly Arg Pro Cys
145                 150                 155                 160

Leu Pro Glu Trp Asp His Ile Leu Cys Trp Pro Leu Gly Ala Pro Gly
                165                 170                 175

Glu Val Val Ala Val Pro Cys Pro Asp Tyr Ile Tyr Asp Phe Asn His
                180                 185                 190

Lys Gly His Ala Tyr Arg Arg Cys Asp Arg Asn Gly Ser Trp Glu Leu
                195                 200                 205

Val Pro Gly His Asn Arg Thr Trp Ala Asn Tyr Ser Glu Cys Val Lys
                210                 215                 220

Phe Leu Thr Asn Glu Thr Arg Glu Arg Glu Val Phe Asp Arg Leu Thr
225                 230                 235                 240

Gly His His His His His His
                245

<210> SEQ ID NO 18
<211> LENGTH: 252
<212> TYPE: PRT
```

<213> ORGANISM: artificial sequence
<220> FEATURE:
<223> OTHER INFORMATION: Fusion proteins

<400> SEQUENCE: 18

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
    50                  55                  60

Phe Gly Gly Gly Gly Ser Gly Gly Gly Ser Gly Gly Gly Gly Ser
65                  70                  75                  80

Gly Gly Gly Gly Ser Asp Asp Val Met Thr Lys Glu Glu Gln Ile Phe
                85                  90                  95

Leu Leu His Arg Ala Gln Ala Gln Cys Glu Lys Arg Leu Lys Glu Val
            100                 105                 110

Leu Gln Arg Pro Ala Ser Ile Met Glu Ser Asp Lys Gly Trp Thr Ser
        115                 120                 125

Ala Ser Thr Ser Gly Lys Pro Arg Lys Asp Lys Ala Ser Gly Lys Leu
    130                 135                 140

Tyr Pro Glu Ser Glu Glu Asp Lys Glu Ala Pro Thr Gly Ser Arg Tyr
145                 150                 155                 160

Arg Gly Arg Pro Cys Leu Pro Glu Trp Asp His Ile Leu Cys Trp Pro
                165                 170                 175

Leu Gly Ala Pro Gly Glu Val Val Ala Val Pro Cys Pro Asp Tyr Ile
            180                 185                 190

Tyr Asp Phe Asn His Lys Gly His Ala Tyr Arg Arg Cys Asp Arg Asn
        195                 200                 205

Gly Ser Trp Glu Leu Val Pro Gly His Asn Arg Thr Trp Ala Asn Tyr
    210                 215                 220

Ser Glu Cys Val Lys Phe Leu Thr Asn Glu Thr Arg Glu Arg Glu Val
225                 230                 235                 240

Phe Asp Arg Leu Thr Gly His His His His His
                245                 250

<210> SEQ ID NO 19
<211> LENGTH: 244
<212> TYPE: PRT
<213> ORGANISM: artificial sequence
<220> FEATURE:
<223> OTHER INFORMATION: Fusion proteins

<400> SEQUENCE: 19

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
    50                  55                  60

Phe Gly Gly Gly Gly Ser Gly Gly Gly Ser Gly Gly Gly Gly Ser
65                  70                  75                  80

```
Gly Gly Gly Gly Ser Asp Asp Val Met Thr Lys Glu Glu Gln Ile Phe
            85                  90                  95

Leu Leu His Arg Ala Gln Ala Gln Cys Glu Lys Arg Leu Lys Glu Val
            100                 105                 110

Leu Gln Arg Pro Ala Ser Ile Met Glu Ser Asp Lys Gly Trp Thr Ser
            115                 120                 125

Ala Ser Thr Ser Gly Lys Pro Arg Lys Asp Lys Ala Ser Gly Lys Leu
        130                 135                 140

Tyr Pro Glu Ser Glu Glu Asp Lys Glu Ala Pro Thr Gly Ser Arg Tyr
145                 150                 155                 160

Arg Gly Arg Pro Cys Leu Pro Glu Trp Asp His Ile Leu Cys Trp Pro
                    165                 170                 175

Leu Gly Ala Pro Gly Glu Val Val Ala Val Pro Cys Pro Asp Tyr Ile
                180                 185                 190

Tyr Asp Phe Asn His Lys Gly His Ala Tyr Arg Arg Cys Asp Arg Asn
            195                 200                 205

Gly Ser Trp Glu Leu Val Pro Gly His Asn Arg Thr Trp Ala Asn Tyr
        210                 215                 220

Ser Glu Cys Val Lys Phe Leu Thr Asn Glu Thr Arg Glu Arg Glu Val
225                 230                 235                 240

Phe Asp Arg Leu

<210> SEQ ID NO 20
<211> LENGTH: 323
<212> TYPE: PRT
<213> ORGANISM: artificial sequence
<220> FEATURE:
<223> OTHER INFORMATION: Fusion proteins

<400> SEQUENCE: 20

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Gly Gly Gly Gly Ser Gly Gly Gly Gly Ser Gly Gly Gly Gly Ser
65                  70                  75                  80

Gly Gly Gly Gly Ser Phe Ser Gly Ser Glu Ala Thr Ala Ala Ile Leu
            85                  90                  95

Ser Arg Ala Pro Trp Ser Leu Gln Ser Val Asn Pro Gly Leu Lys Thr
            100                 105                 110

Asn Ser Ser Lys Glu Pro Lys Phe Thr Lys Cys Arg Ser Pro Glu Arg
            115                 120                 125

Glu Thr Phe Ser Cys His Trp Thr Asp Glu Val His His Gly Thr Lys
            130                 135                 140

Asn Leu Gly Pro Ile Gln Leu Phe Tyr Thr Arg Arg Asn Thr Gln Glu
145                 150                 155                 160

Trp Thr Gln Glu Trp Lys Glu Cys Pro Asp Tyr Val Ser Ala Gly Glu
                    165                 170                 175

Asn Ser Cys Tyr Phe Asn Ser Ser Phe Thr Ser Ile Ala Ile Pro Tyr
                180                 185                 190

Cys Ile Lys Leu Thr Ser Asn Gly Gly Thr Val Asp Glu Lys Cys Phe
```

```
                195                 200                 205
Ser Val Asp Glu Ile Val Gln Pro Asp Pro Ile Ala Leu Asn Trp
210                 215                 220

Thr Leu Leu Asn Val Ser Leu Thr Gly Ile His Ala Asp Ile Gln Val
225                 230                 235                 240

Arg Trp Glu Ala Pro Arg Asn Ala Asp Ile Gln Lys Gly Trp Met Val
                245                 250                 255

Leu Glu Tyr Glu Leu Gln Tyr Lys Glu Val Asn Glu Thr Lys Trp Lys
                260                 265                 270

Met Met Asp Pro Ile Leu Thr Thr Ser Val Pro Val Tyr Ser Leu Lys
                275                 280                 285

Val Asp Lys Glu Tyr Glu Val Arg Val Arg Ser Lys Gln Arg Asn Ser
290                 295                 300

Gly Asn Tyr Gly Glu Phe Ser Glu Val Leu Tyr Val Thr Leu Pro Gln
305                 310                 315                 320

Met Ser Gln

<210> SEQ ID NO 21
<211> LENGTH: 502
<212> TYPE: PRT
<213> ORGANISM: artificial sequence
<220> FEATURE:
<223> OTHER INFORMATION: Fusion proteins

<400> SEQUENCE: 21

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
                35                  40                  45

Met Glu Arg Val Glu Trp Leu Arg Lys Lys Leu Gln Asp Val His Asn
            50                  55                  60

Phe Gly Gly Gly Ser Gly Gly Gly Ser Gly Gly Gly Gly Ser
65                  70                  75                  80

Gly Gly Gly Gly Ser Asp Asp Val Met Thr Lys Glu Glu Gln Ile Phe
                85                  90                  95

Leu Leu His Arg Ala Gln Ala Gln Cys Glu Lys Arg Leu Lys Glu Val
                100                 105                 110

Leu Gln Arg Pro Ala Ser Ile Met Glu Ser Asp Lys Gly Trp Thr Ser
                115                 120                 125

Ala Ser Thr Ser Gly Lys Pro Arg Lys Asp Lys Ala Ser Gly Lys Leu
            130                 135                 140

Tyr Pro Glu Ser Glu Glu Asp Lys Glu Ala Pro Thr Gly Ser Arg Tyr
145                 150                 155                 160

Arg Gly Arg Pro Cys Leu Pro Glu Trp Asp His Ile Leu Cys Trp Pro
                165                 170                 175

Leu Gly Ala Pro Gly Glu Val Val Ala Val Pro Cys Pro Asp Tyr Lys
                180                 185                 190

Tyr Asp Phe Asn His Lys Gly His Ala Tyr Arg Arg Cys Asp Arg Asn
                195                 200                 205

Gly Ser Trp Glu Leu Val Pro Gly His Asn Arg Thr Trp Ala Asn Tyr
            210                 215                 220

Ser Glu Cys Val Lys Phe Leu Thr Asn Glu Thr Arg Glu Arg Glu Val
225                 230                 235                 240
```

-continued

```
Phe Asp Arg Leu Gly Gly Gly Ser Gly Gly Gly Ser Gly Gly
                245                 250                 255

Gly Gly Ser Gly Gly Gly Ser Phe Ser Gly Ser Glu Ala Thr Ala
            260                 265                 270

Ala Ile Leu Ser Arg Ala Pro Trp Ser Leu Gln Ser Val Asn Pro Gly
            275                 280                 285

Leu Lys Thr Asn Ser Ser Lys Glu Pro Lys Phe Thr Lys Cys Arg Ser
        290                 295                 300

Pro Glu Arg Glu Thr Phe Ser Cys His Trp Thr Asp Glu Val His His
305                 310                 315                 320

Gly Thr Lys Asn Leu Gly Pro Ile Gln Leu Phe Tyr Thr Arg Arg Asn
            325                 330                 335

Thr Gln Glu Trp Thr Gln Glu Trp Lys Glu Cys Pro Asp Tyr Val Ser
            340                 345                 350

Ala Gly Glu Asn Ser Cys Tyr Phe Asn Ser Ser Phe Thr Ser Ile Ala
            355                 360                 365

Ile Pro Tyr Cys Ile Lys Leu Thr Ser Asn Gly Gly Thr Val Asp Glu
        370                 375                 380

Lys Cys Phe Ser Val Asp Glu Ile Val Gln Pro Asp Pro Pro Ile Ala
385                 390                 395                 400

Leu Asn Trp Thr Leu Leu Asn Val Ser Leu Thr Gly Ile His Ala Asp
            405                 410                 415

Ile Gln Val Arg Trp Glu Ala Pro Arg Asn Ala Asp Ile Gln Lys Gly
            420                 425                 430

Trp Met Val Leu Glu Tyr Glu Leu Gln Tyr Lys Glu Val Asn Glu Thr
        435                 440                 445

Lys Trp Lys Met Met Asp Pro Ile Leu Thr Thr Ser Val Pro Val Tyr
    450                 455                 460

Ser Leu Lys Val Asp Lys Glu Tyr Glu Val Arg Val Arg Ser Lys Gln
465                 470                 475                 480

Arg Asn Ser Gly Asn Tyr Gly Glu Phe Ser Glu Val Leu Tyr Val Thr
            485                 490                 495

Leu Pro Gln Met Ser Gln
            500

<210> SEQ ID NO 22
<211> LENGTH: 497
<212> TYPE: PRT
<213> ORGANISM: artificial sequence
<220> FEATURE:
<223> OTHER INFORMATION: Fusion proteins

<400> SEQUENCE: 22

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
            20                  25                  30

Leu Met His Asn Leu Gly Lys His Leu Asn Ser Met Glu Arg Val Glu
        35                  40                  45

Trp Leu Arg Lys Lys Leu Gln Asp Val His Asn Phe Gly Gly Gly Gly
    50                  55                  60

Ser Gly Gly Gly Gly Ser Gly Gly Gly Gly Ser Gly Gly Gly Gly Ser
65                  70                  75                  80

Asp Asp Val Met Thr Lys Glu Glu Gln Ile Phe Leu Leu His Arg Ala
            85                  90                  95
```

-continued

```
Gln Ala Gln Cys Glu Lys Arg Leu Lys Glu Val Leu Gln Arg Pro Ala
            100                 105                 110
Ser Ile Met Glu Ser Asp Lys Gly Trp Thr Ser Ala Thr Ser Gly
        115                 120                 125
Lys Pro Arg Lys Asp Lys Ala Ser Gly Lys Leu Tyr Pro Glu Ser Glu
130                 135                 140
Glu Asp Lys Glu Ala Pro Thr Gly Ser Arg Tyr Arg Gly Arg Pro Cys
145                 150                 155                 160
Leu Pro Glu Trp Asp His Ile Leu Cys Trp Pro Leu Gly Ala Pro Gly
                165                 170                 175
Glu Val Val Ala Val Pro Cys Pro Asp Tyr Lys Tyr Asp Phe Asn His
                180                 185                 190
Lys Gly His Ala Tyr Arg Arg Cys Asp Arg Asn Gly Ser Trp Glu Leu
            195                 200                 205
Val Pro Gly His Asn Arg Thr Trp Ala Asn Tyr Ser Glu Cys Val Lys
        210                 215                 220
Phe Leu Thr Asn Glu Thr Arg Glu Arg Glu Val Phe Asp Arg Leu Gly
225                 230                 235                 240
Gly Gly Gly Ser Gly Gly Gly Ser Gly Gly Gly Ser Gly Gly
                245                 250                 255
Gly Gly Ser Phe Ser Gly Ser Glu Ala Thr Ala Ala Ile Leu Ser Arg
                260                 265                 270
Ala Pro Trp Ser Leu Gln Ser Val Asn Pro Gly Leu Lys Thr Asn Ser
                275                 280                 285
Ser Lys Glu Pro Lys Phe Thr Lys Cys Arg Ser Pro Glu Arg Glu Thr
            290                 295                 300
Phe Ser Cys His Trp Thr Asp Glu Val His His Gly Thr Lys Asn Leu
305                 310                 315                 320
Gly Pro Ile Gln Leu Phe Tyr Thr Arg Arg Asn Thr Gln Glu Trp Thr
                325                 330                 335
Gln Glu Trp Lys Glu Cys Pro Asp Tyr Val Ser Ala Gly Glu Asn Ser
                340                 345                 350
Cys Tyr Phe Asn Ser Ser Phe Thr Ser Ile Ala Ile Pro Tyr Cys Ile
            355                 360                 365
Lys Leu Thr Ser Asn Gly Gly Thr Val Asp Glu Lys Cys Phe Ser Val
        370                 375                 380
Asp Glu Ile Val Gln Pro Asp Pro Pro Ile Ala Leu Asn Trp Thr Leu
385                 390                 395                 400
Leu Asn Val Ser Leu Thr Gly Ile His Ala Asp Ile Gln Val Arg Trp
                405                 410                 415
Glu Ala Pro Arg Asn Ala Asp Ile Gln Lys Gly Trp Met Val Leu Glu
                420                 425                 430
Tyr Glu Leu Gln Tyr Lys Glu Val Asn Glu Thr Lys Trp Lys Met Met
            435                 440                 445
Asp Pro Ile Leu Thr Thr Ser Val Pro Val Tyr Ser Leu Lys Val Asp
            450                 455                 460
Lys Glu Tyr Glu Val Arg Val Arg Ser Lys Gln Arg Asn Ser Gly Asn
465                 470                 475                 480
Tyr Gly Glu Phe Ser Glu Val Leu Tyr Val Thr Leu Pro Gln Met Ser
                485                 490                 495
Gln
```

```
<210> SEQ ID NO 23
<211> LENGTH: 252
<212> TYPE: PRT
<213> ORGANISM: artificial sequence
<220> FEATURE:
<223> OTHER INFORMATION: Fusion proteins

<400> SEQUENCE: 23

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Gly Gly Gly Gly Ser Gly Gly Gly Ser Gly Gly Gly Gly Ser
65                  70                  75                  80

Gly Gly Gly Gly Ser Asp Asp Val Met Thr Lys Glu Glu Gln Ile Phe
                85                  90                  95

Leu Leu His Arg Ala Gln Ala Gln Cys Glu Lys Arg Leu Lys Glu Val
            100                 105                 110

Leu Gln Arg Pro Ala Ser Ile Met Glu Ser Asp Lys Gly Trp Thr Ser
        115                 120                 125

Ala Ser Thr Ser Gly Lys Pro Arg Lys Asp Lys Ala Ser Gly Lys Leu
130                 135                 140

Tyr Pro Glu Ser Glu Glu Asp Lys Glu Ala Pro Thr Gly Ser Arg Tyr
145                 150                 155                 160

Arg Gly Arg Pro Cys Leu Pro Glu Trp Asp His Ile Leu Cys Trp Pro
                165                 170                 175

Leu Gly Ala Pro Gly Glu Val Val Ala Val Pro Cys Pro Asp Tyr Lys
            180                 185                 190

Tyr Asp Phe Asn His Lys Gly His Ala Tyr Arg Arg Cys Asp Arg Asn
        195                 200                 205

Gly Ser Trp Glu Leu Val Pro Gly His Asn Arg Thr Trp Ala Asn Tyr
    210                 215                 220

Ser Glu Cys Val Lys Phe Leu Thr Asn Glu Thr Arg Glu Arg Glu Val
225                 230                 235                 240

Phe Asp Arg Leu Thr Gly His His His His His
                245                 250

<210> SEQ ID NO 24
<211> LENGTH: 247
<212> TYPE: PRT
<213> ORGANISM: artificial sequence
<220> FEATURE:
<223> OTHER INFORMATION: Fusion proteins

<400> SEQUENCE: 24

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
                20                  25                  30

Leu Met His Asn Leu Gly Lys His Leu Asn Ser Met Glu Arg Val Glu
            35                  40                  45

Trp Leu Arg Lys Lys Leu Gln Asp Val His Asn Phe Gly Gly Gly Gly
        50                  55                  60
```

Ser Gly Gly Gly Gly Ser Gly Gly Gly Ser Gly Gly Gly Ser
65                  70                  75                  80

Asp Asp Val Met Thr Lys Glu Glu Gln Ile Phe Leu Leu His Arg Ala
                85                  90                  95

Gln Ala Gln Cys Glu Lys Arg Leu Lys Glu Val Leu Gln Arg Pro Ala
            100                 105                 110

Ser Ile Met Glu Ser Asp Lys Gly Trp Thr Ser Ala Ser Thr Ser Gly
            115                 120                 125

Lys Pro Arg Lys Asp Lys Ala Ser Gly Lys Leu Tyr Pro Glu Ser Glu
        130                 135                 140

Glu Asp Lys Glu Ala Pro Thr Gly Ser Arg Tyr Arg Gly Arg Pro Cys
145                 150                 155                 160

Leu Pro Glu Trp Asp His Ile Leu Cys Trp Pro Leu Gly Ala Pro Gly
                165                 170                 175

Glu Val Val Ala Val Pro Cys Pro Asp Tyr Lys Tyr Asp Phe Asn His
            180                 185                 190

Lys Gly His Ala Tyr Arg Arg Cys Asp Arg Asn Gly Ser Trp Glu Leu
        195                 200                 205

Val Pro Gly His Asn Arg Thr Trp Ala Asn Tyr Ser Glu Cys Val Lys
210                 215                 220

Phe Leu Thr Asn Glu Thr Arg Glu Arg Glu Val Phe Asp Arg Leu Thr
225                 230                 235                 240

Gly His His His His His His
            245

<210> SEQ ID NO 25
<211> LENGTH: 504
<212> TYPE: PRT
<213> ORGANISM: artificial sequence
<220> FEATURE:
<223> OTHER INFORMATION: Fusion proteins

<400> SEQUENCE: 25

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ala
            20                  25                  30

Val Ala Glu Ile Gln Leu Met His Gln Arg Ala Lys Trp Ile Gln Asp
        35                  40                  45

Ala Arg Arg Arg Ala Phe Leu His Lys Leu Ile Ala Glu Ile His Thr
    50                  55                  60

Ala Glu Ile Gly Gly Gly Gly Ser Gly Gly Gly Gly Ser Gly Gly Gly
65                  70                  75                  80

Gly Ser Gly Gly Gly Gly Ser Asp Asp Val Met Thr Lys Glu Glu Gln
                85                  90                  95

Ile Phe Leu Leu His Arg Ala Gln Ala Gln Cys Glu Lys Arg Leu Lys
            100                 105                 110

Glu Val Leu Gln Arg Pro Ala Ser Ile Met Glu Ser Asp Lys Gly Trp
        115                 120                 125

Thr Ser Ala Ser Thr Ser Gly Lys Pro Arg Lys Asp Lys Ala Ser Gly
    130                 135                 140

Lys Leu Tyr Pro Glu Ser Glu Glu Asp Lys Glu Ala Pro Thr Gly Ser
145                 150                 155                 160

Arg Tyr Arg Gly Arg Pro Cys Leu Pro Glu Trp Asp His Ile Leu Cys
                165                 170                 175

```
Trp Pro Leu Gly Ala Pro Gly Glu Val Val Ala Val Pro Cys Pro Asp
            180                 185                 190

Tyr Ile Tyr Asp Phe Asn His Lys Gly His Ala Tyr Arg Arg Cys Asp
        195                 200                 205

Arg Asn Gly Ser Trp Glu Leu Val Pro Gly His Asn Arg Thr Trp Ala
    210                 215                 220

Asn Tyr Ser Glu Cys Val Lys Phe Leu Thr Asn Glu Thr Arg Glu Arg
225                 230                 235                 240

Glu Val Phe Asp Arg Leu Gly Gly Gly Ser Gly Gly Gly Gly Gly Ser
                245                 250                 255

Gly Gly Gly Gly Ser Gly Gly Gly Ser Phe Ser Gly Ser Glu Ala
            260                 265                 270

Thr Ala Ala Ile Leu Ser Arg Ala Pro Trp Ser Leu Gln Ser Val Asn
        275                 280                 285

Pro Gly Leu Lys Thr Asn Ser Ser Lys Glu Pro Lys Phe Thr Lys Cys
    290                 295                 300

Arg Ser Pro Glu Arg Glu Thr Phe Ser Cys His Trp Thr Asp Glu Val
305                 310                 315                 320

His His Gly Thr Lys Asn Leu Gly Pro Ile Gln Leu Phe Tyr Thr Arg
                325                 330                 335

Arg Asn Thr Gln Glu Trp Thr Gln Glu Trp Lys Glu Cys Pro Asp Tyr
            340                 345                 350

Val Ser Ala Gly Glu Asn Ser Cys Tyr Phe Asn Ser Ser Phe Thr Ser
        355                 360                 365

Ile Ala Ile Pro Tyr Cys Ile Lys Leu Thr Ser Asn Gly Gly Thr Val
370                 375                 380

Asp Glu Lys Cys Phe Ser Val Asp Glu Ile Val Gln Pro Asp Pro Pro
385                 390                 395                 400

Ile Ala Leu Asn Trp Thr Leu Leu Asn Val Ser Leu Thr Gly Ile His
                405                 410                 415

Ala Asp Ile Gln Val Arg Trp Glu Ala Pro Arg Asn Ala Asp Ile Gln
            420                 425                 430

Lys Gly Trp Met Val Leu Glu Tyr Glu Leu Gln Tyr Lys Glu Val Asn
        435                 440                 445

Glu Thr Lys Trp Lys Met Met Asp Pro Ile Leu Thr Thr Ser Val Pro
450                 455                 460

Val Tyr Ser Leu Lys Val Asp Lys Glu Tyr Glu Val Arg Val Arg Ser
465                 470                 475                 480

Lys Gln Arg Asn Ser Gly Asn Tyr Gly Glu Phe Ser Glu Val Leu Tyr
                485                 490                 495

Val Thr Leu Pro Gln Met Ser Gln
            500

<210> SEQ ID NO 26
<211> LENGTH: 499
<212> TYPE: PRT
<213> ORGANISM: artificial sequence
<220> FEATURE:
<223> OTHER INFORMATION: Fusion proteins

<400> SEQUENCE: 26

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ala Glu Ile Gln
            20                  25                  30
```

```
Leu Met His Gln Arg Ala Lys Trp Ile Gln Asp Ala Arg Arg Ala
        35                  40                  45

Phe Leu His Lys Leu Ile Ala Glu Ile His Thr Ala Glu Ile Gly Gly
    50                  55                  60

Gly Gly Ser Gly Gly Gly Ser Gly Gly Gly Ser Gly Gly Gly
65                  70                  75                  80

Gly Ser Asp Asp Val Met Thr Lys Glu Glu Gln Ile Phe Leu Leu His
                85                  90                  95

Arg Ala Gln Ala Gln Cys Glu Lys Arg Leu Lys Glu Val Leu Gln Arg
                100                 105                 110

Pro Ala Ser Ile Met Glu Ser Asp Lys Gly Trp Thr Ser Ala Ser Thr
            115                 120                 125

Ser Gly Lys Pro Arg Lys Asp Lys Ala Ser Gly Lys Leu Tyr Pro Glu
130                 135                 140

Ser Glu Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Ile Tyr Asp Phe
            180                 185                 190

Asn His Lys Gly His Ala Tyr Arg Arg Cys Asp Arg Asn Gly Ser Trp
    195                 200                 205

Glu Leu Val Pro Gly His Asn Arg Thr Trp Ala Asn Tyr Ser Glu Cys
    210                 215                 220

Val Lys Phe Leu Thr Asn Glu Thr Arg Glu Arg Glu Val Phe Asp Arg
225                 230                 235                 240

Leu Gly Gly Gly Gly Ser Gly Gly Gly Ser Gly Gly Gly Gly Ser
                245                 250                 255

Gly Gly Gly Gly Ser Phe Ser Gly Ser Glu Ala Thr Ala Ala Ile Leu
                260                 265                 270

Ser Arg Ala Pro Trp Ser Leu Gln Ser Val Asn Pro Gly Leu Lys Thr
    275                 280                 285

Asn Ser Ser Lys Glu Pro Lys Phe Thr Lys Cys Arg Ser Pro Glu Arg
    290                 295                 300

Glu Thr Phe Ser Cys His Trp Thr Asp Glu Val His Gly Thr Lys
305                 310                 315                 320

Asn Leu Gly Pro Ile Gln Leu Phe Tyr Thr Arg Arg Asn Thr Gln Glu
                325                 330                 335

Trp Thr Gln Glu Trp Lys Glu Cys Pro Asp Tyr Val Ser Ala Gly Glu
            340                 345                 350

Asn Ser Cys Tyr Phe Asn Ser Ser Phe Thr Ser Ile Ala Ile Pro Tyr
        355                 360                 365

Cys Ile Lys Leu Thr Ser Asn Gly Gly Thr Val Asp Glu Lys Cys Phe
    370                 375                 380

Ser Val Asp Glu Ile Val Gln Pro Asp Pro Ile Ala Leu Asn Trp
385                 390                 395                 400

Thr Leu Leu Asn Val Ser Leu Thr Gly Ile His Ala Asp Ile Gln Val
                405                 410                 415

Arg Trp Glu Ala Pro Arg Asn Ala Asp Ile Gln Lys Gly Trp Met Val
            420                 425                 430

Leu Glu Tyr Glu Leu Gln Tyr Lys Glu Val Asn Glu Thr Lys Trp Lys
        435                 440                 445

Met Met Asp Pro Ile Leu Thr Thr Ser Val Pro Val Tyr Ser Leu Lys
```

```
              450                 455                 460
Val Asp Lys Glu Tyr Glu Val Arg Val Arg Ser Lys Gln Arg Asn Ser
465                 470                 475                 480

Gly Asn Tyr Gly Glu Phe Ser Glu Val Leu Tyr Val Thr Leu Pro Gln
                    485                 490                 495

Met Ser Gln

<210> SEQ ID NO 27
<211> LENGTH: 325
<212> TYPE: PRT
<213> ORGANISM: artificial sequence
<220> FEATURE:
<223> OTHER INFORMATION: Fusion proteins

<400> SEQUENCE: 27

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ala
                20                  25                  30

Val Ala Glu Ile Gln Leu Met His Gln Arg Ala Lys Trp Ile Gln Asp
            35                  40                  45

Ala Arg Arg Arg Ala Phe Leu His Lys Leu Ile Ala Glu Ile His Thr
50                  55                  60

Ala Glu Ile Gly Gly Gly Gly Ser Gly Gly Gly Ser Gly Gly Gly Gly
65                  70                  75                  80

Gly Ser Gly Gly Gly Gly Ser Phe Ser Gly Ser Glu Ala Thr Ala Ala
                85                  90                  95

Ile Leu Ser Arg Ala Pro Trp Ser Leu Gln Ser Val Asn Pro Gly Leu
                100                 105                 110

Lys Thr Asn Ser Ser Lys Glu Pro Lys Phe Thr Lys Cys Arg Ser Pro
            115                 120                 125

Glu Arg Glu Thr Phe Ser Cys His Trp Thr Asp Glu Val His His Gly
130                 135                 140

Thr Lys Asn Leu Gly Pro Ile Gln Leu Phe Tyr Thr Arg Arg Asn Thr
145                 150                 155                 160

Gln Glu Trp Thr Gln Glu Trp Lys Glu Cys Pro Asp Tyr Val Ser Ala
                165                 170                 175

Gly Glu Asn Ser Cys Tyr Phe Asn Ser Ser Phe Thr Ser Ile Ala Ile
                180                 185                 190

Pro Tyr Cys Ile Lys Leu Thr Ser Asn Gly Gly Thr Val Asp Glu Lys
            195                 200                 205

Cys Phe Ser Val Asp Glu Ile Val Gln Pro Asp Pro Pro Ile Ala Leu
210                 215                 220

Asn Trp Thr Leu Leu Asn Val Ser Leu Thr Gly Ile His Ala Asp Ile
225                 230                 235                 240

Gln Val Arg Trp Glu Ala Pro Arg Asn Ala Asp Ile Gln Lys Gly Trp
                245                 250                 255

Met Val Leu Glu Tyr Glu Leu Gln Tyr Lys Glu Val Asn Glu Thr Lys
                260                 265                 270

Trp Lys Met Met Asp Pro Ile Leu Thr Thr Ser Val Pro Val Tyr Ser
            275                 280                 285

Leu Lys Val Asp Lys Glu Tyr Glu Val Arg Val Arg Ser Lys Gln Arg
        290                 295                 300

Asn Ser Gly Asn Tyr Gly Glu Phe Ser Glu Val Leu Tyr Val Thr Leu
305                 310                 315                 320
```

-continued

Pro Gln Met Ser Gln
            325

<210> SEQ ID NO 28
<211> LENGTH: 320
<212> TYPE: PRT
<213> ORGANISM: artificial sequence
<220> FEATURE:
<223> OTHER INFORMATION: Fusion proteins

<400> SEQUENCE: 28

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ala Glu Ile Gln
            20                  25                  30

Leu Met His Gln Arg Ala Lys Trp Ile Gln Asp Ala Arg Arg Arg Ala
        35                  40                  45

Phe Leu His Lys Leu Ile Ala Glu Ile His Thr Ala Glu Ile Gly Gly
    50                  55                  60

Gly Gly Ser Gly Gly Gly Ser Gly Gly Gly Ser Gly Gly Gly
65                  70                  75                  80

Gly Ser Phe Ser Gly Ser Glu Ala Thr Ala Ala Ile Leu Ser Arg Ala
                85                  90                  95

Pro Trp Ser Leu Gln Ser Val Asn Pro Gly Leu Lys Thr Asn Ser Ser
            100                 105                 110

Lys Glu Pro Lys Phe Thr Lys Cys Arg Ser Pro Glu Arg Glu Thr Phe
        115                 120                 125

Ser Cys His Trp Thr Asp Glu Val His His Gly Thr Lys Asn Leu Gly
    130                 135                 140

Pro Ile Gln Leu Phe Tyr Thr Arg Arg Asn Thr Gln Glu Trp Thr Gln
145                 150                 155                 160

Glu Trp Lys Glu Cys Pro Asp Tyr Val Ser Ala Gly Glu Asn Ser Cys
                165                 170                 175

Tyr Phe Asn Ser Ser Phe Thr Ser Ile Ala Ile Pro Tyr Cys Ile Lys
            180                 185                 190

Leu Thr Ser Asn Gly Gly Thr Val Asp Glu Lys Cys Phe Ser Val Asp
        195                 200                 205

Glu Ile Val Gln Pro Asp Pro Pro Ile Ala Leu Asn Trp Thr Leu Leu
    210                 215                 220

Asn Val Ser Leu Thr Gly Ile His Ala Asp Ile Gln Val Arg Trp Glu
225                 230                 235                 240

Ala Pro Arg Asn Ala Asp Ile Gln Lys Gly Trp Met Val Leu Glu Tyr
                245                 250                 255

Glu Leu Gln Tyr Lys Glu Val Asn Glu Thr Lys Trp Lys Met Met Asp
            260                 265                 270

Pro Ile Leu Thr Thr Ser Val Pro Val Tyr Ser Leu Lys Val Asp Lys
        275                 280                 285

Glu Tyr Glu Val Arg Val Arg Ser Lys Gln Arg Asn Ser Gly Asn Tyr
    290                 295                 300

Gly Glu Phe Ser Glu Val Leu Tyr Val Thr Leu Pro Gln Met Ser Gln
305                 310                 315                 320

<210> SEQ ID NO 29
<211> LENGTH: 254
<212> TYPE: PRT
<213> ORGANISM: artificial sequence

```
<220> FEATURE:
<223> OTHER INFORMATION: Fusion proteins

<400> SEQUENCE: 29

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ala
            20                  25                  30

Val Ala Glu Ile Gln Leu Met His Gln Arg Ala Lys Trp Ile Gln Asp
        35                  40                  45

Ala Arg Arg Arg Ala Phe Leu His Lys Leu Ile Ala Glu Ile His Thr
    50                  55                  60

Ala Glu Ile Gly Gly Gly Gly Ser Gly Gly Gly Ser Gly Gly Gly
65                  70                  75                  80

Gly Ser Gly Gly Gly Ser Asp Asp Val Met Thr Lys Glu Glu Gln
                85                  90                  95

Ile Phe Leu Leu His Arg Ala Gln Ala Gln Cys Glu Lys Arg Leu Lys
            100                 105                 110

Glu Val Leu Gln Arg Pro Ala Ser Ile Met Glu Ser Asp Lys Gly Trp
        115                 120                 125

Thr Ser Ala Ser Thr Ser Gly Lys Pro Arg Lys Asp Lys Ala Ser Gly
    130                 135                 140

Lys Leu Tyr Pro Glu Ser Glu Asp Lys Glu Ala Pro Thr Gly Ser
145                 150                 155                 160

Arg Tyr Arg Gly Arg Pro Cys Leu Pro Glu Trp Asp His Ile Leu Cys
                165                 170                 175

Trp Pro Leu Gly Ala Pro Gly Glu Val Val Ala Val Pro Cys Pro Asp
            180                 185                 190

Tyr Ile Tyr Asp Phe Asn His Lys Gly His Ala Tyr Arg Arg Cys Asp
        195                 200                 205

Arg Asn Gly Ser Trp Glu Leu Val Pro Gly His Asn Arg Thr Trp Ala
    210                 215                 220

Asn Tyr Ser Glu Cys Val Lys Phe Leu Thr Asn Glu Thr Arg Glu Arg
225                 230                 235                 240

Glu Val Phe Asp Arg Leu Thr Gly His His His His His
                245                 250

<210> SEQ ID NO 30
<211> LENGTH: 249
<212> TYPE: PRT
<213> ORGANISM: artificial sequence
<220> FEATURE:
<223> OTHER INFORMATION: Fusion proteins

<400> SEQUENCE: 30

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ala Glu Ile Gln
            20                  25                  30

Leu Met His Gln Arg Ala Lys Trp Ile Gln Asp Ala Arg Arg Arg Ala
        35                  40                  45

Phe Leu His Lys Leu Ile Ala Glu Ile His Thr Ala Glu Ile Gly Gly
    50                  55                  60

Gly Gly Ser Gly Gly Gly Ser Gly Gly Gly Gly Ser Gly Gly Gly
65                  70                  75                  80

Gly Ser Asp Asp Val Met Thr Lys Glu Glu Gln Ile Phe Leu Leu His
```

```
            85                  90                  95
Arg Ala Gln Ala Gln Cys Glu Lys Arg Leu Lys Glu Val Leu Gln Arg
            100                 105                 110

Pro Ala Ser Ile Met Glu Ser Asp Lys Gly Trp Thr Ser Ala Ser Thr
            115                 120                 125

Ser Gly Lys Pro Arg Lys Asp Lys Ala Ser Gly Lys Leu Tyr Pro Glu
            130                 135                 140

Ser Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
            165                 170                 175

Pro Gly Glu Val Val Ala Val Pro Cys Pro Asp Tyr Ile Tyr Asp Phe
            180                 185                 190

Asn His Lys Gly His Ala Tyr Arg Arg Cys Asp Arg Asn Gly Ser Trp
            195                 200                 205

Glu Leu Val Pro Gly His Asn Arg Thr Trp Ala Asn Tyr Ser Glu Cys
            210                 215                 220

Val Lys Phe Leu Thr Asn Glu Thr Arg Glu Arg Glu Val Phe Asp Arg
225                 230                 235                 240

Leu Thr Gly His His His His His His
            245

<210> SEQ ID NO 31
<211> LENGTH: 552
<212> TYPE: PRT
<213> ORGANISM: artificial sequence
<220> FEATURE:
<223> OTHER INFORMATION: Fusion proteins

<400> SEQUENCE: 31

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
            85                  90                  95

Ser Leu Gly Glu Ala Asp Lys Ala Asp Val Asn Val Leu Thr Lys Ala
            100                 105                 110

Lys Ser Gln Gly Gly Gly Gly Ser Gly Gly Gly Gly Ser Gly Gly Gly
            115                 120                 125

Gly Ser Gly Gly Gly Gly Ser Asp Asp Val Met Thr Lys Glu Glu Gln
            130                 135                 140

Ile Phe Leu Leu His Arg Ala Gln Ala Gln Cys Glu Lys Arg Leu Lys
145                 150                 155                 160

Glu Val Leu Gln Arg Pro Ala Ser Ile Met Glu Ser Asp Lys Gly Trp
            165                 170                 175

Thr Ser Ala Ser Thr Ser Gly Lys Pro Arg Lys Asp Lys Ala Ser Gly
            180                 185                 190

Lys Leu Tyr Pro Glu Ser Glu Glu Asp Lys Glu Ala Pro Thr Gly Ser
```

```
                195                 200                 205
Arg Tyr Arg Gly Arg Pro Cys Leu Pro Glu Trp Asp His Ile Leu Cys
210                 215                 220

Trp Pro Leu Gly Ala Pro Gly Glu Val Val Ala Val Pro Cys Pro Asp
225                 230                 235                 240

Tyr Ile Tyr Asp Phe Asn His Lys Gly His Ala Tyr Arg Arg Cys Asp
                245                 250                 255

Arg Asn Gly Ser Trp Glu Leu Val Pro Gly His Asn Arg Thr Trp Ala
            260                 265                 270

Asn Tyr Ser Glu Cys Val Lys Phe Leu Thr Asn Glu Thr Arg Glu Arg
        275                 280                 285

Glu Val Phe Asp Arg Leu Gly Gly Gly Ser Gly Gly Gly Gly Ser
    290                 295                 300

Gly Gly Gly Ser Gly Gly Gly Ser Phe Ser Gly Ser Glu Ala
305                 310                 315                 320

Thr Ala Ala Ile Leu Ser Arg Ala Pro Trp Ser Leu Gln Ser Val Asn
                325                 330                 335

Pro Gly Leu Lys Thr Asn Ser Ser Lys Glu Pro Lys Phe Thr Lys Cys
            340                 345                 350

Arg Ser Pro Glu Arg Glu Thr Phe Ser Cys His Trp Thr Asp Glu Val
        355                 360                 365

His His Gly Thr Lys Asn Leu Gly Pro Ile Gln Leu Phe Tyr Thr Arg
    370                 375                 380

Arg Asn Thr Gln Glu Trp Thr Gln Glu Trp Lys Glu Cys Pro Asp Tyr
385                 390                 395                 400

Val Ser Ala Gly Glu Asn Ser Cys Tyr Phe Asn Ser Ser Phe Thr Ser
                405                 410                 415

Ile Ala Ile Pro Tyr Cys Ile Lys Leu Thr Ser Asn Gly Gly Thr Val
            420                 425                 430

Asp Glu Lys Cys Phe Ser Val Asp Glu Ile Val Gln Pro Asp Pro Pro
        435                 440                 445

Ile Ala Leu Asn Trp Thr Leu Leu Asn Val Ser Leu Thr Gly Ile His
450                 455                 460

Ala Asp Ile Gln Val Arg Trp Glu Ala Pro Arg Asn Ala Asp Ile Gln
465                 470                 475                 480

Lys Gly Trp Met Val Leu Glu Tyr Glu Leu Gln Tyr Lys Glu Val Asn
                485                 490                 495

Glu Thr Lys Trp Lys Met Met Asp Pro Ile Leu Thr Thr Ser Val Pro
            500                 505                 510

Val Tyr Ser Leu Lys Val Asp Lys Glu Tyr Glu Val Arg Val Arg Ser
        515                 520                 525

Lys Gln Arg Asn Ser Gly Asn Tyr Gly Glu Phe Ser Glu Val Leu Tyr
    530                 535                 540

Val Thr Leu Pro Gln Met Ser Gln
545                 550

<210> SEQ ID NO 32
<211> LENGTH: 547
<212> TYPE: PRT
<213> ORGANISM: artificial sequence
<220> FEATURE:
<223> OTHER INFORMATION: Fusion proteins

<400> SEQUENCE: 32

Met Ala Thr Gly Ser Arg Thr Ser Leu Leu Leu Ala Phe Gly Leu Leu
```

-continued

```
1               5                   10                  15
Cys Leu Pro Trp Leu Gln Glu Gly Ser Ala Ser Val Ser Glu Ile Gln
            20                  25                  30
Leu Met His Asn Leu Gly Lys His Leu Asn Ser Met Glu Arg Val Glu
            35                  40                  45
Trp Leu Arg Lys Lys Leu Gln Asp Val His Asn Phe Val Ala Leu Gly
 50                  55                  60
Ala Pro Leu Ala Pro Arg Asp Ala Gly Ser Gln Arg Pro Arg Lys Lys
 65                  70                  75                  80
Glu Asp Asn Val Leu Val Glu Ser His Glu Lys Ser Leu Gly Glu Ala
                85                  90                  95
Asp Lys Ala Asp Val Asn Val Leu Thr Lys Ala Lys Ser Gln Gly Gly
            100                 105                 110
Gly Gly Ser Gly Gly Gly Ser Gly Gly Gly Ser Gly Gly Gly
            115                 120                 125
Gly Ser Asp Asp Val Met Thr Lys Glu Glu Gln Ile Phe Leu Leu His
130                 135                 140
Arg Ala Gln Ala Gln Cys Glu Lys Arg Leu Lys Glu Val Leu Gln Arg
145                 150                 155                 160
Pro Ala Ser Ile Met Glu Ser Asp Lys Gly Trp Thr Ser Ala Ser Thr
                165                 170                 175
Ser Gly Lys Pro Arg Lys Asp Lys Ala Ser Gly Lys Leu Tyr Pro Glu
            180                 185                 190
Ser Glu Glu Asp Lys Glu Ala Pro Thr Gly Ser Arg Tyr Arg Gly Arg
            195                 200                 205
Pro Cys Leu Pro Glu Trp Asp His Ile Leu Cys Trp Pro Leu Gly Ala
210                 215                 220
Pro Gly Glu Val Val Ala Val Pro Cys Pro Asp Tyr Ile Tyr Asp Phe
225                 230                 235                 240
Asn His Lys Gly His Ala Tyr Arg Arg Cys Asp Arg Asn Gly Ser Trp
                245                 250                 255
Glu Leu Val Pro Gly His Asn Arg Thr Trp Ala Asn Tyr Ser Glu Cys
            260                 265                 270
Val Lys Phe Leu Thr Asn Glu Thr Arg Glu Arg Glu Val Phe Asp Arg
            275                 280                 285
Leu Gly Gly Gly Ser Gly Gly Gly Ser Gly Gly Gly Ser
290                 295                 300
Gly Gly Gly Ser Phe Ser Gly Ser Glu Ala Thr Ala Ala Ile Leu
305                 310                 315                 320
Ser Arg Ala Pro Trp Ser Leu Gln Ser Val Asn Pro Gly Leu Lys Thr
                325                 330                 335
Asn Ser Ser Lys Glu Pro Lys Phe Thr Lys Cys Arg Ser Pro Glu Arg
            340                 345                 350
Glu Thr Phe Ser Cys His Trp Thr Asp Glu Val His His Gly Thr Lys
            355                 360                 365
Asn Leu Gly Pro Ile Gln Leu Phe Tyr Thr Arg Arg Asn Thr Gln Glu
370                 375                 380
Trp Thr Gln Glu Trp Lys Glu Cys Pro Asp Tyr Val Ser Ala Gly Glu
385                 390                 395                 400
Asn Ser Cys Tyr Phe Asn Ser Ser Phe Thr Ser Ile Ala Ile Pro Tyr
                405                 410                 415
Cys Ile Lys Leu Thr Ser Asn Gly Gly Thr Val Asp Glu Lys Cys Phe
            420                 425                 430
```

Ser Val Asp Glu Ile Val Gln Pro Asp Pro Ile Ala Leu Asn Trp
        435                 440                 445

Thr Leu Leu Asn Val Ser Leu Thr Gly Ile His Ala Asp Ile Gln Val
        450                 455                 460

Arg Trp Glu Ala Pro Arg Asn Ala Asp Ile Gln Lys Gly Trp Met Val
465                 470                 475                 480

Leu Glu Tyr Glu Leu Gln Tyr Lys Val Asn Glu Thr Lys Trp Lys
                485                 490                 495

Met Met Asp Pro Ile Leu Thr Thr Ser Val Pro Val Tyr Ser Leu Lys
                500                 505                 510

Val Asp Lys Glu Tyr Glu Val Arg Val Arg Ser Lys Gln Arg Asn Ser
                515                 520                 525

Gly Asn Tyr Gly Glu Phe Ser Glu Val Leu Tyr Val Thr Leu Pro Gln
                530                 535                 540

Met Ser Gln
545

<210> SEQ ID NO 33
<211> LENGTH: 373
<212> TYPE: PRT
<213> ORGANISM: artificial sequence
<220> FEATURE:
<223> OTHER INFORMATION: Fusion proteins

<400> SEQUENCE: 33

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln Gly Gly Gly Gly Ser Gly Gly Gly Gly Ser Gly Gly Gly
        115                 120                 125

Gly Ser Gly Gly Gly Gly Ser Phe Ser Gly Ser Glu Ala Thr Ala Ala
    130                 135                 140

Ile Leu Ser Arg Ala Pro Trp Ser Leu Gln Ser Val Asn Pro Gly Leu
145                 150                 155                 160

Lys Thr Asn Ser Ser Lys Glu Pro Lys Phe Thr Lys Cys Arg Ser Pro
                165                 170                 175

Glu Arg Glu Thr Phe Ser Cys His Trp Thr Asp Glu Val His His Gly
            180                 185                 190

Thr Lys Asn Leu Gly Pro Ile Gln Leu Phe Tyr Thr Arg Arg Asn Thr
        195                 200                 205

Gln Glu Trp Thr Gln Glu Trp Lys Glu Cys Pro Asp Tyr Val Ser Ala
    210                 215                 220

Gly Glu Asn Ser Cys Tyr Phe Asn Ser Ser Phe Thr Ser Ile Ala Ile
225                 230                 235                 240

```
Pro Tyr Cys Ile Lys Leu Thr Ser Asn Gly Gly Thr Val Asp Glu Lys
                245                 250                 255

Cys Phe Ser Val Asp Glu Ile Val Gln Pro Asp Pro Ile Ala Leu
            260                 265                 270

Asn Trp Thr Leu Leu Asn Val Ser Leu Thr Gly Ile His Ala Asp Ile
            275                 280                 285

Gln Val Arg Trp Glu Ala Pro Arg Asn Ala Asp Ile Gln Lys Gly Trp
        290                 295                 300

Met Val Leu Glu Tyr Glu Leu Gln Tyr Lys Glu Val Asn Glu Thr Lys
305                 310                 315                 320

Trp Lys Met Met Asp Pro Ile Leu Thr Thr Ser Val Pro Val Tyr Ser
                325                 330                 335

Leu Lys Val Asp Lys Glu Tyr Glu Val Arg Val Arg Ser Lys Gln Arg
            340                 345                 350

Asn Ser Gly Asn Tyr Gly Glu Phe Ser Glu Val Leu Tyr Val Thr Leu
        355                 360                 365

Pro Gln Met Ser Gln
    370

<210> SEQ ID NO 34
<211> LENGTH: 368
<212> TYPE: PRT
<213> ORGANISM: artificial sequence
<220> FEATURE:
<223> OTHER INFORMATION: Fusion proteins

<400> SEQUENCE: 34

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
            20                  25                  30

Leu Met His Asn Leu Gly Lys His Leu Asn Ser Met Glu Arg Val Glu
        35                  40                  45

Trp Leu Arg Lys Lys Leu Gln Asp Val His Asn Phe Val Ala Leu Gly
    50                  55                  60

Ala Pro Leu Ala Pro Arg Asp Ala Gly Ser Gln Arg Pro Arg Lys Lys
65                  70                  75                  80

Glu Asp Asn Val Leu Val Glu Ser His Glu Lys Ser Leu Gly Glu Ala
                85                  90                  95

Asp Lys Ala Asp Val Asn Val Leu Thr Lys Ala Lys Ser Gln Gly Gly
            100                 105                 110

Gly Gly Ser Gly Gly Gly Gly Ser Gly Gly Gly Gly Ser Gly Gly Gly
        115                 120                 125

Gly Ser Phe Ser Gly Ser Glu Ala Thr Ala Ala Ile Leu Ser Arg Ala
    130                 135                 140

Pro Trp Ser Leu Gln Ser Val Asn Pro Gly Leu Lys Thr Asn Ser Ser
145                 150                 155                 160

Lys Glu Pro Lys Phe Thr Lys Cys Arg Ser Pro Glu Arg Glu Thr Phe
                165                 170                 175

Ser Cys His Trp Thr Asp Glu Val His His Gly Thr Lys Asn Leu Gly
            180                 185                 190

Pro Ile Gln Leu Phe Tyr Thr Arg Arg Asn Thr Gln Glu Trp Thr Gln
        195                 200                 205

Glu Trp Lys Glu Cys Pro Asp Tyr Val Ser Ala Gly Glu Asn Ser Cys
    210                 215                 220
```

```
Tyr Phe Asn Ser Ser Phe Thr Ser Ile Ala Ile Pro Tyr Cys Ile Lys
225                 230                 235                 240

Leu Thr Ser Asn Gly Gly Thr Val Asp Glu Lys Cys Phe Ser Val Asp
            245                 250                 255

Glu Ile Val Gln Pro Asp Pro Pro Ile Ala Leu Asn Trp Thr Leu Leu
        260                 265                 270

Asn Val Ser Leu Thr Gly Ile His Ala Asp Ile Gln Val Arg Trp Glu
        275                 280                 285

Ala Pro Arg Asn Ala Asp Ile Gln Lys Gly Trp Met Val Leu Glu Tyr
    290                 295                 300

Glu Leu Gln Tyr Lys Glu Val Asn Glu Thr Lys Trp Lys Met Met Asp
305                 310                 315                 320

Pro Ile Leu Thr Thr Ser Val Pro Val Tyr Ser Leu Lys Val Asp Lys
            325                 330                 335

Glu Tyr Glu Val Arg Val Arg Ser Lys Gln Arg Asn Ser Gly Asn Tyr
        340                 345                 350

Gly Glu Phe Ser Glu Val Leu Tyr Val Thr Leu Pro Gln Met Ser Gln
            355                 360                 365

<210> SEQ ID NO 35
<211> LENGTH: 302
<212> TYPE: PRT
<213> ORGANISM: artificial sequence
<220> FEATURE:
<223> OTHER INFORMATION: Fusion proteins

<400> SEQUENCE: 35

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
    50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln Gly Gly Gly Gly Ser Gly Gly Gly Ser Gly Gly Gly
            115                 120                 125

Gly Ser Gly Gly Gly Ser Asp Asp Val Met Thr Lys Glu Glu Gln
    130                 135                 140

Ile Phe Leu Leu His Arg Ala Gln Ala Gln Cys Glu Lys Arg Leu Lys
145                 150                 155                 160

Glu Val Leu Gln Arg Pro Ala Ser Ile Met Glu Ser Asp Lys Gly Trp
                165                 170                 175

Thr Ser Ala Ser Thr Ser Gly Lys Pro Arg Lys Asp Lys Ala Ser Gly
            180                 185                 190

Lys Leu Tyr Pro Glu Ser Glu Glu Asp Lys Glu Ala Pro Thr Gly Ser
        195                 200                 205

Arg Tyr Arg Gly Arg Pro Cys Leu Pro Glu Trp Asp His Ile Leu Cys
210                 215                 220
```

Trp Pro Leu Gly Ala Pro Gly Glu Val Val Ala Val Pro Cys Pro Asp
225                 230                 235                 240

Tyr Ile Tyr Asp Phe Asn His Lys Gly His Ala Tyr Arg Arg Cys Asp
            245                 250                 255

Arg Asn Gly Ser Trp Glu Leu Val Pro Gly His Asn Arg Thr Trp Ala
        260                 265                 270

Asn Tyr Ser Glu Cys Val Lys Phe Leu Thr Asn Glu Thr Arg Glu Arg
    275                 280                 285

Glu Val Phe Asp Arg Leu Thr Gly His His His His His His
290                 295                 300

<210> SEQ ID NO 36
<211> LENGTH: 297
<212> TYPE: PRT
<213> ORGANISM: artificial sequence
<220> FEATURE:
<223> OTHER INFORMATION: Fusion proteins

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Val Ser Glu Ile Gln
            20                  25                  30

Leu Met His Asn Leu Gly Lys His Leu Asn Ser Met Glu Arg Val Glu
        35                  40                  45

Trp Leu Arg Lys Lys Leu Gln Asp Val His Asn Phe Val Ala Leu Gly
    50                  55                  60

Ala Pro Leu Ala Pro Arg Asp Ala Gly Ser Gln Arg Pro Arg Lys Lys
65                  70                  75                  80

Glu Asp Asn Val Leu Val Glu Ser His Glu Lys Ser Leu Gly Glu Ala
                85                  90                  95

Asp Lys Ala Asp Val Asn Val Leu Thr Lys Ala Lys Ser Gln Gly Gly
            100                 105                 110

Gly Gly Ser Gly Gly Gly Gly Ser Gly Gly Gly Gly Ser Gly Gly Gly
        115                 120                 125

Gly Ser Asp Asp Val Met Thr Lys Glu Glu Gln Ile Phe Leu Leu His
130                 135                 140

Arg Ala Gln Ala Gln Cys Glu Lys Arg Leu Lys Glu Val Leu Gln Arg
145                 150                 155                 160

Pro Ala Ser Ile Met Glu Ser Asp Lys Gly Trp Thr Ser Ala Ser Thr
                165                 170                 175

Ser Gly Lys Pro Arg Lys Asp Lys Ala Ser Gly Lys Leu Tyr Pro Glu
            180                 185                 190

Ser Glu Glu Asp Lys Glu Ala Pro Thr Gly Ser Arg Tyr Arg Gly Arg
        195                 200                 205

Pro Cys Leu Pro Glu Trp Asp His Ile Leu Cys Trp Pro Leu Gly Ala
210                 215                 220

Pro Gly Glu Val Val Ala Val Pro Cys Pro Asp Tyr Ile Tyr Asp Phe
225                 230                 235                 240

Asn His Lys Gly His Ala Tyr Arg Arg Cys Asp Arg Asn Gly Ser Trp
                245                 250                 255

Glu Leu Val Pro Gly His Asn Arg Thr Trp Ala Asn Tyr Ser Glu Cys
            260                 265                 270

Val Lys Phe Leu Thr Asn Glu Thr Arg Glu Arg Glu Val Phe Asp Arg
        275                 280                 285

```
Leu Thr Gly His His His His His
    290             295
```

<210> SEQ ID NO 37
<211> LENGTH: 36
<212> TYPE: PRT
<213> ORGANISM: artificial sequence
<220> FEATURE:
<223> OTHER INFORMATION: Fusion proteins

<400> SEQUENCE: 37

```
Ala Val Ala Glu Ile Gln Leu Met His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35
```

<210> SEQ ID NO 38
<211> LENGTH: 756
<212> TYPE: DNA
<213> ORGANISM: artificial sequence
<220> FEATURE:
<223> OTHER INFORMATION: Fusion proteins

<400> SEQUENCE: 38

| | | |
|---|---|---|
| atgatacctg caaaagacat ggctaaagtt atgattgtca tgttggcaat ttgttttctt | 60 |
| acaaaatcgg atgggaaatc tgttaagaag agatctgtga gtgaaataca gcttatgcat | 120 |
| aacctgggaa acatctgaa ctcgatggag agagtagaat ggctgcgtaa gaagctgcag | 180 |
| gatgtgcaca attttggtgg cggaggtagt ggtggcggag gtagcggtgg cggaggttct | 240 |
| ggtggcggag gttccgatga cgtcatgact aaagaggaac agatcttcct gctgcaccgt | 300 |
| gctcaggccc agtgcgaaaa acggctcaag gaggtcctgc agaggccagc cagcataatg | 360 |
| gaatcagaca agggatggac atctgcgtcc acatcaggga agcccaggaa agataaggca | 420 |
| tctgggaagc tctaccctga gtctgaggag acaaggagg cacccactgg cagcaggtac | 480 |
| cgagggcgcc cctgtctgcc ggaatgggac acatcctgt gctggccgct gggggcacca | 540 |
| ggtgaggtgg tggctgtgcc ctgtccggac tacaagtatg acttcaatca caaaggccat | 600 |
| gcctaccgac gctgtgaccg caatggcagc tgggagctgg tgcctgggca acaggacg | 660 |
| tgggccaact acagcgagtg tgtcaaattt ctcaccaatg agactcgtga cgggaggtg | 720 |
| tttgaccgcc tgaccggtca tcatcaccat caccat | 756 |

<210> SEQ ID NO 39
<211> LENGTH: 1491
<212> TYPE: DNA
<213> ORGANISM: artificial sequence
<220> FEATURE:
<223> OTHER INFORMATION: Fusion proteins

<400> SEQUENCE: 39

| | | |
|---|---|---|
| atggctacag ctcccggac gtccctgctc ctggcttttg gcctgctctg cctgccctgg | 60 |
| cttcaagagg gcagtgcctc tgtgagtgaa atacagctta tgcataacct gggaaaacat | 120 |
| ctgaactcga tggagagagt agaatggctg cgtaagaagc tgcaggatgt gcacaatttt | 180 |
| ggtggcggag gtagtggtgg cggaggtagc ggtggcggag gttctggtgg cggaggttcc | 240 |
| gatgacgtca tgactaaaga ggaacagatc ttcctgctgc accgtgctca ggcccagtgc | 300 |

```
gaaaaacggc tcaaggaggt cctgcagagg ccagccagca taatggaatc agacaaggga    360
tggacatctg cgtccacatc agggaagccc aggaaagata aggcatctgg gaagctctac    420
cctgagtctg aggaggacaa ggaggcaccc actggcagca ggtaccgagg cgcccctgt     480 ctgccggaat gggaccacat cctgtgctgg ccgctggggg caccaggtga ggtggtggct    540
gtgccctgtc cggactacaa gtatgacttc aatcacaaag gccatgccta ccgacgctgt    600
gaccgcaatg gcagctggga gctggtgcct gggcacaaca ggacgtgggc caactacagc    660
gagtgtgtca aatttctcac caatgagact cgtgaacggg aggtgtttga ccgcctgggt    720
ggcggaggta gtggtggcgg aggtagcggt ggcggaggtt ctggtggcgg aggttccttt    780
tctggaagtg aggccacagc agctatcctt agcagagcac cctggagtct gcaaagtgtt    840
aatccaggcc taaagacaaa ttcttctaag gagcctaaat tcaccaagtg ccgttcacct    900
gagcgagaga cttttcatg ccactggaca atgaggttc atcatggtac aaagaaccta     960
ggacccatac agctgttcta taccagaagg aacactcaag aatggactca agaatggaaa   1020
gaatgccctg attatgtttc tgctggggaa acagctgtt actttaattc atcgtttacc    1080
tccatcgcaa taccttattg tatcaagcta actagcaatg gtggtacagt ggatgaaaag   1140
tgtttctctg ttgatgaaat agtgcaacca gatccaccca ttgccctcaa ctggactta    1200 ctgaacgtca gtttaactgg gattcatgca gatatccaag tgagatggga agcaccacgc   1260
aatgcagata ttcagaaagg atggatggtt ctggagtatg aacttcaata caaagaagta   1320
aatgaaacta atggaaaat gatggaccct atattgacaa catcagttcc agtgtactca    1380
ttgaaagtgg ataaggaata tgaagtgcgt gtgagatcca acaacgaaa ctctggaaat    1440 tatggcgagt tcagtgaggt gctctatgta acacttcctc agatgagcca a            1491

<210> SEQ ID NO 40
<211> LENGTH: 36
<212> TYPE: PRT
<213> ORGANISM: artificial sequence
<220> FEATURE:
<223> OTHER INFORMATION: PTHrP

<400> SEQUENCE: 40

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 41
<211> LENGTH: 24
<212> TYPE: PRT
<213> ORGANISM: artificial sequence
<220> FEATURE:
<223> OTHER INFORMATION: PTHrP signal sequence

<400> SEQUENCE: 41

Met Gln Arg Arg Leu Val Gln Gln Trp Ser Val Ala Val Phe Leu Leu
1               5                   10                  15

Ser Tyr Ala Val Pro Ser Cys Gly
            20

<210> SEQ ID NO 42
<211> LENGTH: 507
<212> TYPE: PRT
```

<213> ORGANISM: artificial sequence
<220> FEATURE:
<223> OTHER INFORMATION: Fusion proteins

<400> SEQUENCE: 42

```
Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Ala Val Ser Glu His Gln Leu Leu His Asp Lys Gly Lys Ser
        35                  40                  45

Ile Gln Asp Leu Arg Arg Arg Phe Phe Leu His His Leu Ile Ala Glu
    50                  55                  60

Ile His Thr Ala Glu Ile Gly Gly Gly Gly Ser Gly Gly Gly Gly Ser
65                  70                  75                  80

Gly Gly Gly Gly Ser Gly Gly Gly Ser Asp Asp Val Met Thr Lys
                85                  90                  95

Glu Glu Gln Ile Phe Leu Leu His Arg Ala Gln Ala Gln Cys Glu Lys
                100                 105                 110

Arg Leu Lys Glu Val Leu Gln Arg Pro Ala Ser Ile Met Glu Ser Asp
            115                 120                 125

Lys Gly Trp Thr Ser Ala Ser Thr Ser Gly Lys Pro Arg Lys Asp Lys
        130                 135                 140

Ala Ser Gly Lys Leu Tyr Pro Glu Ser Glu Glu Asp Lys Glu Ala Pro
145                 150                 155                 160

Thr Gly Ser Arg Tyr Arg Gly Arg Pro Cys Leu Pro Glu Trp Asp His
                165                 170                 175

Ile Leu Cys Trp Pro Leu Gly Ala Pro Gly Glu Val Val Ala Val Pro
            180                 185                 190

Cys Pro Asp Tyr Ile Tyr Asp Phe Asn His Lys Gly His Ala Tyr Arg
        195                 200                 205

Arg Cys Asp Arg Asn Gly Ser Trp Glu Leu Val Pro Gly His Asn Arg
    210                 215                 220

Thr Trp Ala Asn Tyr Ser Glu Cys Val Lys Phe Leu Thr Asn Glu Thr
225                 230                 235                 240

Arg Glu Arg Glu Val Phe Asp Arg Leu Gly Gly Gly Ser Gly Gly
                245                 250                 255

Gly Gly Ser Gly Gly Gly Gly Ser Gly Gly Gly Gly Ser Phe Ser Gly
            260                 265                 270

Ser Glu Ala Thr Ala Ala Ile Leu Ser Arg Ala Pro Trp Ser Leu Gln
        275                 280                 285

Ser Val Asn Pro Gly Leu Lys Thr Asn Ser Ser Lys Glu Pro Lys Phe
    290                 295                 300

Thr Lys Cys Arg Ser Pro Glu Arg Glu Thr Phe Ser Cys His Trp Thr
305                 310                 315                 320

Asp Glu Val His His Gly Thr Lys Asn Leu Gly Pro Ile Gln Leu Phe
                325                 330                 335

Tyr Thr Arg Arg Asn Thr Gln Glu Trp Thr Gln Glu Trp Lys Glu Cys
            340                 345                 350

Pro Asp Tyr Val Ser Ala Gly Glu Asn Ser Cys Tyr Phe Asn Ser Ser
        355                 360                 365

Phe Thr Ser Ile Ala Ile Pro Tyr Cys Ile Lys Leu Thr Ser Asn Gly
    370                 375                 380

Gly Thr Val Asp Glu Lys Cys Phe Ser Val Asp Glu Ile Val Gln Pro
```

```
385                 390                 395                 400
Asp Pro Pro Ile Ala Leu Asn Trp Thr Leu Leu Asn Val Ser Leu Thr
                405                 410                 415

Gly Ile His Ala Asp Ile Gln Val Arg Trp Glu Ala Pro Arg Asn Ala
                420                 425                 430

Asp Ile Gln Lys Gly Trp Met Val Leu Glu Tyr Glu Leu Gln Tyr Lys
                435                 440                 445

Glu Val Asn Glu Thr Lys Trp Lys Met Met Asp Pro Ile Leu Thr Thr
            450                 455                 460

Ser Val Pro Val Tyr Ser Leu Lys Val Asp Lys Glu Tyr Glu Val Arg
465                 470                 475                 480

Val Arg Ser Lys Gln Arg Asn Ser Gly Asn Tyr Gly Glu Phe Ser Glu
                485                 490                 495

Val Leu Tyr Val Thr Leu Pro Gln Met Ser Gln
                500                 505
```

<210> SEQ ID NO 43
<211> LENGTH: 499
<212> TYPE: PRT
<213> ORGANISM: artificial sequence
<220> FEATURE:
<223> OTHER INFORMATION: Fusion proteins

<400> SEQUENCE: 43

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ser Glu His Gln
                20                  25                  30

Leu Leu His Asp Lys Gly Lys Ser Ile Gln Asp Leu Arg Arg Arg Phe
            35                  40                  45

Phe Leu His His Leu Ile Ala Glu Ile His Thr Ala Glu Ile Gly Gly
        50                  55                  60

Gly Gly Ser Gly Gly Gly Ser Gly Gly Gly Ser Gly Gly Gly
65                  70                  75                  80

Gly Ser Asp Asp Val Met Thr Lys Glu Glu Gln Ile Phe Leu Leu His
                85                  90                  95

Arg Ala Gln Ala Gln Cys Glu Lys Arg Leu Lys Glu Val Leu Gln Arg
                100                 105                 110

Pro Ala Ser Ile Met Glu Ser Asp Lys Gly Trp Thr Ser Ala Ser Thr
            115                 120                 125

Ser Gly Lys Pro Arg Lys Asp Lys Ala Ser Gly Lys Leu Tyr Pro Glu
        130                 135                 140

Ser Glu Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Ile Tyr Asp Phe
            180                 185                 190

Asn His Lys Gly His Ala Tyr Arg Arg Cys Asp Arg Asn Gly Ser Trp
        195                 200                 205

Glu Leu Val Pro Gly His Asn Arg Thr Trp Ala Asn Tyr Ser Glu Cys
            210                 215                 220

Val Lys Phe Leu Thr Asn Glu Thr Arg Glu Arg Glu Val Phe Asp Arg
225                 230                 235                 240

Leu Gly Gly Gly Gly Ser Gly Gly Gly Gly Ser Gly Gly Gly Gly Ser
```

245                 250                 255
Gly Gly Gly Gly Ser Phe Ser Gly Ser Glu Ala Thr Ala Ala Ile Leu
                260                 265                 270

Ser Arg Ala Pro Trp Ser Leu Gln Ser Val Asn Pro Gly Leu Lys Thr
                275                 280                 285

Asn Ser Ser Lys Glu Pro Lys Phe Thr Lys Cys Arg Ser Pro Glu Arg
            290                 295                 300

Glu Thr Phe Ser Cys His Trp Thr Asp Glu Val His His Gly Thr Lys
305                 310                 315                 320

Asn Leu Gly Pro Ile Gln Leu Phe Tyr Thr Arg Arg Asn Thr Gln Glu
                325                 330                 335

Trp Thr Gln Glu Trp Lys Glu Cys Pro Asp Tyr Val Ser Ala Gly Glu
                340                 345                 350

Asn Ser Cys Tyr Phe Asn Ser Ser Phe Thr Ser Ile Ala Ile Pro Tyr
                355                 360                 365

Cys Ile Lys Leu Thr Ser Asn Gly Gly Thr Val Asp Glu Lys Cys Phe
            370                 375                 380

Ser Val Asp Glu Ile Val Gln Pro Asp Pro Pro Ile Ala Leu Asn Trp
385                 390                 395                 400

Thr Leu Leu Asn Val Ser Leu Thr Gly Ile His Ala Asp Ile Gln Val
                405                 410                 415

Arg Trp Glu Ala Pro Arg Asn Ala Asp Ile Gln Lys Gly Trp Met Val
                420                 425                 430

Leu Glu Tyr Glu Leu Gln Tyr Lys Glu Val Asn Glu Thr Lys Trp Lys
                435                 440                 445

Met Met Asp Pro Ile Leu Thr Thr Ser Val Pro Val Tyr Ser Leu Lys
            450                 455                 460

Val Asp Lys Glu Tyr Glu Val Arg Val Arg Ser Lys Gln Arg Asn Ser
465                 470                 475                 480

Gly Asn Tyr Gly Glu Phe Ser Glu Val Leu Tyr Val Thr Leu Pro Gln
                485                 490                 495

Met Ser Gln

<210> SEQ ID NO 44
<211> LENGTH: 340
<212> TYPE: PRT
<213> ORGANISM: artificial sequence
<220> FEATURE:
<223> OTHER INFORMATION: Fusion proteins

<400> SEQUENCE: 44

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ser Glu His Gln
                20                  25                  30

Leu Leu His Asp Lys Gly Lys Ser Ile Gln Asp Leu Arg Arg Arg Phe
                35                  40                  45

Phe Leu His His Leu Ile Ala Glu Ile His Thr Ala Glu Ile Gly Gly
            50                  55                  60

Gly Gly Ser Gly Gly Gly Gly Ser Gly Gly Gly Gly Ser Gly Gly Gly
65                  70                  75                  80

Gly Ser Gly Gly Gly Gly Ser Gly Gly Gly Gly Ser Gly Gly Gly Gly
                85                  90                  95

Ser Gly Gly Gly Gly Ser Phe Ser Gly Ser Glu Ala Thr Ala Ala Ile
                100                 105                 110

Leu Ser Arg Ala Pro Trp Ser Leu Gln Ser Val Asn Pro Gly Leu Lys
            115                 120                 125

Thr Asn Ser Ser Lys Glu Pro Lys Phe Thr Lys Cys Arg Ser Pro Glu
    130                 135                 140

Arg Glu Thr Phe Ser Cys His Trp Thr Asp Glu Val His His Gly Thr
145                 150                 155                 160

Lys Asn Leu Gly Pro Ile Gln Leu Phe Tyr Thr Arg Arg Asn Thr Gln
                165                 170                 175

Glu Trp Thr Gln Glu Trp Lys Glu Cys Pro Asp Tyr Val Ser Ala Gly
            180                 185                 190

Glu Asn Ser Cys Tyr Phe Asn Ser Ser Phe Thr Ser Ile Ala Ile Pro
        195                 200                 205

Tyr Cys Ile Lys Leu Thr Ser Asn Gly Gly Thr Val Asp Glu Lys Cys
    210                 215                 220

Phe Ser Val Asp Glu Ile Val Gln Pro Asp Pro Pro Ile Ala Leu Asn
225                 230                 235                 240

Trp Thr Leu Leu Asn Val Ser Leu Thr Gly Ile His Ala Asp Ile Gln
                245                 250                 255

Val Arg Trp Glu Ala Pro Arg Asn Ala Asp Ile Gln Lys Gly Trp Met
            260                 265                 270

Val Leu Glu Tyr Glu Leu Gln Tyr Lys Glu Val Asn Glu Thr Lys Trp
        275                 280                 285

Lys Met Met Asp Pro Ile Leu Thr Thr Ser Val Pro Val Tyr Ser Leu
    290                 295                 300

Lys Val Asp Lys Glu Tyr Glu Val Arg Val Arg Ser Lys Gln Arg Asn
305                 310                 315                 320

Ser Gly Asn Tyr Gly Glu Phe Ser Glu Val Leu Tyr Val Thr Leu Pro
                325                 330                 335

Gln Met Ser Gln
            340

<210> SEQ ID NO 45
<211> LENGTH: 241
<212> TYPE: PRT
<213> ORGANISM: artificial sequence
<220> FEATURE:
<223> OTHER INFORMATION: Fusion proteins

<400> SEQUENCE: 45

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ser Glu His Gln
            20                  25                  30

Leu Leu His Asp Lys Gly Lys Ser Ile Gln Asp Leu Arg Arg Arg Phe
        35                  40                  45

Phe Leu His His Leu Ile Ala Glu Ile His Thr Ala Glu Ile Gly Gly
    50                  55                  60

Gly Gly Ser Gly Gly Gly Gly Ser Gly Gly Gly Gly Ser Gly Gly Gly
65                  70                  75                  80

Gly Ser Asp Asp Val Met Thr Lys Glu Glu Gln Ile Phe Leu Leu His
                85                  90                  95

Arg Ala Gln Ala Gln Cys Glu Lys Arg Leu Lys Glu Val Leu Gln Arg
            100                 105                 110

Pro Ala Ser Ile Met Glu Ser Asp Lys Gly Trp Thr Ser Ala Ser Thr
        115                 120                 125

```
Ser Gly Lys Pro Arg Lys Asp Lys Ala Ser Gly Lys Leu Tyr Pro Glu
130                 135                 140

Ser Glu Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Ile Tyr Asp Phe
                180                 185                 190

Asn His Lys Gly His Ala Tyr Arg Arg Cys Asp Arg Asn Gly Ser Trp
                195                 200                 205

Glu Leu Val Pro Gly His Asn Arg Thr Trp Ala Asn Tyr Ser Glu Cys
                210                 215                 220

Val Lys Phe Leu Thr Asn Glu Thr Arg Glu Arg Glu Val Phe Asp Arg
225                 230                 235                 240

Leu
```

<210> SEQ ID NO 46
<211> LENGTH: 249
<212> TYPE: PRT
<213> ORGANISM: artificial sequence
<220> FEATURE:
<223> OTHER INFORMATION: Fusion proteins

<400> SEQUENCE: 46

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ser Glu His Gln
                20                  25                  30

Leu Leu His Asp Lys Gly Lys Ser Ile Gln Asp Leu Arg Arg Arg Phe
                35                  40                  45

Phe Leu His His Leu Ile Ala Glu Ile His Thr Ala Glu Ile Gly Gly
            50                  55                  60

Gly Gly Ser Gly Gly Gly Gly Ser Gly Gly Gly Gly Ser Gly Gly Gly
65                  70                  75                  80

Gly Ser Asp Asp Val Met Thr Lys Glu Glu Gln Ile Phe Leu Leu His
                85                  90                  95

Arg Ala Gln Ala Gln Cys Glu Lys Arg Leu Lys Glu Val Leu Gln Arg
                100                 105                 110

Pro Ala Ser Ile Met Glu Ser Asp Lys Gly Trp Thr Ser Ala Ser Thr
                115                 120                 125

Ser Gly Lys Pro Arg Lys Asp Lys Ala Ser Gly Lys Leu Tyr Pro Glu
130                 135                 140

Ser Glu Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Ile Tyr Asp Phe
                180                 185                 190

Asn His Lys Gly His Ala Tyr Arg Arg Cys Asp Arg Asn Gly Ser Trp
                195                 200                 205

Glu Leu Val Pro Gly His Asn Arg Thr Trp Ala Asn Tyr Ser Glu Cys
                210                 215                 220

Val Lys Phe Leu Thr Asn Glu Thr Arg Glu Arg Glu Val Phe Asp Arg
225                 230                 235                 240
```

Leu Thr Gly His His His His His His
                245

<210> SEQ ID NO 47
<211> LENGTH: 257
<212> TYPE: PRT
<213> ORGANISM: artificial sequence
<220> FEATURE:
<223> OTHER INFORMATION: Fusion proteins

<400> SEQUENCE: 47

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Ala Val Ser Glu His Gln Leu Leu His Asp Lys Gly Lys Ser
        35                  40                  45

Ile Gln Asp Leu Arg Arg Arg Phe Phe Leu His His Leu Ile Ala Glu
    50                  55                  60

Ile His Thr Ala Glu Ile Gly Gly Gly Gly Ser Gly Gly Gly Gly Ser
65                  70                  75                  80

Gly Gly Gly Gly Ser Gly Gly Gly Ser Asp Asp Val Met Thr Lys
                85                  90                  95

Glu Glu Gln Ile Phe Leu Leu His Arg Ala Gln Ala Gln Cys Glu Lys
                100                 105                 110

Arg Leu Lys Glu Val Leu Gln Arg Pro Ala Ser Ile Met Glu Ser Asp
            115                 120                 125

Lys Gly Trp Thr Ser Ala Ser Thr Ser Gly Lys Pro Arg Lys Asp Lys
    130                 135                 140

Ala Ser Gly Lys Leu Tyr Pro Glu Ser Glu Asp Lys Glu Ala Pro
145                 150                 155                 160

Thr Gly Ser Arg Tyr Arg Gly Arg Pro Cys Leu Pro Glu Trp Asp His
                165                 170                 175

Ile Leu Cys Trp Pro Leu Gly Ala Pro Gly Glu Val Val Ala Val Pro
            180                 185                 190

Cys Pro Asp Tyr Ile Tyr Asp Phe Asn His Lys Gly His Ala Tyr Arg
        195                 200                 205

Arg Cys Asp Arg Asn Gly Ser Trp Glu Leu Val Pro Gly His Asn Arg
    210                 215                 220

Thr Trp Ala Asn Tyr Ser Glu Cys Val Lys Phe Leu Thr Asn Glu Thr
225                 230                 235                 240

Arg Glu Arg Glu Val Phe Asp Arg Leu Thr Gly His His His His His
                245                 250                 255

His

<210> SEQ ID NO 48
<211> LENGTH: 249
<212> TYPE: PRT
<213> ORGANISM: artificial sequence
<220> FEATURE:
<223> OTHER INFORMATION: Fusion proteins

<400> SEQUENCE: 48

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Ala Val Ser Glu His Gln Leu Leu His Asp Lys Gly Lys Ser
                35                  40                  45

Ile Gln Asp Leu Arg Arg Arg Phe Phe Leu His His Leu Ile Ala Glu
 50                  55                  60

Ile His Thr Ala Glu Ile Gly Gly Gly Ser Gly Gly Gly Ser
 65                  70                  75                  80

Gly Gly Gly Gly Ser Gly Gly Gly Ser Asp Asp Val Met Thr Lys
                 85                  90                  95

Glu Glu Gln Ile Phe Leu Leu His Arg Ala Gln Ala Gln Cys Glu Lys
                100                 105                 110

Arg Leu Lys Glu Val Leu Gln Arg Pro Ala Ser Ile Met Glu Ser Asp
            115                 120                 125

Lys Gly Trp Thr Ser Ala Ser Thr Ser Gly Lys Pro Arg Lys Asp Lys
130                 135                 140

Ala Ser Gly Lys Leu Tyr Pro Glu Ser Glu Glu Asp Lys Glu Ala Pro
145                 150                 155                 160

Thr Gly Ser Arg Tyr Arg Gly Arg Pro Cys Leu Pro Glu Trp Asp His
                165                 170                 175

Ile Leu Cys Trp Pro Leu Gly Ala Pro Gly Glu Val Val Ala Val Pro
            180                 185                 190

Cys Pro Asp Tyr Ile Tyr Asp Phe Asn His Lys Gly His Ala Tyr Arg
            195                 200                 205

Arg Cys Asp Arg Asn Gly Ser Trp Glu Leu Val Pro Gly His Asn Arg
        210                 215                 220

Thr Trp Ala Asn Tyr Ser Glu Cys Val Lys Phe Leu Thr Asn Glu Thr
225                 230                 235                 240

Arg Glu Arg Glu Val Phe Asp Arg Leu
                245

<210> SEQ ID NO 49
<211> LENGTH: 328
<212> TYPE: PRT
<213> ORGANISM: artificial sequence
<220> FEATURE:
<223> OTHER INFORMATION: Fusion proteins

<400> SEQUENCE: 49

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
                20                  25                  30

Arg Leu Ala Val Ser Glu His Gln Leu Leu His Asp Lys Gly Lys Ser
                35                  40                  45

Ile Gln Asp Leu Arg Arg Arg Phe Phe Leu His His Leu Ile Ala Glu
 50                  55                  60

Ile His Thr Ala Glu Ile Gly Gly Gly Ser Gly Gly Gly Ser
 65                  70                  75                  80

Gly Gly Gly Gly Ser Gly Gly Gly Ser Phe Ser Gly Ser Glu Ala
                 85                  90                  95

Thr Ala Ala Ile Leu Ser Arg Ala Pro Trp Ser Leu Gln Ser Val Asn
                100                 105                 110

Pro Gly Leu Lys Thr Asn Ser Ser Lys Glu Pro Lys Phe Thr Lys Cys
            115                 120                 125

Arg Ser Pro Glu Arg Glu Thr Phe Ser Cys His Trp Thr Asp Glu Val
130                 135                 140

His His Gly Thr Lys Asn Leu Gly Pro Ile Gln Leu Phe Tyr Thr Arg
145                 150                 155                 160

Arg Asn Thr Gln Glu Trp Thr Gln Glu Trp Lys Glu Cys Pro Asp Tyr
            165                 170                 175

Val Ser Ala Gly Glu Asn Ser Cys Tyr Phe Asn Ser Ser Phe Thr Ser
            180                 185                 190

Ile Ala Ile Pro Tyr Cys Ile Lys Leu Thr Ser Asn Gly Gly Thr Val
            195                 200                 205

Asp Glu Lys Cys Phe Ser Val Asp Glu Ile Val Gln Pro Asp Pro Pro
    210                 215                 220

Ile Ala Leu Asn Trp Thr Leu Leu Asn Val Ser Leu Thr Gly Ile His
225                 230                 235                 240

Ala Asp Ile Gln Val Arg Trp Glu Ala Pro Arg Asn Ala Asp Ile Gln
            245                 250                 255

Lys Gly Trp Met Val Leu Glu Tyr Glu Leu Gln Tyr Lys Glu Val Asn
            260                 265                 270

Glu Thr Lys Trp Lys Met Met Asp Pro Ile Leu Thr Thr Ser Val Pro
        275                 280                 285

Val Tyr Ser Leu Lys Val Asp Lys Glu Tyr Glu Val Arg Val Arg Ser
    290                 295                 300

Lys Gln Arg Asn Ser Gly Asn Tyr Gly Glu Phe Ser Glu Val Leu Tyr
305                 310                 315                 320

Val Thr Leu Pro Gln Met Ser Gln
                325

<210> SEQ ID NO 50
<211> LENGTH: 507
<212> TYPE: PRT
<213> ORGANISM: artificial sequence
<220> FEATURE:
<223> OTHER INFORMATION: Fusion proteins

<400> SEQUENCE: 50

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Ala Val Ser Glu His Gln Leu Leu His Asp Lys Gly Lys Ser
            35                  40                  45

Ile Gln Asp Leu Arg Arg Arg Phe Phe Leu His His Leu Ile Ala Glu
    50                  55                  60

Ile His Thr Ala Glu Ile Gly Gly Gly Ser Gly Gly Gly Gly Gly Ser
65                  70                  75                  80

Gly Gly Gly Gly Ser Gly Gly Gly Ser Asp Asp Val Met Thr Lys
            85                  90                  95

Glu Glu Gln Ile Phe Leu Leu His Arg Ala Gln Ala Gln Cys Glu Lys
            100                 105                 110

Arg Leu Lys Glu Val Leu Gln Arg Pro Ala Ser Ile Met Glu Ser Asp
            115                 120                 125

Lys Gly Trp Thr Ser Ala Ser Thr Ser Gly Lys Pro Arg Lys Asp Lys
    130                 135                 140

Ala Ser Gly Lys Leu Tyr Pro Glu Ser Glu Glu Asp Lys Glu Ala Pro
145                 150                 155                 160

Thr Gly Ser Arg Tyr Arg Gly Arg Pro Cys Leu Pro Glu Trp Asp His
            165                 170                 175

```
Ile Leu Cys Trp Pro Leu Gly Ala Pro Gly Glu Val Val Ala Val Pro
            180                 185                 190

Cys Pro Asp Tyr Lys Tyr Asp Phe Asn His Lys Gly His Ala Tyr Arg
            195                 200                 205

Arg Cys Asp Arg Asn Gly Ser Trp Glu Leu Val Pro Gly His Asn Arg
        210                 215                 220

Thr Trp Ala Asn Tyr Ser Glu Cys Val Lys Phe Leu Thr Asn Glu Thr
225                 230                 235                 240

Arg Glu Arg Glu Val Phe Asp Arg Leu Gly Gly Gly Ser Gly Gly
                245                 250                 255

Gly Gly Ser Gly Gly Gly Gly Ser Gly Gly Gly Gly Ser Phe Ser Gly
            260                 265                 270

Ser Glu Ala Thr Ala Ala Ile Leu Ser Arg Ala Pro Trp Ser Leu Gln
            275                 280                 285

Ser Val Asn Pro Gly Leu Lys Thr Asn Ser Ser Lys Glu Pro Lys Phe
        290                 295                 300

Thr Lys Cys Arg Ser Pro Glu Arg Glu Thr Phe Ser Cys His Trp Thr
305                 310                 315                 320

Asp Glu Val His His Gly Thr Lys Asn Leu Gly Pro Ile Gln Leu Phe
                325                 330                 335

Tyr Thr Arg Arg Asn Thr Gln Glu Trp Thr Gln Glu Trp Lys Glu Cys
            340                 345                 350

Pro Asp Tyr Val Ser Ala Gly Glu Asn Ser Cys Tyr Phe Asn Ser Ser
        355                 360                 365

Phe Thr Ser Ile Ala Ile Pro Tyr Cys Ile Lys Leu Thr Ser Asn Gly
370                 375                 380

Gly Thr Val Asp Glu Lys Cys Phe Ser Val Asp Glu Ile Val Gln Pro
385                 390                 395                 400

Asp Pro Pro Ile Ala Leu Asn Trp Thr Leu Leu Asn Val Ser Leu Thr
            405                 410                 415

Gly Ile His Ala Asp Ile Gln Val Arg Trp Glu Ala Pro Arg Asn Ala
            420                 425                 430

Asp Ile Gln Lys Gly Trp Met Val Leu Glu Tyr Glu Leu Gln Tyr Lys
        435                 440                 445

Glu Val Asn Glu Thr Lys Trp Lys Met Met Asp Pro Ile Leu Thr Thr
450                 455                 460

Ser Val Pro Val Tyr Ser Leu Lys Val Asp Lys Glu Tyr Glu Val Arg
465                 470                 475                 480

Val Arg Ser Lys Gln Arg Asn Ser Gly Asn Tyr Gly Glu Phe Ser Glu
            485                 490                 495

Val Leu Tyr Val Thr Leu Pro Gln Met Ser Gln
            500                 505

<210> SEQ ID NO 51
<211> LENGTH: 499
<212> TYPE: PRT
<213> ORGANISM: artificial sequence
<220> FEATURE:
<223> OTHER INFORMATION: Fusion proteins

<400> SEQUENCE: 51

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Val Ser Glu His Gln
            20                  25                  30
```

```
Leu Leu His Asp Lys Gly Lys Ser Ile Gln Asp Leu Arg Arg Phe
         35                  40                  45

Phe Leu His His Leu Ile Ala Glu Ile His Thr Ala Glu Ile Gly Gly
 50                  55                  60

Gly Gly Ser Gly Gly Gly Ser Gly Gly Gly Ser Gly Gly
 65                  70                  75                  80

Gly Ser Asp Asp Val Met Thr Lys Glu Gln Ile Phe Leu Leu His
                     85                  90                  95

Arg Ala Gln Ala Gln Cys Glu Lys Arg Leu Lys Glu Val Leu Gln Arg
                100                 105                 110

Pro Ala Ser Ile Met Glu Ser Asp Lys Gly Trp Thr Ser Ala Ser Thr
                115                 120                 125

Ser Gly Lys Pro Arg Lys Asp Lys Ala Ser Gly Lys Leu Tyr Pro Glu
130                 135                 140

Ser Glu Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Lys Tyr Asp Phe
                180                 185                 190

Asn His Lys Gly His Ala Tyr Arg Arg Cys Asp Arg Asn Gly Ser Trp
                195                 200                 205

Glu Leu Val Pro Gly His Asn Arg Thr Trp Ala Asn Tyr Ser Glu Cys
                210                 215                 220

Val Lys Phe Leu Thr Asn Glu Thr Arg Glu Arg Glu Val Phe Asp Arg
225                 230                 235                 240

Leu Gly Gly Gly Ser Gly Gly Gly Ser Gly Gly Gly Ser
                245                 250                 255

Gly Gly Gly Gly Ser Phe Ser Gly Ser Glu Ala Thr Ala Ala Ile Leu
                260                 265                 270

Ser Arg Ala Pro Trp Ser Leu Gln Ser Val Asn Pro Gly Leu Lys Thr
                275                 280                 285

Asn Ser Ser Lys Glu Pro Lys Phe Thr Lys Cys Arg Ser Pro Glu Arg
290                 295                 300

Glu Thr Phe Ser Cys His Trp Thr Asp Glu Val His Gly Thr Lys
305                 310                 315                 320

Asn Leu Gly Pro Ile Gln Leu Phe Tyr Thr Arg Arg Asn Thr Gln Glu
                325                 330                 335

Trp Thr Gln Glu Trp Lys Glu Cys Pro Asp Tyr Val Ser Ala Gly Glu
                340                 345                 350

Asn Ser Cys Tyr Phe Asn Ser Ser Phe Thr Ser Ile Ala Ile Pro Tyr
                355                 360                 365

Cys Ile Lys Leu Thr Ser Asn Gly Gly Thr Val Asp Glu Lys Cys Phe
370                 375                 380

Ser Val Asp Glu Ile Val Gln Pro Asp Pro Pro Ile Ala Leu Asn Trp
385                 390                 395                 400

Thr Leu Leu Asn Val Ser Leu Thr Gly Ile His Ala Asp Ile Gln Val
                405                 410                 415

Arg Trp Glu Ala Pro Arg Asn Ala Asp Ile Gln Lys Gly Trp Met Val
                420                 425                 430

Leu Glu Tyr Glu Leu Gln Tyr Lys Glu Val Asn Glu Thr Lys Trp Lys
                435                 440                 445

Met Met Asp Pro Ile Leu Thr Thr Ser Val Pro Val Tyr Ser Leu Lys
```

```
            450                 455                 460
Val Asp Lys Glu Tyr Glu Val Arg Val Arg Ser Lys Gln Arg Asn Ser
465                 470                 475                 480

Gly Asn Tyr Gly Glu Phe Ser Glu Val Leu Tyr Val Thr Leu Pro Gln
                    485                 490                 495

Met Ser Gln

<210> SEQ ID NO 52
<211> LENGTH: 257
<212> TYPE: PRT
<213> ORGANISM: artificial sequence
<220> FEATURE:
<223> OTHER INFORMATION: Fusion proteins

<400> SEQUENCE: 52

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
                20                  25                  30

Arg Leu Ala Val Ser Glu His Gln Leu Leu His Asp Lys Gly Lys Ser
            35                  40                  45

Ile Gln Asp Leu Arg Arg Arg Phe Phe Leu His His Leu Ile Ala Glu
        50                  55                  60

Ile His Thr Ala Glu Ile Gly Gly Gly Ser Gly Gly Gly Ser
65                  70                  75                  80

Gly Gly Gly Gly Ser Gly Gly Gly Ser Asp Asp Val Met Thr Lys
                85                  90                  95

Glu Glu Gln Ile Phe Leu Leu His Arg Ala Gln Ala Gln Cys Glu Lys
            100                 105                 110

Arg Leu Lys Glu Val Leu Gln Arg Pro Ala Ser Ile Met Glu Ser Asp
        115                 120                 125

Lys Gly Trp Thr Ser Ala Ser Thr Ser Gly Lys Pro Arg Lys Asp Lys
    130                 135                 140

Ala Ser Gly Lys Leu Tyr Pro Glu Ser Glu Asp Lys Glu Ala Pro
145                 150                 155                 160

Thr Gly Ser Arg Tyr Arg Gly Arg Pro Cys Leu Pro Glu Trp Asp His
                165                 170                 175

Ile Leu Cys Trp Pro Leu Gly Ala Pro Gly Glu Val Val Ala Val Pro
            180                 185                 190

Cys Pro Asp Tyr Lys Tyr Asp Phe Asn His Lys Gly His Ala Tyr Arg
        195                 200                 205

Arg Cys Asp Arg Asn Gly Ser Trp Glu Leu Val Pro Gly His Asn Arg
    210                 215                 220

Thr Trp Ala Asn Tyr Ser Glu Cys Val Lys Phe Leu Thr Asn Glu Thr
225                 230                 235                 240

Arg Glu Arg Glu Val Phe Asp Arg Leu Thr Gly His His His His
                245                 250                 255

His

<210> SEQ ID NO 53
<211> LENGTH: 249
<212> TYPE: PRT
<213> ORGANISM: artificial sequence
<220> FEATURE:
<223> OTHER INFORMATION: Fusion proteins

<400> SEQUENCE: 53
```

```
Met Ala Thr Gly Ser Arg Thr Ser Leu Leu Ala Phe Gly Leu Leu
1               5                   10                  15

Cys Leu Pro Trp Leu Gln Glu Gly Ser Ala Ala Val Ser Glu His Gln
                20                  25                  30

Leu Leu His Asp Lys Gly Lys Ser Ile Gln Asp Leu Arg Arg Arg Phe
            35                  40                  45

Phe Leu His His Leu Ile Ala Glu Ile His Thr Ala Glu Ile Gly Gly
        50                  55                  60

Gly Gly Ser Gly Gly Gly Ser Gly Gly Gly Ser Gly Gly Gly
65                  70                  75                  80

Gly Ser Asp Asp Val Met Thr Lys Glu Glu Gln Ile Phe Leu Leu His
                85                  90                  95

Arg Ala Gln Ala Gln Cys Glu Lys Arg Leu Lys Glu Val Leu Gln Arg
            100                 105                 110

Pro Ala Ser Ile Met Glu Ser Asp Lys Gly Trp Thr Ser Ala Ser Thr
            115                 120                 125

Ser Gly Lys Pro Arg Lys Asp Lys Ala Ser Gly Lys Leu Tyr Pro Glu
        130                 135                 140

Ser Glu Asp Lys Glu Ala Pro Thr Gly Ser Arg Tyr Arg Gly Arg
145                 150                 155                 160

Pro Cys Leu Pro Glu Trp Asp His Ile Leu Cys Trp Pro Leu Gly Ala
                165                 170                 175

Pro Gly Glu Val Val Ala Val Pro Cys Pro Asp Tyr Lys Tyr Asp Phe
                180                 185                 190

Asn His Lys Gly His Ala Tyr Arg Arg Cys Asp Arg Asn Gly Ser Trp
            195                 200                 205

Glu Leu Val Pro Gly His Asn Arg Thr Trp Ala Asn Tyr Ser Glu Cys
            210                 215                 220

Val Lys Phe Leu Thr Asn Glu Thr Arg Glu Arg Glu Val Phe Asp Arg
225                 230                 235                 240

Leu Thr Gly His His His His His His
                245

<210> SEQ ID NO 54
<211> LENGTH: 34
<212> TYPE: PRT
<213> ORGANISM: artificial sequence
<220> FEATURE:
<223> OTHER INFORMATION: PTH 1-34

<400> SEQUENCE: 54

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 55
<211> LENGTH: 28
<212> TYPE: PRT
<213> ORGANISM: artificial sequence
<220> FEATURE:
<223> OTHER INFORMATION: PTH ECD signal peptide

<400> SEQUENCE: 55

Met Gly Thr Ala Arg Ile Ala Pro Gly Leu Ala Leu Leu Leu Cys Cys
1               5                   10                  15
```

Pro Val Leu Ser Ser Ala Tyr Ala Leu Val Asp Ala
              20                  25

<210> SEQ ID NO 56
<211> LENGTH: 593
<212> TYPE: PRT
<213> ORGANISM: artificial sequence
<220> FEATURE:
<223> OTHER INFORMATION: PTH receptor full length

<400> SEQUENCE: 56

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
              20                  25                  30

Thr Lys Glu Glu Gln Ile Phe Leu Leu His Arg Ala Gln Ala Gln Cys
          35                  40                  45

Glu Lys Arg Leu Lys Glu Val Leu Gln Arg Pro Ala Ser Ile Met Glu
      50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Glu Asp Lys Glu
                  85                  90                  95

Ala Pro Thr Gly Ser Arg Tyr Arg Gly Arg Pro Cys Leu Pro Glu Trp
              100                 105                 110

Asp His Ile Leu Cys Trp Pro Leu Gly Ala Pro Gly Glu Val Val Ala
          115                 120                 125

Val Pro Cys Pro Asp Tyr Ile Tyr Asp Phe Asn His Lys Gly His Ala
      130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                  165                 170                 175

Glu Thr Arg Glu Arg Glu Val Phe Asp Arg Leu Gly Met Ile Tyr Thr
              180                 185                 190

Val Gly Tyr Ser Val Ser Leu Ala Ser Leu Thr Val Ala Val Leu Ile
          195                 200                 205

Leu Ala Tyr Phe Arg Arg Leu His Cys Thr Arg Asn Tyr Ile His Met
      210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                  245                 250                 255

Thr Glu Glu Leu Arg Ala Ile Ala Gln Ala Pro Pro Pro Ala
              260                 265                 270

Thr Ala Ala Gly Tyr Ala Gly Cys Arg Val Ala Val Thr Phe Phe
          275                 280                 285

Leu Tyr Phe Leu Ala Thr Asn Tyr Tyr Trp Ile Leu Val Glu Gly Leu
      290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                  325                 330                 335

Ala Val Trp Val Ser Val Arg Ala Thr Leu Ala Asn Thr Gly Cys Trp
              340                 345                 350

```
Asp Leu Ser Ser Gly Asn Lys Lys Trp Ile Ile Gln Val Pro Ile Leu
            355                 360                 365
Ala Ser Ile Val Leu Asn Phe Ile Leu Phe Ile Asn Ile Val Arg Val
        370                 375                 380
Leu Ala Thr Lys Leu Arg Glu Thr Asn Ala Gly Arg Cys Asp Thr Arg
385                 390                 395                 400
Gln Gln Tyr Arg Lys Leu Leu Lys Ser Thr Leu Val Leu Met Pro Leu
                405                 410                 415
Phe Gly Val His Tyr Ile Val Phe Met Ala Thr Pro Tyr Thr Glu Val
            420                 425                 430
Ser Gly Thr Leu Trp Gln Val Gln Met His Tyr Glu Met Leu Phe Asn
        435                 440                 445
Ser Phe Gln Gly Phe Phe Val Ala Ile Ile Tyr Cys Phe Cys Asn Gly
    450                 455                 460
Glu Val Gln Ala Glu Ile Lys Lys Ser Trp Ser Arg Trp Thr Leu Ala
465                 470                 475                 480
Leu Asp Phe Lys Arg Lys Ala Arg Ser Gly Ser Ser Tyr Ser Tyr
                485                 490                 495
Gly Pro Met Val Ser His Thr Ser Val Thr Asn Val Gly Pro Arg Val
            500                 505                 510
Gly Leu Gly Leu Pro Leu Ser Pro Arg Leu Leu Pro Thr Ala Thr Thr
        515                 520                 525
Asn Gly His Pro Gln Leu Pro Gly His Ala Lys Pro Gly Thr Pro Ala
    530                 535                 540
Leu Glu Thr Leu Glu Thr Thr Pro Pro Ala Met Ala Ala Pro Lys Asp
545                 550                 555                 560
Asp Gly Phe Leu Asn Gly Ser Cys Ser Gly Leu Asp Glu Glu Ala Ser
                565                 570                 575
Gly Pro Glu Arg Pro Pro Ala Leu Leu Gln Glu Glu Trp Glu Thr Val
            580                 585                 590
Met

<210> SEQ ID NO 57
<211> LENGTH: 115
<212> TYPE: PRT
<213> ORGANISM: artificial sequence
<220> FEATURE:
<223> OTHER INFORMATION: Fusion proteins

<400> SEQUENCE: 57

Met Ile Pro Ala Lys Asp Met Ala Lys Val Met Ile Val Met Leu Ala
1               5                   10                  15
Ile Cys Phe Leu Thr Lys Ser Asp Gly Lys Ser Val Lys Lys Arg Ser
            20                  25                  30
Val Ser Glu Ile Gln Leu Met His Asn Leu Gly Lys His Leu Asn Ser
        35                  40                  45
Met Glu Arg Val Glu Trp Leu Arg Lys Lys Leu Gln Asp Val His Asn
    50                  55                  60
Phe Val Ala Leu Gly Ala Pro Leu Ala Pro Arg Asp Ala Gly Ser Gln
65                  70                  75                  80
Arg Pro Arg Lys Lys Glu Asp Asn Val Leu Val Glu Ser His Glu Lys
                85                  90                  95
Ser Leu Gly Glu Ala Asp Lys Ala Asp Val Asn Val Leu Thr Lys Ala
            100                 105                 110
```

Lys Ser Gln
        115

<210> SEQ ID NO 58
<211> LENGTH: 834
<212> TYPE: DNA
<213> ORGANISM: artificial sequence
<220> FEATURE:
<223> OTHER INFORMATION: Fusion proteins

<400> SEQUENCE: 58
aaaagtcacc atttaagggg tctgcagtcc aattcatcag ttgtctttag tttactcagc    60
atcagctact aacatacctg aacgaagatc ttgttctaag acattgtatg tgaagatgat   120
acctgcaaaa gacatggcta agttatgat tgtcatgttg caatttgtt ttcttacaaa    180
atcggatggg aaatctgtta agaagagatc tgtgagtgaa atacagctta tgcataacct   240
gggaaaacat ctgaactcga tggagagagt agaatggctg cgtaagaagc tgcaggatgt   300
gcacaatttt gttgcccttg gagctcctct agctcccaga gatgctggtt cccagaggcc   360
ccgaaaaaag gaagacaatg tcttggttga gagccatgaa aaagtcttg gagaggcaga   420
caaagctgat gtgaatgtat taactaaagc taaatcccag tgaaaatgaa acagatatt   480
gtcagagttc tgctctagac agtgtagggc aacaatacat gctgctaatt caaagctcta   540
ttaagatttc caagtgccaa tatttctgat ataacaaact acatgtaatc catcactagc   600
catgataact gcaattttaa ttgattattc tgattccact tttattcatt tgagttattt   660
taattatctt ttctattgtt tattcttttt aaagtatgtt attgcataat ttataaaaga   720
ataaaattgc acttttaaac ctctcttcta ccttaaaatg taaaacaaaa atgtaatgat   780
cataagtcta ataaatgaa gtatttctca ctcattgcaa gtaaaaaaaa aaaa           834

<210> SEQ ID NO 59
<211> LENGTH: 102
<212> TYPE: DNA
<213> ORGANISM: artificial sequence
<220> FEATURE:
<223> OTHER INFORMATION: Fusion proteins

<400> SEQUENCE: 59
tctgtgagtg aaatacagct tatgcataac ctgggaaaac atctgaactc gatggagaga    60
gtagaatggc tgcgtaagaa gctgcaggat gtgcacaatt tt                       102

<210> SEQ ID NO 60
<211> LENGTH: 31
<212> TYPE: PRT
<213> ORGANISM: artificial sequence
<220> FEATURE:
<223> OTHER INFORMATION: Fusion proteins

<400> SEQUENCE: 60

Met Ile Pro Ala Lys Asp Met Ala Lys Val Met Ile Val Met Leu Ala
1               5                   10                  15
Ile Cys Phe Leu Thr Lys Ser Asp Gly Lys Ser Val Lys Lys Arg
            20                  25                  30

<210> SEQ ID NO 61
<211> LENGTH: 95
<212> TYPE: DNA
<213> ORGANISM: artificial sequence
<220> FEATURE:
<223> OTHER INFORMATION: Fusion proteins

<400> SEQUENCE: 61

| atgatacctg caaaagacat ggctaaagtt atgattgtca tgttggcaat ttgttttctt | 60 |
| acaaaatcgg atgggaaatc tgttaagaag agatc | 95 |

<210> SEQ ID NO 62
<211> LENGTH: 2007
<212> TYPE: DNA
<213> ORGANISM: artificial sequence
<220> FEATURE:
<223> OTHER INFORMATION: Fusion proteins

<400> SEQUENCE: 62

| ggagcggcag acgccgaggg ccggcggcgg cggctgcccc gagggacgcg gccctaggcg | 60 |
| gtggcgatgg ggaccgcccg gatcgcaccc ggcctggcgc tcctgctctg ctgcccgtg | 120 |
| ctcagctccg cgtacgcgct ggtggatgca gatgacgtca tgactaaaga ggaacagatc | 180 |
| ttcctgctgc accgtgctca ggcccagtgc gaaaaacggc tcaaggaggt cctgcagagg | 240 |
| ccagccagca taatggaatc agacaaggga tggacatctg cgtccacatc agggaagccc | 300 |
| aggaaagata aggcatctgg gaagctctac cctgagtctg aggaggacaa ggaggcaccc | 360 |
| actggcagca ggtaccgagg cgccccctgt ctgccggaat gggaccacat cctgtgctgg | 420 |
| ccgctggggg caccaggtga ggtggtggct gtgccctgtc cggactacat ttatgacttc | 480 |
| aatcacaaag gccatgccta cgacgcgtgt gaccgcaatg cagctggga gctggtgcct | 540 |
| gggcacaaca ggacgtgggc caactacagc gagtgtgtca atttctcac caatgagact | 600 |
| cgtgaacggg aggtgtttga ccgcctgggc atgatttaca ccgtgggcta ctccgtgtcc | 660 |
| ctggcgtccc tcaccgtagc tgtgctcatc ctggcctact taggcggct gcactgcacg | 720 |
| cgcaactaca tccacatgca cctgttcctg tccttcatgc tgcgcgccgt gagcatcttc | 780 |
| gtcaaggacg ctgtgctcta ctctggcgcc acgcttgatg aggctgagcg cctcaccgag | 840 |
| gaggagctgc gcgccatcgc ccaggcgccc cgccgcctg ccaccgccgc tgccggctac | 900 |
| gcgggctgca gggtggctgt gaccttcttc ctttacttcc tggccaccaa ctactactgg | 960 |
| attctggtgg aggggctgta cctgcacagc ctcatcttca tggccttctt ctcagagaag | 1020 |
| aagtacctgt ggggcttcac agtcttcggc tggggtctgc ccgctgtctt cgtggctgtg | 1080 |
| tgggtcagtg tcagagctac cctggccaac accgggtgct gggacttgag ctccgggaac | 1140 |
| aaaaagtgga tcatccaggt gcccatcctg gcctccattg tgctcaactt catcctcttc | 1200 |
| atcaatatcg tccgggtgct cgccaccaag ctgcgggaga ccaacgccgg ccggtgtgac | 1260 |
| acacggcagc agtaccggaa gctgctcaaa tccacgctgg tgctcatgcc cctctttggc | 1320 |
| gtccactaca ttgtcttcat ggccacacca tacaccgagg tctcagggac gctctggcaa | 1380 |
| gtccagatgc actatgagat gctcttcaac tccttccagg gattttttgt cgcaatcata | 1440 |
| tactgtttct gcaatggcga ggtacaagct gagatcaaga atcttggag ccgctggaca | 1500 |
| ctggcactgg acttcaagcg aaaggcacgc agcgggagca gcagctatag ctacggcccc | 1560 |
| atggtgtccc acacaagtgt gaccaatgtc ggcccccgtg tgggactcgg cctgccctc | 1620 |
| agccccgcc tactgcccac tgccaccacc aacggccacc ctcagctgcc tggccatgcc | 1680 |
| aagccaggga ccccagccct ggagaccctc gagaccacac cacctgccat ggctgctccc | 1740 |
| aaggacgatg ggttcctcaa cggctcctgc tcaggcctgg acgaggaggc ctctgggcct | 1800 |
| gagcggccac ctgccctgct acaggaagag tgggagacag tcatgtgacc aggcgctggg | 1860 |
| ggctggacct gctgacatag tggatggaca gatggaccaa aagatgggtg gttgaatgat | 1920 |

```
ttcccactca gggctggggc caagaggaaa acagggaaa aaagaaaaa aaaagaaaa    1980 aggaaaagga aaaaaaaaaa aaaaaaa                                    2007
```

<210> SEQ ID NO 63
<211> LENGTH: 477
<212> TYPE: DNA
<213> ORGANISM: artificial sequence
<220> FEATURE:
<223> OTHER INFORMATION: Fusion proteins

<400> SEQUENCE: 63

```
gatgacgtca tgactaaaga ggaacagatc ttcctgctgc accgtgctca ggcccagtgc    60
gaaaaacggc tcaaggaggt cctgcagagg ccagccagca taatggaatc agacaaggga   120
tggacatctg cgtccacatc agggaagccc aggaaagata aggcatctgg gaagctctac   180
cctgagtctg aggaggacaa ggaggcaccc actggcagca ggtaccgagg gcgcccctgt   240
ctgccggaat gggaccacat cctgtgctgg ccgctggggg caccaggtga ggtggtggct   300
gtgccctgtc cggactacat ttatgacttc aatcacaaag gccatgccta ccgacgctgt   360
gaccgcaatg gcagctggga gctggtgcct gggcacaaca ggacgtgggc caactacagc   420
gagtgtgtca aatttctcac caatgagact cgtgaacggg aggtgtttga ccgcctg     477
```

<210> SEQ ID NO 64
<211> LENGTH: 714
<212> TYPE: DNA
<213> ORGANISM: artificial sequence
<220> FEATURE:
<223> OTHER INFORMATION: Fusion proteins

<400> SEQUENCE: 64

```
ttttctggaa gtgaggccac agcagctatc cttagcagag caccctggag tctgcaaagt    60
gttaatccag gcctaaagac aaattcttct aaggagccta attcaccaa gtgccgttca   120
cctgagcgag agacttttc atgccactgg acagatgagg ttcatcatgg tacaaagaac   180
ctaggaccca tacagctgtt ctataccaga aggaacactc aagaatggac tcaagaatgg   240
aaagaatgcc ctgattatgt ttctgctggg gaaaacagct gttactttaa ttcatcgttt   300
acctccatcg caataccta ttgtatcaag ctaactagca atggtggtac agtggatgaa   360
aagtgtttct ctgttgatga atagtgcaa ccagatccac ccattgccct caactggact   420
ttactgaacg tcagtttaac tgggattcat gcagatatcc aagtgagatg gaagcacca   480
cgcaatgcag atattcagaa aggatggatg gttctggagt atgaacttca atacaaagaa   540
gtaaatgaaa ctaaatggaa aatgatggac cctatattga caacatcagt tccagtgtac   600
tcattgaaag tggataagga atatgaagtg cgtgtgagat ccaaacaacg aaactctgga   660
aattatggcg agttcagtga ggtgctctat gtaacacttc ctcagatgag ccaa          714
```

<210> SEQ ID NO 65
<211> LENGTH: 78
<212> TYPE: DNA
<213> ORGANISM: artificial sequence
<220> FEATURE:
<223> OTHER INFORMATION: Fusion proteins

<400> SEQUENCE: 65

```
atggctacag gctcccggac gtccctgctc ctggcttttg gcctgctctg cctgccctgg    60
cttcaagagg gcagtgcc                                                  78
```

<210> SEQ ID NO 66
<211> LENGTH: 1488
<212> TYPE: DNA
<213> ORGANISM: artificial sequence
<220> FEATURE:
<223> OTHER INFORMATION: Fusion proteins

<400> SEQUENCE: 66

| | |
|---|---|
| atgatacctg caaaagacat ggctaaagtt atgattgtca tgttggcaat ttgttttctt | 60 |
| acaaaatcgg atgggtctgt gagtgaaata cagcttatgc ataacctggg aaaacatctg | 120 |
| aactcgatgg agagagtaga atggctgcgt aagaagctgc aggatgtgca caattttggt | 180 |
| ggcggaggta gtggtggcgg aggtagcggt ggcggaggtt ctggtggcgg aggttccgat | 240 |
| gacgtcatga ctaaagagga acagatcttc ctgctgcacc gtgctcaggc ccagtgcgaa | 300 |
| aaacggctca aggaggtcct gcagaggcca gccagcataa tggaatcaga caagggatgg | 360 |
| acatctgcgt ccacatcagg gaagcccagg aaagataagg catctgggaa gctctaccct | 420 |
| gagtctgagg aggacaagga ggcacccact ggcagcaggt accagggcg ccctgtctg | 480 |
| ccggaatggg accacatcct gtgctggccg ctggggcac caggtgaggt ggtggctgtg | 540 |
| ccctgtccgg actacattta tgacttcaat cacaaaggcc atgcctaccg acgctgtgac | 600 |
| cgcaatggca gctgggagct ggtgcctggg cacaacagga cgtgggccaa ctacagcgag | 660 |
| tgtgtcaaat tctccaccaa tgagactcgt gaacgggagg tgtttgaccg cctgggtggc | 720 |
| ggaggtagtg gtggcggagg tagcggtggc ggaggttctg gtggcggagg ttcctttct | 780 |
| ggaagtgagg ccacagcagc tatccttagc agagcaccct ggagtctgca aagtgttaat | 840 |
| ccaggcctaa agacaaattc ttctaaggag cctaaattca ccaagtgccg ttcacctgag | 900 |
| cgagagactt tttcatgcca ctggacagat gaggttcatc atggtacaaa gaacctagga | 960 |
| cccatacagc tgttctatac cagaaggaac actcaagaat ggactcaaga atggaaagaa | 1020 |
| tgccctgatt atgtttctgc tggggaaaac agctgttact ttaattcatc gtttacctcc | 1080 |
| atcgcaatac cttattgtat caagctaact agcaatggtg gtacagtgga tgaaaagtgt | 1140 |
| ttctctgttg atgaaatagt gcaaccagat ccacccattg ccctcaactg gactttactg | 1200 |
| aacgtcagtt taactgggat tcatgcagat atccaagtga tgggaagc accacgcaat | 1260 |
| gcagatattc agaaaggatg gatggttctg gagtatgaac ttcaatacaa agaagtaaat | 1320 |
| gaaactaaat ggaaaatgat ggacccctata ttgacaacat cagttccagt gtactcattg | 1380 |
| aaagtggata ggaatatga agtgcgtgtg agatccaaac aacgaaactc tggaaattat | 1440 |
| ggcgagttca gtgaggtgct ctatgtaaca cttcctcaga tgagccaa | 1488 |

<210> SEQ ID NO 67
<211> LENGTH: 1506
<212> TYPE: DNA
<213> ORGANISM: artificial sequence
<220> FEATURE:
<223> OTHER INFORMATION: Fusion proteins

<400> SEQUENCE: 67

| | |
|---|---|
| atgatacctg caaaagacat ggctaaagtt atgattgtca tgttggcaat ttgttttctt | 60 |
| acaaaatcgg atgggaaatc tgttaagaag agatctgtga gtgaaataca gcttatgcat | 120 |
| aacctgggaa acatctgaa ctcgatggag agagtagaat ggctgcgtaa gaagctgcag | 180 |
| gatgtgcaca attttggtgg cggaggtagt ggtggcggag gtagcggtgg cggaggttct | 240 |
| ggtggcggag gttccgatga cgtcatgact aaagaggaac agatcttcct gctgcaccgt | 300 |

```
gctcaggccc agtgcgaaaa acggctcaag gaggtcctgc agaggccagc cagcataatg      360
gaatcagaca agggatggac atctgcgtcc acatcaggga agcccaggaa agataaggca      420
tctgggaagc tctaccctga gtctgaggag acaaggagg cacccactgg cagcaggtac       480
cgagggcgcc cctgtctgcc ggaatgggac acatcctgt gctggccgct gggggcacca       540
ggtgaggtgg tggctgtgcc ctgtccggac tacatttatg acttcaatca aaaggccat       600 gcctaccgac gctgtgaccg caatggcagc tgggagctgg tgcctgggca acaggacg       660 tgggccaact acagcgagtg tgtcaaattt ctcaccaatg agactcgtga acgggaggtg      720
tttgaccgcc tgggtggcgg aggtagtggt ggcggaggta gcggtggcgg aggttctggt      780
ggcggaggtt ccttttctgg aagtgaggcc acagcagcta tccttagcag agcaccctgg      840
agtctgcaaa gtgttaatcc aggcctaaag acaaattctt ctaaggagcc taaattcacc      900
aagtgccgtt cacctgagcg agagactttt tcatgccact ggacagatga ggttcatcat      960
ggtacaaaga acctaggacc catacagctg ttctatacca aaggaacac tcaagaatgg      1020 actcaagaat ggaaagaatg ccctgattat gtttctgctg gggaaaacag ctgttacttt      1080
aattcatcgt ttacctccat cgcaatacct tattgtatca agctaactag caatggtggt      1140
acagtggatg aaaagtgttt ctctgttgat gaaatagtgc aaccagatcc acccattgcc      1200
ctcaactgga ctttactgaa cgtcagttta actgggattc atgcagatat ccaagtgaga      1260
tgggaagcac cacgcaatgc agatattcag aaaggatgga tggttctgga gtatgaactt      1320
caatacaaag aagtaaatga aactaaatgg aaaatgatgg accctatatt gacaacatca      1380
gttccagtgt actcattgaa agtggataag gaatatgaag tgcgtgtgag atccaaacaa      1440
cgaaactctg gaaattatgg cgagttcagt gaggtgctct atgtaacact tcctcagatg      1500
agccaa                                                                 1506

<210> SEQ ID NO 68
<211> LENGTH: 1491
<212> TYPE: DNA
<213> ORGANISM: artificial sequence
<220> FEATURE:
<223> OTHER INFORMATION: Fusion proteins

<400> SEQUENCE: 68
atggctacag gctcccggac gtccctgctc ctggcttttg gcctgctctg cctgccctgg       60
cttcaagagg gcagtgcctc tgtgagtgaa atacagctta tgcataacct gggaaaacat      120
ctgaactcga tggagagagt agaatggctg cgtaagaagc tgcaggatgt gcacaatttt      180
ggtggcggag gtagtggtgg cggaggtagc ggtggcggag gttctggtgg cggaggttcc      240
gatgacgtca tgactaaaga ggaacagatc ttcctgctgc accgtgctca ggcccagtgc      300
gaaaaacggc tcaaggaggt cctgcagagg ccagccagca taatggaatc agacaaggga      360
tggacatctg cgtccacatc agggaagccc aggaaagata aggcatctgg aagctctac       420 cctgagtctg aggaggacaa ggaggcaccc actggcagca ggtaccgagg gcgcccctgt      480
ctgccggaat gggaccacat cctgtgctgg ccgctggggg caccaggtga ggtggtggct      540
gtgccctgtc cggactacat ttatgacttc aatcacaaag gccatgccta ccgacgctgt      600
gaccgcaatg gcagctggga gctggtgcct gggcacaaca ggacgtgggc caactacagc      660
gagtgtgtca aatttctcac caatgagact cgtgaacggg aggtgtttga ccgcctgggt      720
ggcggaggta gtggtggcgg aggtagcggt ggcggaggtt ctggtggcgg aggttccttt      780
```

```
tctggaagtg aggccacagc agctatcctt agcagagcac cctggagtct gcaaagtgtt    840
aatccaggcc taaagacaaa ttcttctaag gagcctaaat tcaccaagtg ccgttcacct    900
gagcgagaga cttttcatg ccactggaca gatgaggttc atcatggtac aaagaaccta    960
ggacccatac agctgttcta taccagaagg aacactcaag aatggactca agaatggaaa   1020
gaatgccctg attatgtttc tgctggggaa aacagctgtt actttaattc atcgtttacc   1080
tccatcgcaa taccttattg tatcaagcta actagcaatg gtggtacagt ggatgaaaag   1140
tgtttctctg ttgatgaaat agtgcaacca gatccaccca ttgccctcaa ctggacttta   1200
ctgaacgtca gtttaactgg gattcatgca gatatccaag tgagatggga agcaccacgc   1260
aatgcagata ttcagaaagg atggatggtt ctggagtatg aacttcaata caaagaagta   1320
aatgaaacta atggaaaat gatggaccct atattgacaa catcagttcc agtgtactca   1380
ttgaaagtgg ataaggaata tgaagtgcgt gtgagatcca acaacgaaa ctctggaaat   1440 tatggcgagt tcagtgaggt gctctatgta acacttcctc agatgagcca a            1491

<210> SEQ ID NO 69
<211> LENGTH: 963
<212> TYPE: DNA
<213> ORGANISM: artificial sequence
<220> FEATURE:
<223> OTHER INFORMATION: Fusion proteins

<400> SEQUENCE: 69
atggctacag gctcccggac gtccctgctc ctggcttttg gcctgctctg cctgccctgg     60
cttcaagagg gcagtgcctc tgtgagtgaa atacagctta tgcataacct gggaaaacat    120
ctgaactcga tggagagagt agaatggctg cgtaagaagc tgcaggatgt gcacaatttt    180
ggtggcggag gtagtggtgg cggaggtagc ggtggcggag gttctggtgg cggaggttcc    240
ttttctggaa gtgaggccac agcagctatc cttagcagag caccctggag tctgcaaagt    300
gttaatccag gcctaaagac aaaattcttct aaggagccta aattcaccaa gtgccgttca    360
cctgagcgag agacttttc atgccactgg acagatgagg ttcatcatgg tacaaagaac    420
ctaggaccca tacagctgtt ctataccaga aggaacactc aagaatggac tcaagaatgg    480
aaagaatgcc ctgattatgt ttctgctggg gaaaacagct gttactttaa ttcatcgttt    540
acctccatcg caataccta ttgtatcaag ctaactagca atggtggtac agtggatgaa    600
aagtgtttct ctgttgatga aatagtgcaa ccagatccac ccattgccct caactggact    660
ttactgaacg tcagtttaac tgggattcat gcagatatcc aagtgagatg gaagcacca    720 cgcaatgcag atattcagaa aggatggatg gttctggagt atgaacttca atacaaagaa    780
gtaaatgaaa ctaatggaaa atgatggac cctatattga acatcagt tccagtgtac    840 tcattgaaag tggataagga atatgaagtg cgtgtgagat ccaaacaacg aaactctgga    900
aattatggcg agttcagtga ggtgctctat gtaacacttc tcagatgag ccaataaaag    960 ctt                                                                  963

<210> SEQ ID NO 70
<211> LENGTH: 741
<212> TYPE: DNA
<213> ORGANISM: artificial sequence
<220> FEATURE:
<223> OTHER INFORMATION: Fusion proteins

<400> SEQUENCE: 70
atggctacag gctcccggac gtccctgctc ctggcttttg gcctgctctg cctgccctgg     60
```

```
cttcaagagg gcagtgcctc tgtgagtgaa atacagctta tgcataacct gggaaaacat    120
ctgaactcga tggagagagt agaatggctg cgtaagaagc tgcaggatgt gcacaatttt    180
ggtggcggag gtagtggtgg cggaggtagc ggtggcggag gttctggtgg cggaggttcc    240
gatgacgtca tgactaaaga ggaacagatc ttcctgctgc accgtgctca ggcccagtgc    300
gaaaaacggc tcaaggaggt cctgcagagg ccagccagca taatggaatc agacaaggga    360
tggacatctg cgtccacatc agggaagccc aggaaagata aggcatctgg gaagctctac    420
cctgagtctg aggaggacaa ggaggcaccc actggcagca ggtaccgagg gcgcccctgt    480
ctgccggaat gggaccacat cctgtgctgg ccgctggggg caccaggtga ggtggtggct    540
gtgccctgtc cggactacat ttatgacttc aatcacaaag ccatgcctac cgacgctgt     600 gaccgcaatg gcagctggga gctggtgcct gggcacaaca ggacgtgggc caactacagc    660
gagtgtgtca aatttctcac caatgagact cgtgaacggg aggtgtttga ccgcctgacc    720
ggtcatcatc accatcacca t                                              741

<210> SEQ ID NO 71
<211> LENGTH: 717
<212> TYPE: DNA
<213> ORGANISM: artificial sequence
<220> FEATURE:
<223> OTHER INFORMATION: Fusion proteins

<400> SEQUENCE: 71
atggctacag gctcccggac gtccctgctc ctggcttttg gcctgctctg cctgccctgg     60
cttcaagagg gcagtgcctc tgtgagtgaa atacagctta tgcataacct gggaaaacat    120
ctgaactcga tggagagagt agaatggctg cgtaagaagc tgcaggatgt gcacaatttt    180
ggtggcggag gtagtggtgg cggaggtagc ggtggcggag gttctggtgg cggaggttcc    240
gatgacgtca tgactaaaga ggaacagatc ttcctgctgc accgtgctca ggcccagtgc    300
gaaaaacggc tcaaggaggt cctgcagagg ccagccagca taatggaatc agacaaggga    360
tggacatctg cgtccacatc agggaagccc aggaaagata aggcatctgg gaagctctac    420
cctgagtctg aggaggacaa ggaggcaccc actggcagca ggtaccgagg gcgcccctgt    480
ctgccggaat gggaccacat cctgtgctgg ccgctggggg caccaggtga ggtggtggct    540
gtgccctgtc cggactacat ttatgacttc aatcacaaag ccatgcctac cgacgctgt     600 gaccgcaatg gcagctggga gctggtgcct gggcacaaca ggacgtgggc caactacagc    660
gagtgtgtca aatttctcac caatgagact cgtgaacggg aggtgtttga ccgcctg       717

<210> SEQ ID NO 72
<211> LENGTH: 756
<212> TYPE: DNA
<213> ORGANISM: artificial sequence
<220> FEATURE:
<223> OTHER INFORMATION: Fusion proteins

<400> SEQUENCE: 72
atgatacctg caaaagacat ggctaaagtt atgattgtca tgttggcaat ttgtttttctt    60 acaaaatcgg atgggaaatc tgttaagaag agatctgtga gtgaaataca gcttatgcat    120
aacctgggaa aacatctgaa ctcgatggag agagtagaat ggctgcgtaa gaagctgcag    180
gatgtgcaca attttggtgg cggaggtagt ggtggcggag gtagcggtgg cggaggttct    240
ggtggcggag gttccgatga cgtcatgact aaagaggaac agatcttcct gctgcaccgt    300
```

| | |
|---|---:|
| gctcaggccc agtgcgaaaa acggctcaag gaggtcctgc agaggccagc cagcataatg | 360 |
| gaatcagaca agggatggac atctgcgtcc acatcaggga agcccaggaa agataaggca | 420 |
| tctgggaagc tctaccctga gtctgaggag gacaaggagg cacccactgg cagcaggtac | 480 |
| cgagggcgcc cctgtctgcc ggaatgggac cacatcctgt gctggccgct gggggcacca | 540 |
| ggtgaggtgg tggctgtgcc ctgtccggac tacatttatg acttcaatca caaaggccat | 600 |
| gcctaccgac gctgtgaccg caatggcagc tgggagctgg tgcctgggca acaggacg | 660 |
| tgggccaact acagcgagtg tgtcaaattt ctcaccaatg agactcgtga acgggaggtg | 720 |
| tttgaccgcc tgaccggtca tcatcaccat caccat | 756 |

<210> SEQ ID NO 73
<211> LENGTH: 732
<212> TYPE: DNA
<213> ORGANISM: artificial sequence
<220> FEATURE:
<223> OTHER INFORMATION: Fusion proteins

<400> SEQUENCE: 73

| | |
|---|---:|
| atgatacctg caaaagacat ggctaaagtt atgattgtca tgttggcaat ttgttttctt | 60 |
| acaaaatcgg atgggaaatc tgttaagaag agatctgtga gtgaaataca gcttatgcat | 120 |
| aacctgggaa acatctgaa ctcgatggag agagtagaat ggctgcgtaa gaagctgcag | 180 |
| gatgtgcaca attttggtgg cggaggtagt ggtggcggag gtagcggtgg cggaggttct | 240 |
| ggtggcggag gttccgatga cgtcatgact aaagaggaac agatcttcct gctgcaccgt | 300 |
| gctcaggccc agtgcgaaaa acggctcaag gaggtcctgc agaggccagc cagcataatg | 360 |
| gaatcagaca agggatggac atctgcgtcc acatcaggga agcccaggaa agataaggca | 420 |
| tctgggaagc tctaccctga gtctgaggag gacaaggagg cacccactgg cagcaggtac | 480 |
| cgagggcgcc cctgtctgcc ggaatgggac cacatcctgt gctggccgct gggggcacca | 540 |
| ggtgaggtgg tggctgtgcc ctgtccggac tacatttatg acttcaatca caaaggccat | 600 |
| gcctaccgac gctgtgaccg caatggcagc tgggagctgg tgcctgggca acaggacg | 660 |
| tgggccaact acagcgagtg tgtcaaattt ctcaccaatg agactcgtga acgggaggtg | 720 |
| tttgaccgcc tg | 732 |

<210> SEQ ID NO 74
<211> LENGTH: 969
<212> TYPE: DNA
<213> ORGANISM: artificial sequence
<220> FEATURE:
<223> OTHER INFORMATION: Fusion proteins

<400> SEQUENCE: 74

| | |
|---|---:|
| atgatacctg caaaagacat ggctaaagtt atgattgtca tgttggcaat ttgttttctt | 60 |
| acaaaatcgg atgggaaatc tgttaagaag agatctgtga gtgaaataca gcttatgcat | 120 |
| aacctgggaa acatctgaa ctcgatggag agagtagaat ggctgcgtaa gaagctgcag | 180 |
| gatgtgcaca attttggtgg cggaggtagt ggtggcggag gtagcggtgg cggaggttct | 240 |
| ggtggcggag gttccttttc tggaagtgag gccacagcag ctatccttag cagagcaccc | 300 |
| tggagtctgc aaagtgttaa tccaggccta agacaaatt cttctaagga gcctaaattc | 360 |
| accaagtgcc gttcacctga gcgagagact ttttcatgcc actggacaga tgaggttcat | 420 |
| catggtacaa agaacctagg acccatacag ctgttctata ccagaaggaa cactcaagaa | 480 |
| tggactcaag aatggaaaga atgccctgat tatgtttctg ctggggaaaa cagctgttac | 540 |

| | |
|---|---|
| tttaattcat cgtttacctc catcgcaata ccttattgta tcaagctaac tagcaatggt | 600 |
| ggtacagtgg atgaaaagtg tttctctgtt gatgaaatag tgcaaccaga tccacccatt | 660 |
| gccctcaact ggactttact gaacgtcagt ttaactggga ttcatgcaga tatccaagtg | 720 |
| agatgggaag caccacgcaa tgcagatatt cagaaaggat ggatggttct ggagtatgaa | 780 |
| cttcaataca agaagtaaa tgaaactaaa tggaaaatga tggaccctat attgacaaca | 840 |
| tcagttccag tgtactcatt gaaagtggat aaggaatatg aagtgcgtgt gagatccaaa | 900 |
| caacgaaact ctggaaatta tggcgagttc agtgaggtgc tctatgtaac acttcctcag | 960 |
| atgagccaa | 969 |

<210> SEQ ID NO 75
<211> LENGTH: 1506
<212> TYPE: DNA
<213> ORGANISM: artificial sequence
<220> FEATURE:
<223> OTHER INFORMATION: Fusion proteins

<400> SEQUENCE: 75

| | |
|---|---|
| atgatacctg caaaagacat ggctaaagtt atgattgtca tgttggcaat ttgttttctt | 60 |
| acaaaatcgg atgggaaatc tgttaagaag agatctgtga gtgaaataca gcttatgcat | 120 |
| aacctgggaa aacatctgaa ctcgatggag agagtagaat ggctgcgtaa gaagctgcag | 180 |
| gatgtgcaca attttggtgg cggaggtagt ggtggcggag gtagcggtgg cggaggttct | 240 |
| ggtggcggag gttccgatga cgtcatgact aaagaggaac agatcttcct gctgcaccgt | 300 |
| gctcaggccc agtgcgaaaa acggctcaag gaggtcctgc agaggccagc cagcataatg | 360 |
| gaatcagaca agggatggac atctgcgtcc acatcaggga agcccaggaa agataaggca | 420 |
| tctgggaagc tctaccctga gtctgaggag gacaaggagg cacccactgg cagcaggtac | 480 |
| cgagggcgcc cctgtctgcc ggaatgggac acatcctgt gctggccgct gggggcacca | 540 |
| ggtgaggtgg tggctgtgcc ctgtccggac tacaagtatg acttcaatca caaaggccat | 600 |
| gcctaccgac gctgtgaccg caatggcagc tgggagctgg tgcctgggca acaggacg | 660 |
| tgggccaact acagcgagtg tgtcaaattt ctcaccaatg agactcgtga acgggaggtg | 720 |
| tttgaccgcc tgggtggcgg aggtagtggt ggcggaggta gcggtggcgg aggttctggt | 780 |
| ggcggaggtt ccttttctgg aagtgaggcc acagcagcta ccttagcag agcaccctgg | 840 |
| agtctgcaaa gtgttaatcc aggcctaaag acaaattctt ctaaggagcc taaattcacc | 900 |
| aagtgccgtt cacctgagcg agagactttt tcatgccact ggacagatga ggttcatcat | 960 |
| ggtacaaaga acctaggacc catacagctg ttctatacca gaggaacac tcaagaatgg | 1020 |
| actcaagaat ggaaagaatg ccctgattat gtttctgctg gggaaaacag ctgttacttt | 1080 |
| aattcatcgt ttacctccat cgcaataact tattgtatca agctaactag caatggtgg | 1140 |
| acagtggatg aaaagtgttt ctctgttgat gaaatagtgc aaccagatcc acccattgcc | 1200 |
| ctcaactgga ctttactgaa cgtcagttta actgggattc atgcagatat ccaagtgaga | 1260 |
| tgggaagcac cacgcaatgc agatattcag aaaggatgga tggttctgga gtatgaactt | 1320 |
| caatacaaag aagtaaatga aactaaatgg aaaatgatga ccctatatt gacaacatca | 1380 |
| gttccagtgt actcattgaa agtggataag gaatatgaag tgcgtgtgag atccaaacaa | 1440 |
| cgaaactctg gaaattatgg cgagttcagt gaggtgctct atgtaacact tcctcagatg | 1500 |
| agccaa | 1506 |

The invention claimed is:

1. A fusion polypeptide comprising SEQ ID NO: 20.

2. A fusion polypeptide comprising an amino sequence consisting of amino acids 32 to 323 of SEQ ID NO: 20.

3. A fusion polypeptide consisting of:
   i) a parathyroid hormone polypeptide consisting of SEQ ID NO: 54,
   ii) a linker consisting of four copies of the amino acid sequence GGGGS; and
   iii) a growth hormone binding domain of a growth hormone receptor polypeptide consisting of SEQ ID NO: 7;
   wherein i), ii) and iii) are arranged as an in frame translational fusion in an N- to C-terminal direction.

4. A nucleic acid molecule encoding the fusion polypeptide of claim 1.

5. A nucleic acid molecule encoding the fusion polypeptide of claim 2.

6. A nucleic acid molecule encoding the fusion polypeptide of claim 3.

7. A vector comprising the nucleic acid molecule of claim 4.

8. A vector comprising the nucleic acid molecule of claim 5.

9. A vector comprising the nucleic acid molecule of claim 6.

10. An isolated cell transfected or transformed with the nucleic acid molecule of claim 4 or a vector comprising the nucleic acid molecule.

11. An isolated cell transfected or transformed with the nucleic acid molecule according to claim 5 or a vector comprising the nucleic acid molecule.

12. An isolated cell transfected or transformed with the nucleic acid molecule according to claim 6 or a vector comprising the nucleic acid molecule.

13. A pharmaceutical composition comprising the fusion polypeptide of claim 1 and an excipient or carrier.

14. A pharmaceutical composition comprising the fusion polypeptide of claim 2 and an excipient or carrier.

15. A pharmaceutical composition comprising the fusion polypeptide of claim 3 and an excipient or carrier.

16. A method for producing a fusion polypeptide comprising:
   i) providing a cell transfected or transformed with the nucleic acid molecule of claim 4 or a vector comprising the nucleic acid molecule, and cell culture medium;
   ii) culturing the cell; and
   iii) isolating the fusion polypeptide from the cell or medium.

17. A method for the production of a fusion polypeptide comprising:
   i) providing a cell transfected or transformed with the nucleic acid molecule of claim 5 or a vector comprising the nucleic acid molecule, and cell culture medium;
   ii) culturing the cell; and
   iii) isolating the fusion polypeptide from the cell or medium.

18. A method for the production of a fusion polypeptide comprising:
   i) providing a cell transfected or transformed with the nucleic acid molecule of claim 6 or a vector comprising the nucleic acid molecule, and cell culture medium;
   ii) culturing the cell; and
   iii) isolating the fusion polypeptide from the cell or medium.

* * * * *